United States Patent [19]
Lang et al.

[11] 4,125,614
[45] Nov. 14, 1978

[54] THIAZOLIDINE DERIVATIVES

[75] Inventors: Hans-Jochen Lang, Altenhain, Taunus; Roman Muschaweck, Frankfurt am Main, both of Fed. Rep. of Germany

[73] Assignee: Hoechst Aktiengesellschaft, Frankfurt am Main, Fed. Rep. of Germany

[21] Appl. No.: 788,905

[22] Filed: Apr. 19, 1977

Related U.S. Application Data

[62] Division of Ser. No. 599,103, Jul. 25, 1975, Pat. No. 4,061,761.

[30] Foreign Application Priority Data

Jul. 27, 1974 [DE] Fed. Rep. of Germany ....... 2436263

[51] Int. Cl.² ................. C07D 239/70; A61K 31/425

[52] U.S. Cl. ............................. 424/251; 260/306.7 T; 424/270; 544/250; 544/278; 546/280; 546/270
[58] Field of Search ................. 260/256.5 R, 306.7 T; 424/270, 251; 544/278

[56] References Cited

U.S. PATENT DOCUMENTS 3,853,872  8/1977  Wei et al. ........................ 260/251 A

Primary Examiner—Donald G. Daus
Assistant Examiner—Lisa Jones
Attorney, Agent, or Firm—Curtis, Morris & Safford

[57] ABSTRACT

The invention relates to thiazolidine derivatives having in 4-position a hydroxy group and a 3'-sulphamyl-phenyl substituent, in 2-position an imino group and in 1-position an aliphatic or cycloaliphatic substituent. Said thiazolidines have diuretic activity.

The invention also relates to a process for the manufacture of said compounds.

10 Claims, No Drawings

THIAZOLIDINE DERIVATIVES

This is a divisional of application Ser. No. 599,103 filed July 25, 1975, now U.S. Pat. No. 4,061,761 granted Dec. 6, 1977.

The present invention relates to thiazolidine derivatives and a process for their manufacture.

The thiazolidine derivatives of the invention have the general formula I

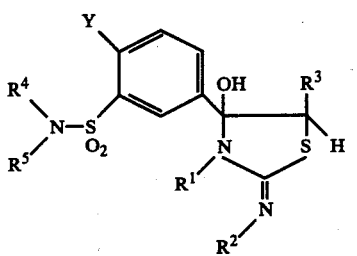

in which $R^1$ stands for alkyl or alkenyl radicals of 1 to 4 carbon atoms, cycloalkyl radicals of 3 to 6 carbon atoms or dialkylamino groups having a total of 7 carbon atoms, which may form together with the nitrogen atom of the amino group a saturated heterocyclic ring, $R^2$ stands for an alkyl or alkenyl or alkinyl radical of 1 to 8 carbon atoms, optionally substituted by alkoxy groups of 1 to 4 carbon atoms, cycloalkyl radicals of 3 to 8 carbon atoms, phenylalkyl radicals of 1 to 2 carbon atoms in the alkyl moiety, optionally substituted in the phenyl ring by halogen, lower alkyl, alkoxy, alkylenedioxy, further for alkyl groups of 1 to 2 carbon atoms which are substituted by cycloalkyl radicals of 3 to 6 carbon atoms or 5- or 6-membered saturated or unsaturated heterocyclic radicals containg oxygen, nitrogen or sulfur, or for dialkylamino groups having a total of 7 carbon atoms, which may form together with the nitrogen atom of the amino group a saturated heterocyclic ring, and in which $R^1$ and $R^2$ together may also stand for an alkylene group of 2 to 4 carbon atoms, $R^3$ stands for hydrogen or alkyl of 1 to 2 carbon atoms, $R^4$ and $R^5$ are identical or different and each stands for hydrogen, alkyl or alkenyl radicals of 1 to 6 carbon atoms, optionally substituted by alkoxy of 1 to 4 carbon atoms, cycloalkyl or cycloalkylalkyl of 3 to 8 carbon atoms, phenyl, phenylalkyl of 1 to 3 carbon atoms in the alkyl moiety, and the phenyl ring may, optionally, be substituted by halogen, lower alkoxy, alkoxy, alkylenedioxy, further for alkyl groups of 1 to 2 carbon atoms which are substituted by 5- or 6-membered unsaturated heterocyclic radicals containing oxygen, nitrogen or sulfur; $R^4$ and $R^5$ may also form together with the nitrogen atom a saturated, optionally methyl-substituted, 5- to 6-membered heterocyclic ring, in which optionally, a $CH_2$-group may be replaced by oxygen, and Y stands for hydrogen, halogen, methyl or trifluoromethyl.

This invention also relates to the acid addition salts with pharmaceutically acceptable acids.

Further object of the invention is a process for the manufacture of the compounds of the general formula I which comprises (a) reacting compounds of the general formula II

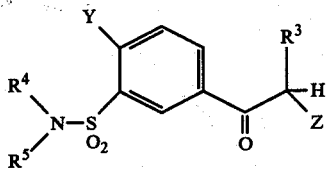

in which $R^3$, $R^4$, $R^5$ and Y are defined as above and Z stands for the radical of an activated ester of an inorganic acid, with thioureas of the general formula III, which can be represented by formulae IIIa and IIIb

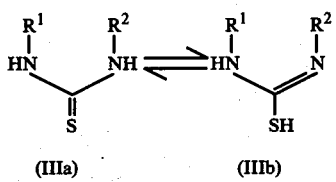

in which $R^1$ and $R^2$ are defined as above or (b) treating compounds of the general formula IV

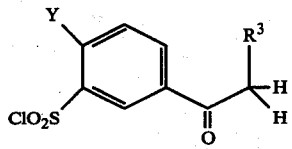

in which $R^3$ and Y are defined as above, with a halogenating agent and reacting the α-halogen ketones of the general formula V

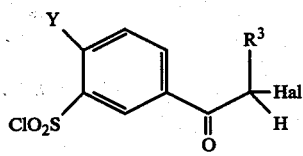

thus obtained in which $R^3$ and Y are defined as above and Hal stands for Cl or Br, if desired without isolation or purification, with thioureas of the formula III and reacting the thiazolidine derivatives thus obtained of the general formula VI

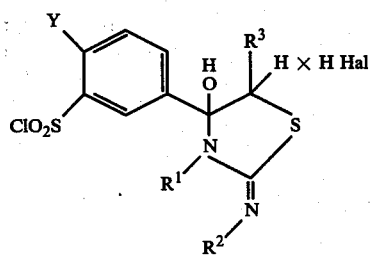

in which $R^1$, $R^2$ and $R^3$ are defined as above, with ammonia, a primary or secondary amine of the general formula VII

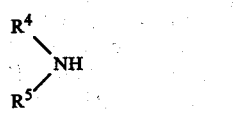

in which $R^4$ and $R^5$ are defined as above or
(c) reacting compounds of the general formula VIII

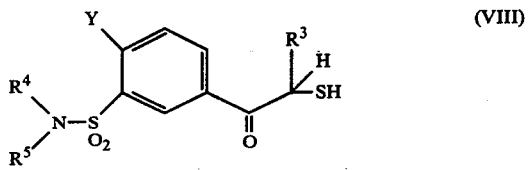

with compounds of the formula IX

in which $R^1$, $R^2$, $R^3$ and Y are defined as above, Hal stands for chlorine or bromine,
(d) reacting compounds of the formula VIII with carbodiimides of formula X

in which $R^1$ and $R^2$ are defined as above
(e) treating compounds of the general formula XI

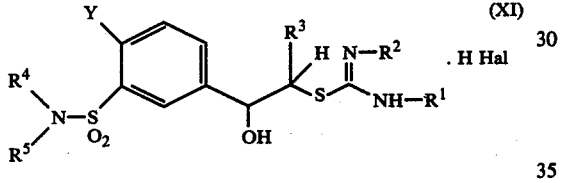

in which $R^1$, $R^2$, $R^3$, $R^4$ and $R^5$ and Y are defined as above, and Hal stands for chlorine or bromine with an oxidation agent or
(f) reacting compounds of the general formula XII

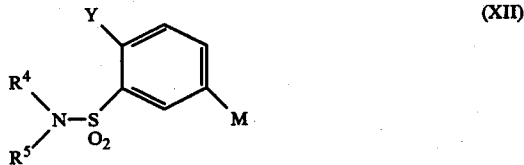

in which $R^4$ and $R^5$ and Y are defined as above but $R^4$ and $R^5$ do not stand for hydrogen and Y not for bromine or iodine and M stands for lithium or a MgBr-group, with compounds of the general formula XIII

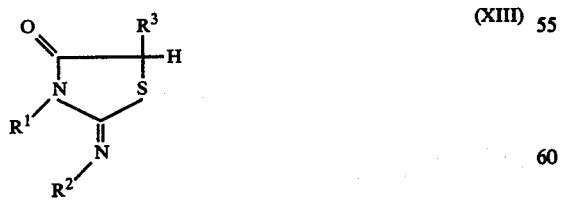

in which $R^1$, $R^2$ and $R^3$ are defined as above and hydrolizing the reaction product obtained
and optionally converting the compounds of the general formula I obtained according to methods (a)–(f) in which $R^4$ and/or $R^5$ stands for hydrogen, by a usual alkylation into compounds in which $R^4$ and/or $R^5$ has one of the definitions given hereinbefore and/or converting the compounds of the formula I, prepared according to the methods indicated under (a)–(f), with organic or inorganic acids into the acid addition salts thereof or the salts obtained of the compounds of the general formula I with bases into the free basic compounds of the formula I.

Suitable organic acids are, for example:
formic acid, acetic acid, benzoic acid, succinic acid, fumaric acid, maleic acid, lactic acid, tartaric acid, citric acid, salicylic acid, oxethanesulfonic acid, ethylenediamine-tetraacetic acid, methanesulfonic acid, p-toluenesulfonic acid and others.

Compounds I and VI can also be in their tautomeric forms, which are:

The compounds of the invention of the formula I can also be in their possible geometrical isomer structures. The alkyl or alkenyl radicals in the substituents $R^1$ to $R^5$ can be not only straight-chained but also branched.

The cyclic compounds of the formula I are in equilibrium with the position isomer compounds of the formula Ic and the acid addition salts thereof of the formula Ic

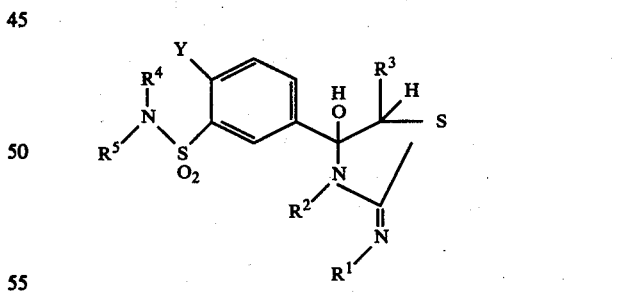

via the open-chained tautomeric form Ia, if the radicals $R^1$ and $R^2$ are different. Which of the two cyclic isomers I or Ic or the acid addition salts thereof is preferably present, especially depends on the different volume of the substituents $R^1$ or $R^2$ in such a way that the substituent having the smaller volume is preferably in the 3-position of the thiazolidine ring system. For the compounds of the invention, only one of the possible isomeric or tautomeric forms of a substance is indicated for the sake of simplicity in the following text.

Method (a) is advantageously performed by reacting the compounds II with the thioureas III in the molar ratio of 1:1 to 1:1.5. The use of larger molar excesses of thiourea is possible but generally goes without notable advantages. The reaction is advantageously carried out in an inert solvent, for example in polar organic solvents such as dimethyl formamide, dimethyl acetamide, dioxane, tetrahydrofurane, acetonitrile, nitromethane, diethylene glycoldimethyl ether and others. However, especially advantageous reaction agents proved to be lower alkyl acetates, such as methyl- and ethyl acetate, lower alcohols of 1–4 carbon atoms, especially methanol, ethanol, isopropanol, and lower dialkyl ketones, such as, for example acetone and methyl-ethyl-ketone, as well as mixtures of these solvents and mixtures of these solvents alone or with less suitable solvents, for example, methanol/benzene, ethanol/toluene, methanol/diethyl ether, ethanol/carbon tetrachloride, acetone/chloroform, with the more polar solvent advantageously being in excess. The reactants may be suspended or dissolved in the respective solvent. In principle, the reactants may also be reacted without the use of a solvent, especially when the thiourea concerned melts at a low temperature, however, due to the exothermal course of reaction side reactions may occur so that this embodiment of the reaction has no advantages over the operational method in solvents. The reaction occurs moderately exothermal and may be carried out at 0° to 100° C., preferably at 10° and 70° C., and with special advantage, between 20° and 55° C.

The reaction period largely depends on the reaction temperature and is in the range of 2 minutes at elevated temperatures and of 60 hours at lower temperatures. In general, the reaction takes from 5 minutes to 40 hours in the favourable temperature range.

In many cases, compounds I precipitate in the form of their acid addition salts in the course of the reaction if they are sparingly soluble. Optionally, the later addition of a suitable precipitating agent in the end of the reaction may increase the yield, suitable precipitating agents being, for example, hydrocarbons, such as benzene, toluene, cyclohexane, petroleum ether, ligroin, carbon tetrachloride, especially lower alkyl acetates of 1 to 4 carbon atoms in the alkyl portion, such as ethyl acetate, butyl acetate, dialkyl ethers of 4–8 carbon atoms, for example diethyl ether, diisopropyl ether and di-n-butyl ether. When the reacted compounds are in solution form, the salts of compounds I are advantageously precipitated, optionally after concentrating the reaction solution, with one of the precipitating agents mentioned or the solution is advantageously introduced, while filtering and stirring, in one of the precipitating agents mentioned to eliminate inhomogeneous impurities. Since the yield of the reaction of compounds II with the thioureas III is practically quantitative when performed under optimal conditions, the crude products obtained of the compounds desired are mostly pure as per analysis.

The thioureas III used are mostly substances that are described in literature. They are prepared in known manner by reacting amines with isothiocyanates, carbon disulfide or thiophosgen (cf. Houben-Weyl, "Methoden der organischen Chemie" vol. 2, page 884, 4th edition, Georg-Thieme-Verlag Stuttgart, 1955).

The compounds of the formula II contain as radical of an activated ester Z for example, Cl, Br, I, —O—CO—C$_6$H$_4$—NO$_2$, CH$_3$—SO$_2$—O—, C$_2$H$_5$—SO$_2$—O, C$_6$H$_5$—SO$_2$—O—, CH$_3$C$_6$H$_4$—SO$_2$—O—. They can be obtained according to various methods.

The diazo ketones of the general formula XIV

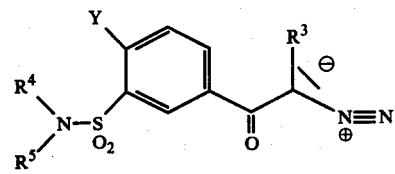

can be converted with acids into the ketones of the formula II. This method as well as a number of compounds II and XIV are known in literature (cf. Swiss Pat. No. 389,591 and Belgian Pat. No. 610,633) and the other compounds of the formulae II and XIV can be prepared and reacted accordingly.

Since diazo alkanes are highly toxic, explosive and difficult to handle, the compounds of the formula II in which $R^3$, $R^4$, $R^5$ and Y are defined as above and Z stands for chlorine or bromine are advantageously prepared by reacting compounds of the general formula XV

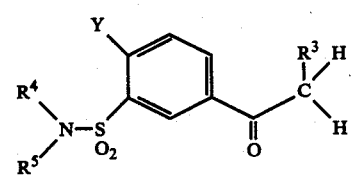

with suitable halogenating agents, for example elementary chlorine or bromine, sulfuryl chloride, monochlorourea, copper-II-bromide, bromodioxane, N-bromosuccinimide under conditions known in literature. The easily accessible compounds XV are known in literature if Y stands for chlorine, $R^3$ is hydrogen, methyl and ethyl and $R^4 = R^5$ stands for hydrogen (E. Jucker, A. Lindenmann, E. Schenker, E. Fluckinger and M. Taeschler, Arzneimittel-Forsch. 13, 269 (1963)). The other compounds for the process of the invention of the formula XV either are prepared in an analogous manner, or, if $R^4$ and $R^5$ in the formula XV each stands for hydrogen, are converted in the usual manner by means of alkylation agents into other compounds of the formula XV.

The compounds of the formula II can also be prepared by reacting the α-hydroxyketones of the general formula XVI

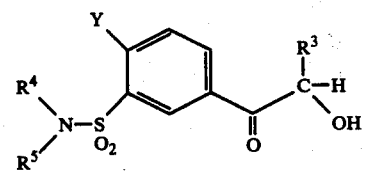

known from Swiss Pat. No. 389,591 or correspondingly substituted compounds that can be prepared in an analogous manner, under conditions known in literature with the activated derivatives or organic and inorganic acids, such as methanesulfonic facid chloride, ethane sulfonic acid chloride, benzenesulfonic acid chloride, p-toluenesulfonic acid chloride, thionyl bromide, phosphorous trichloride, phosphorous tribromide, phosphorous oxide chloride, p-nitrobenzoyl chloride.

The hydroxyketones in which $R^4$ is H, $R^3$ and $R^5$ each is hydrogen or lower alkyl, Y is hydrogen, halogen, trifluoromethyl, lower alkyl or alkoxy, are known in literature (cf. Swiss Pat. No. 389;591).

According to the method described under (b) sulfochlorides of the general formula IV are reacted with a halogenating agent, such as, for example elementary chlorine, with sulfuryl chloride, monochloro urea, bromodioxane, N-bromosuccinimide, especially, however, with elementary bromine or with copper-II-bromide. Compound IV is halogenated with bromine by adding dropwise undilute or dilute bromine to a solution or suspension of the equimolar amount of compound IV in an inert solvent, for example halogenated hydrocarbon, such as chloroform or methylene chloride, in acetic acid, preferably, however, in a lower alkyl acetate, such as methyl acetate, ethyl acetate, n-butyl acetate or in a mixture of these solvents at 0° to 50° C., preferably at 10° to 35° C. Since halogenating reactions of the ketone are catalyzed by acids, the reaction solution is inoculated either a priori with catalytic amounts of acid, advantageously with hydrobromic acid or the protons required for reaction are produced after adding dropwise a small amount of bromine and subsequent heating the reaction mixture until halogen has decolored, which can be done by shortly increasing the temperature range. Suitable diluents for the bromine to be added dropwise are the inert solvents mentioned or mixtures thereof. The compounds IV in which $R^3$ is defined as above and Y stands for chlorine, are known in literature.

The compounds IV are brominated with copper-II-chloride according to the method described by J. Org. Chem. 29, 3459, (1964) the ketones IV being boiled with 2 mols of powdered copper-II-bromide in water-free or alcohol-free ethyl acetate or mixtures of ethyl acetate and chloroform until the dark color of the copper-II-bromide has disappeared and colorless copper-I-bromide has precipitated instead, that can subsequently be separated by filtration.

A suitable chlorinating agent is especially sulfuryl chloride that can be reacted with a solution or a suspension of the compounds IV in a suitable solvent, preferably a halogenated hydrocarbon, for example chloroform or cabon tetrachloride. The reaction is carried out preferably within 5 to 30 hours within a temperature of from 10° to 100° C., preferably within 20° and 80° C., hydrolization follows optionally after concentrating the reaction mixture with ice water and the organic phases are worked up.

The solution or suspension obtained according to the corresponding methods are advantageously evaporated under reduced pressure and the compounds V obtained as residue are purified by crystallization in inert solvents, for example benzene, toluene, carbon tetrachloride, cyclohexane, petroleum ether and others. However, it is more advantageous to react the compounds V so obtained without further purification in a suitable inert solvent with the equimolar amount of thiourea III to yield the compounds of the general formula VI. When the halogenated ketone V is reacted with the thioureas III without prior isolation, the amount of the thiourea III to be used is calculated on the ketone IV. The use of 1.5 mols of thiourea can lead to higher yields of compound VI whereas the use of greater excesses of compound III has no notable advantages. Suitable inert solvents are, for example dimethyl formamide and dimethyl acetamide, dioxane, tetrahydrofurane, acetonitrile, nitromethane, diethylene-glycol-dimethyl ether and others, especially suitable solvents are lower alkyl acetates, for example methyl, ethyl or n-butyl acetate, as well as lower dialkyl ketones, for example acetone and methyl-ethyl ketone, as well as mixtures of these solvents. The reaction is moderately exothermal and is effected at 0° to 60° C., preferably at 20° to 40° C. The reaction times are especially dependent on the reaction temperature used and are within the range of from 5 minutes to 40 hours.

The thiazolidines of the formula VI precipitate in the course of the reaction mostly as sparingly soluble substances and in the end of the reaction, optionally after concentration, the yield of compound VI can be improved by adding a suitable precipitating agent. Suitable precipitating agents are the solvents used in the operational method (a) for the same purposes. When the reaction yields a solution, the compounds of the formula VI are advantageously precipitated, optionally after concentration of the reaction mixture, with one of the precipitating agents mentioned or they are advantageously introduced into the corresponding precipitating agent while filtering and stirring. The compounds of the formula VI prepared according to this method are generally distinguished by a high purity, however, should they need to be purified, they can be recrystallized from an inert, suitable solvent free from water and alcohol, if possible, for example acetone, methyl-ethyl ketone, acetonitrile, nitromethane. However, reprecipitation is especially advantageous to avoid a heavy thermal charge of compounds VI. For this purpose, the crude product of the formula VI is dissolved in a pure and inert solvent, for example in dimethyl formamide, dimethyl acetamide, acetone, acetonitrile, nitromethane at a temperature within the range of from 0° to 30° C., the solution is treated optionally with active charcoal and the compounds are precipitated after filtration with one of the precipitating agents mentioned.

The reaction of the halogen ketones V with the thioureas III to yield the thiazolidines VI is surprising inasmuch as, on the one hand, the thioureas III specifically react with the bromoketone radical in compound V without the chlorosulfonyl grouping being attacked and on the other hand, as the sulfochloride moiety of compounds V and VI does not react with the hydroxy groups of compounds VI despite the presence of the thioureas III reacting as weak bases.

Now, the sulfonic acid chlorides so obtained of the general formula VI are reacted with ammonia or an amine of the formula VII to yield compounds of the formula I. For this reaction, aqueous solutions of ammonia or of the amines VII as well as liquid ammonia or pure amines can be used in excess, the excess amount of ammonia or amine acting as solvent. The reaction may also be effected in organic solvents, for example dimethyl formamide, dimethyl acetamide, dimethyl sulfoxide, dioxane, tetrahydrofurane, diethyleneglycol dimethyl ether, however, lower alcohols of 1–4 carbon atoms, for example methanol, ethanol or isopropanol being especially suitable. Theoretically, the conversion of the sulfochlorides VI to the sulfonamides I requires 1 mol of ammonia or amine VII in the presence of 2 mols of an auxiliary base. For this reason, at least 3 mols of ammonia or amine VII, preferably 3–7 mols are used per mol of sulfochloride VI, however, greater excesses of VII can be used. One or two mols of ammonia or amine VII can be used if an auxiliary base is present, about 1–6 mols equivalent of auxiliary base being used. Suitable auxiliary bases are inorganic or organic hydroxides, carbonates and hydrogen carbonates, and salt solutions of weak inorganic or organic acids, tertiary amines, for example triethyl amine, tri-n-butyl amine, methyl-dicyclohexyl amine, ethyl-dicyclohexyl amine being especially advantageous in all cases. When used in excess, the tertiary amine can also serve as reactant without adding a solvent. The reaction is exothermal, so cooling is advantageous and working is carried out at temperatures within the range of from −35° to +60°

(c). The reactions can be performed in a range of temperature of from 0° to 40° C., preferably 10° to 30° C. and at a reaction time of 1 to 20 hours.

The compounds of the formula VIII used in operational methods (c) and (d) can be obtained by various methods, for example by converting the compounds of the formula II with thiocarboxylic acids of the formula XVII

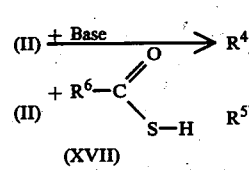 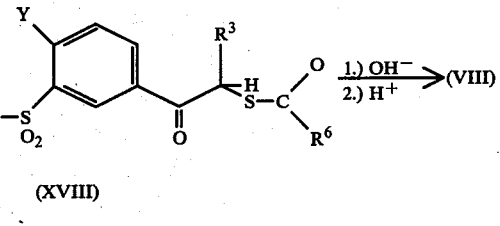

C., preferably from +10° to +35° C. The reaction time should last 30 minutes at least and the reaction can be interrupted after two days at the latest, longer reaction times not being more advantageous. A reaction time of 6 to 20 hours is preferred. The reaction products are worked up advantageously by diluting with water, optionally after distilling off the amine and concentrating the reaction mixture, the compounds I being precipitated as sparingly soluble substances. When in the compound I so prepared $R^4$ or $R^5$ is hydrogen, the pH should be adjusted to 7.5-8.5, if possible. Immediately after precipitating with water, the compounds I are mostly separated in the form of visquous oils that crystallize more or less rapidly when the substituents $R^1$ and $R^2$ have a small volume. Crystallization can be accelerated by treating several times with a suitable solvent, such as, for example water, ether, diisopropyl ether, carbon tetrachloride, petroleum ether, n-butyl acetate and others.

After precipitating with water, compounds I can also be extracted with a suitable solvent, preferably a lower alkyl acetate, for example methyl or ethyl acetate. After drying the extract over a suitable drying agent, for example sodium or magnesium sulfate, compounds I are preferably obtained by evaporating the solution under reduced pressure.

The compounds I can also be converted to the corresponding acid addition products without further isolation and purification by treating with a protonic acid H-Z.

According to method (c) compounds of the formula VIII are reacted in a solvent with the known compounds of the formula IX. Suitable solvents are lower alcohols having 1-4 carbon atoms and lower alkyl acetates with 1-4 carbon atoms in the alkyl part, for example methyl and ethyl acetate.

The reactions are generally performed within a temperature range of from 0° to 60° C., preferably 15° to 35° C. and with a reaction time of 5 to 60 hours. Especially suitable are compounds VIII that carry on the sulfamoyl group, in addition to $R^4$ = hydrogen, a voluminous organic radical $R^5$, for example cyclooctyl or tertiary butyl, or in which $R^4$ and $R^5$ each has an organic radical as substituent.

Method (d) is performed by reacting the mercapto ketones of the formula VIII in an anhydrous, polar, inert solvent, for example dioxane, tetrahydrofurane, methyl acetate or ethyl acetate, with the carbodiimides of the formula X in the molar ratio of 1:1. The substitution of $R^4$ and $R^5$ also applies for compounds of the formula VIII as being preferred according to method preferably with thioacetic acid ($R^6$=CH_3) in the presence of an equivalent of base, for example KOH, in aqueous or alcoholic medium into the thioesters of the general formula XVIII, that are hydrolized in slightly alkaline medium to give the compounds of the formula VIII.

It is also possible to react compounds II with alkali metal hydrogen sulfides in an inert solvent, for example sodium or potassium hydrogen sulfide in dimethyl formamide at temperatures ranging between 0° and 40° C. The processes by which compounds VIII are prepared are known in literature.

According to method (e) the compounds of the general formula XI are converted with a suitable oxidation agent, preferably with active manganese-IV-oxide, into the compounds of the formula I or their acid addition salts. The solvents preferably used are halogenated hydrocarbons, for example methylene chloride, chloroform and tetrachlorethane, the reaction being performed at a temperature ranging from 0° to 40° C., preferably from 20° to 30° C. during 10 to 60 hours.

The compounds of the formula XI are obtained by converting the halogen ketones of the formula II in which Z preferably stands for chlorine or bromine, for example according to "Arzneimittel-Forschung" 22, 2095, 1972 with a suitable reduction agent, preferably sodium boronhydride in methanol at a temperature within the range of from 0° to 25° C. into the compounds of the formula XIX

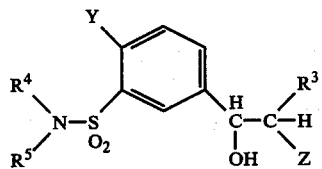

The compounds of the formula XIX react as alkyl halides with the thioureas of the formula III to give the isothiuronium salts of the formula XI.

The reaction is performed under the same conditions as described in operational method (a).

In operational method (f) compounds of the formula XII in which Y does not stand for bromine or iodine and $R^4$ and $R^5$ are different from hydrogen and each is an inert non protonic organic radical as defined above, are reacted with compounds of the formula XIII known in literature. The compounds XII and XIII are advantageously reacted in the molar ratio 1:1 to 1:1.5 in an inert and anhydrous solvent usual for metal organic reactions, preferably ether or tetrahydrofurane, at a temperature within the range of from 0° C. to 60° C., preferably from 15° to 35° C. and with a reaction time of 1 to 30 hours. In this reaction, a solution of the compounds XIII is added dropwise to a solution of the compounds XII, however, it is especially advantageous to do it the opposite way according to which the solution of 1 mol of the metalorganic compound XII is added dropwise to a solution of 1 to 1.5 mols of the compounds XIII in one of the solvents mentioned. After finishing the reaction, the reaction products are hydrolized in a manner usual for metal organic reactions, for example by introducing the reaction mixture at a temperature ranging between −5° C. and +20° C. into an aqueous, saturated ammonium chloride solution at a constant pH of 6–8. The compounds of the formula I so obtained are worked up in an analogous manner as described under method (b). The compounds of the formula XII used in operational method (f) are, for example prepared by converting compounds of the formula XX

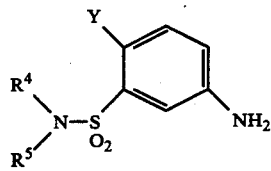

in known manner via diazotization by a Sandmeyer reaction or one of its variants, into the bromine derivatives of the formula XXI

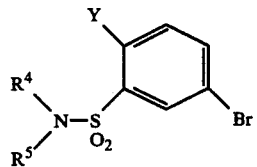

or by brominating compounds of the formula XXII

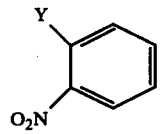

in m-position to the nitro group, reducing the nitro group, diazotizing the amino group obtained, sulfochlorinating according to Moerwein and finally reacting with an amine of the formula VII. Finally, the compounds of the formula XXI are converted according to known methods in an inert, anhydrous solvent, for example tetrahydrofurane or diethyl ether, into the compounds of the formula XXII. A great number of the compounds of the formula XIII used in method (f) is known in literature and is accessible by converting the thioureas of the formula III with α-halogenated carboxylic acids or the esters thereof in the general formula XXIII

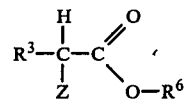

in which $R^3$ is defined as above, $R^6$ preferably stands for hydrogen, methyl or ethyl and Z stands for chlorine or bromine. (c.f. R. C. Elderfield, "Heterocyclic Compounds", vol. 5, page 616, John-Wiley & Sons, Inc. 1957). The compounds of the formula XIII that have not yet been described are prepared in the same manner.

The compounds of the formula I may be reacted reversibly in a suitable solvent with an acid of the formula H-Z. The compounds I may be introduced into the pure acids at 0° to 40° C., when they are liquid or have a melting point hardly higher than 40° C. and when they do not cause side reactions. However, it is advantageous to work in a solvent, for example in water or in an organic solvent, for example dioxane, tetrahydrofurane, ether, lower alkyl acetate with 1–4 carbon atoms in the alkyl part, acetonitrile, nitromethane, acetone, methylethyl ketone and others, lower alcohols of 1–4 carbon atoms being especially suitable. 1–1.5 mols of the acids H-Z are used per mol of compounds I, however, greater amounts of acid are also allowed. Temperatures within the range of from 0° to 40° C., preferably from 10° to 25° C. are advantageous. The reaction is moderately exothermal.

When working in aqueous solution the compounds I are, generally, instantly dissolved after adding acids of the formula H-Z and only in rare cases the corresponding acid addition compounds are separated. The salts of the invention are advantageously isolated with the obtention of a solution by careful evaporation of water, preferably by lyophilizing. When working in organic solvents the acid addition salts often precipitate after adding the corresponding acids H-Z as sparingly soluble substances. When a solution is obtained, the acid addition compounds are precipitated, optionally after concentrating the reaction mixture, with a suitable precipitating agent, those agents being the solvents described in method I for the same purpose.

Even when being highly pure, the acid addition products very often precipitate as visquous oils or as amorphous glasslike products. These amorphous products can be crystallized in many cases, optionally by heating to 40° to 80° C., and treating with an organic solvent. Solvents promoting crystallization are especially lower alkyl acetates of 1–4 carbon atoms in the alkyl part, for example methyl, ethyl, or n-butylacetate or dialkyl ketones, such as acetone or methylethyl ketone, lower dialkyl ethers, such as diethyl ether, diisopropyl ether or di-n-butyl ether, acetonitrile, nitromethane and, in some cases, lower alcohols, such as methanol, ethanol, isopropanol or n-butanol.

The acid addition products can be deprotonized in a suitable solvent by treating with bases to the compounds of the general formula I. Suitable bases are, for example, solutions of inorganic hydroxides, such as lithium, sodium, potassium, calcium or barium hydroxides, carbonates or hydrogen carbonates, such as sodium carbonate, potassium carbonate, sodium or potassium hydrogen carbonate, ammonia and amines, such as triethyl amine, dicyclohexyl amine, piperidine, methyl-di-cyclohexyl amine.

When working in aqueous medium, the free basic compounds I precipitate in sparingly soluble form and can be separated and isolated by filtration or extraction with an organic solvent, preferably ethyl acetate. Especially suitable organic reaction media are lower alcohols of 1–4 carbon atoms, preferably methanol and ethanol, however, ethyl acetate, diethyl ether, tetrahydrofurane, dioxane, diethylene glycol dimethyl ether, dimethyl formamide and others can also be used. There is spontaneous reaction to the compounds I. The reaction is performed at −35° C. to 100° C., preferably 0° to 25° C. When an organic solvent miscible with water is used, the free bases of the formula I are precipitated by adding water, optionally after concentrating the reaction mixture. When the solvent used is not miscible with water, the reaction mixture is advantageously washed with water after reaction and the organic solvent is evaporated optionally after drying. When at least 1 mol of a sufficiently strong base is allowed to act on the compounds of the formula I, in which $R^4$ and/or $R^5$ each stands for hydrogen, salts of the general formula XXIV are obtained

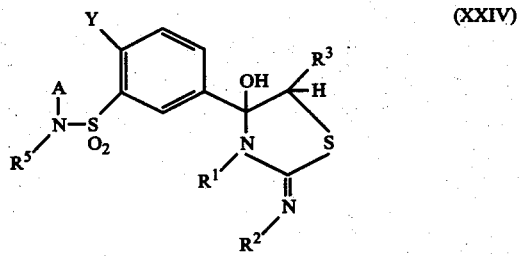

(XXIV)

accompanied by the deprotonization of the sulfonamide group, in which formula A is the cation of an alkali metal or alkaline-earth metal and $R^1$, $R^2$, $R^3$, $R^4$ and $R^5$ as well as Y are defined as above.

As suitable bases can be used hydroxides of the alkali metals or alkaline-earth metals, preferably NaOH and KOH, alkali metal or alkaline-earth metal alcoholates, preferably $NaOCH_3$ and $NaOC_2H_5$, NaH, sodium methylsulfinyl methide and others.

As solvents are used water or polar organic solvents, such as methanol, ethanol, isopropanol, n-butanol, dimethylformamide, dimethyl sulfoxide, diethylene glycol dimethyl ether, acetonitrile.

Especially the potassium salts of the formula XXIV are distinguished by their good solubility in water. By the addition of 1 mol of a suitable acid, the compounds of the formula I of the invention are recovered, favourable acids being especially ammonium salts.

This reversible acid-base reaction can be used for the purification of the compounds I. Moreover, the salts of the formula XXIV can be used in order to obtain compounds of the formula I which are correspondingly modified via alkylation reactions taking place at the sulfonamide group.

In the case of alkylation reactions, working is effected in water, preferably, however, in the polar organic solvents mentioned, and the reaction is carried out at temperatures within the range of from −20° C. to +50° C., preferably +15° C. to +35° C. during a period of time of from 5 to 72 hours. The alkylation reaction is performed with the usual alkylating agents of the general formula $R^4 — X$, in which $R^4$ is defined as indicated above, and X stands, for example, for Br, I, Cl, $—O—SO_2—CH_3$, $—O—SO_2—OR^4$,

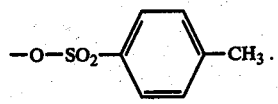

The most important compounds of the general formula I of the invention are those in which the substituents are defined as follows:
$R^1$ = methyl, ethyl, allyl,
$R^2$ = methyl, ethyl, allyl, methoxypropyl
$R^1$ and $R^2$ together = alkylene
$R^3$, $R^4$, $R^5$ = each hydrogen
Y = chlorine, bromine.

Furthermore preferred compounds of the formula I of the invention are those in which the substituents are defined as follows:
$R^1$ = propyl, isopropyl
$R^2$ = propyl, butyl, cyclohexyl, cyclohexylmethyl, benzyl
$R^3$ and $R^4$ each = hydrogen
$R^5$ = hydrogen, lower alkyl, benzyl
Y = chlorine, bromine.

In the process of the invention, there may be used in addition to the 4-(3-sulfamoyl-phenyl)-1,3-thiazolidine-4-ols described in the Examples the compounds of the general formula I

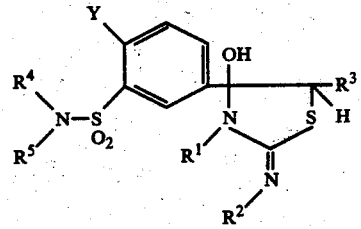

or the acid addition products thereof summarized in the following Table:

| $R^1$ | $R^2$ | $R^3$ | $R^4$ | $R^5$ | Y |
|---|---|---|---|---|---|
| $CH_3$ | $C_2H_5$ | H | H | H | Cl |
| $CH_3$ | $n-C_3H_7$ | H | H | H | Cl |
| $CH_3$ | $n-C_4H_9$ | H | H | H | Cl |
| $CH_3$ | $—C(CH_3)_3$ | H | H | H | Cl |
| $CH_3$ | $—(CH_2)_4—CH_3$ | H | H | H | Cl |
| $CH_3$ | $—(CH_2)_5—CH_3$ | H | H | H | Cl |
| $CH_3$ | cyclobutyl | H | H | H | Cl |

-continued

| R¹ | R² | R³ | R⁴ | R⁵ | Y |
|---|---|---|---|---|---|
| CH₃ |  | H | H | H | Cl |
| CH₃ | —CH₂— | H | H | H | Cl |
| CH₃ | —CH₂—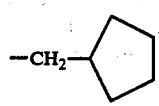 | H | H | H | Cl |
| CH₃ | 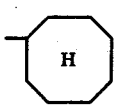 | H | H | H | Cl |
| CH₃ | —CH₂—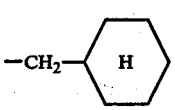 | H | H | H | Cl |
| CH₃ | —(CH₂)₄— | H | H | H | Cl |
| CH₃ | —(CH₂)₂—OCH₃ | H | H | H | Cl |
| CH₃ | —(CH₂)₇—CH₃ | H | H | H | Cl |
| CH₃ | —CH₂—CH=CH₂ | H | H | H | Cl |
| CH₃ | 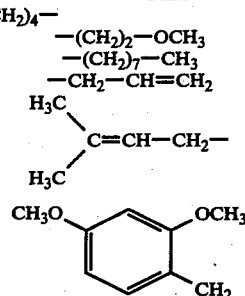 | H | H | H | Cl |
| CH₃ | 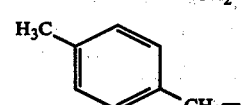 | H | H | H | Cl |
| CH₃ | 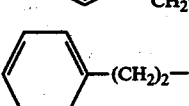 | H | H | H | Cl |
| CH₃ | 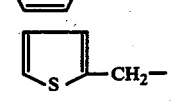—(CH₂)₂— | H | H | H | Cl |
| CH₃ | 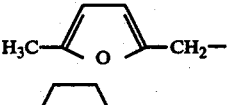—CH₂— | H | H | H | Cl |
| CH₃ | 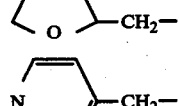—CH₂— | H | H | H | Cl |
| CH₃ | 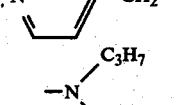—CH₂— | H | H | H | Cl |
| CH₃ | 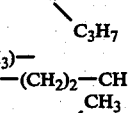—CH₂— | H | H | H | Cl |
| CH₃ | 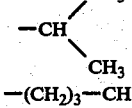 | H | H | H | Cl |
| | —CH₂—CH(CH₃)— | | | | |
| H₅C₂— | —(CH₂)₂—CH₃ | H | H | H | Cl |
| H₅C₂— | —CH(CH₃)CH(CH₃) | H | H | H | Cl |
| H₅C₂— | —(CH₂)₃—CH₃ | H | H | H | Cl |
| H₅C₂— | —CH₂—CH(CH₃)₂ | H | H | H | Cl |
| H₅C₂— |  | H | H | H | Cl |

-continued

| R¹ | R² | R³ | R⁴ | R⁵ | Y |
|---|---|---|---|---|---|
| $H_5C_2-$ |  | H | H | H | Cl |
| $H_5C_2-$ | cyclohexyl-H | H | H | H | Cl |
| $H_5C_2-$ | $-CH_2-$(cyclohexyl-H) | H | H | H | Cl |
| $H_5C_2-$ | $-(CH_2)_2-O-C_2H_5$ | H | H | H | Cl |
| $H_5C_2-$ | $H_3C-CH(-O-CH_3)-CH_2-$ | H | H | H | Cl |
| $H_5C_2-$ | $H_2C=CH-CH_2-$ | H | H | H | Cl |
| $H_5C_2-$ | $H_3C-CH=CH-CH_2-$ | H | H | H | Cl |
| $H_5C_2-$ | (2-Cl-C₆H₄)-CH₂- | H | H | H | Cl |
| $H_5C_2-$ | (4-CH₃O-C₆H₄)-CH₂- | H | H | H | Cl |
| $H_5C_2-$ | (2,3-dihydro-1,4-benzodioxin-6-yl)-CH₂- | H | H | H | Cl |
| $H_5C_2-$ | (2-furyl)-CH₂- | H | H | H | Cl |
| $H_5C_2-$ | (tetrahydrofuran-2-yl)-CH₂- | H | H | H | Cl |
| $H_5C_2-$ | (pyridin-2-yl)-CH₂- | H | H | H | Cl |
| $H_5C_2-$ | $CH_3-CO-N(CH_3)-N(CH_3)-$ | H | H | H | Cl |
| $H_5C_2-$ | $CH_3-CO-NH-$ | H | H | H | Cl |
| $H_3C-(CH_2)_3-$ | $H_3C-(CH_2)_3-$ | H | H | H | Cl |
| $H_3C-(CH_2)_2-$ | $-CH(CH_3)_2$ | H | H | H | Cl |
| $H_3C-(CH_2)_2-$ | $-CH_2-CH(CH_3)_2$ | H | H | H | Cl |
| $CH_3-(CH_2)_2-$ | $-CH(CH_3)-CH_2-CH_3$ | H | H | H | Cl |
| $CH_3-(CH_2)_2-$ | cyclopropyl | H | H | H | Cl |
| $CH_3-(CH_2)_2-$ | cyclopentyl | H | H | H | Cl |
| $CH_3-(CH_2)_2-$ | $H_3C-CH(OCH_3)-CH_2-$ | H | H | H | Cl |
| $CH_3-(CH_2)_2-$ | $CH_2=CH-CH_2-$ | H | H | H | Cl |
| $CH_3-(CH_2)_2-$ | $C_6H_5-CH_2-$ | H | H | H | Cl |
| $CH_3-(CH_2)_2-$ | (2-OCH₃-C₆H₄)-CH₂- | H | H | H | Cl |

-continued

| R¹ | R² | R³ | R⁴ | R⁵ | Y |
|---|---|---|---|---|---|
| CH₃—(CH₂)₂— | furan-2-yl-CH₂— | H | H | H | Cl |
| CH₃—(CH₂)₂— | tetrahydrofuran-2-yl-CH₂— | H | H | H | Cl |
| CH₃—(CH₂)₂— | pyridin-2-yl-CH₂— |  |  |  |  |
| CH₃—(CH₂)₂— | pyridin-3-yl-CH₂— | H | H | H | Cl |
| CH₃—(CH₂)₂— | —N(CH₃)₂ | H | H | H | Cl |
| (CH₂)₃—CH₃ | —CH(CH₃)₃ | H | H | H | Cl |
| (CH₂)₅—CH₃ | —CH(CH₃)₂ | H | H | H | H |
| (CH₃)₂CH—CH₂ | —CH(CH₃)₂ | H | H | H | Cl |
| cyclopropyl | —CH(CH₃)₂ | H | H | H | Cl |
| cyclohexyl-H | —CH(CH₃)₂ | H | H | H | Cl |
| (H₅C₂)₂N— |  |  |  |  |  |
| CH₃(CH₂)₃— | —CH(CH₃)—CH₂—CH₃ | H | H | H | Cl |
| CH₃(CH₂)₃— | —CH₂—CH(CH₃)₂ | H | H | H | Cl |
| CH₃(CH₂)₃— | cyclopropyl | H | H | H | Cl |
| CH₃(CH₂)₃— | cyclopentyl |  |  |  |  |
| CH₃(CH₂)₃— | —CH₂—CH=CH₂ | H | H | H | Cl |
| CH₃(CH₂)₃— | —CH₂—CH=C(CH₃)₂ | H | H | H | Cl |
| CH₃(CH₂)₃— | —CH₂—CH₂—OCH₃ | H | H | H | Cl |
| CH₃—(CH₂)₃— | —C₆H₅—CH₂— | H | H | H | Cl |
| CH₃—(CH₂)₃— | furan-2-yl-CH₂— | H | H | H | Cl |
| CH₃—(CH₂)₃— | pyridin-2-yl-CH₂— | H | H | H | Cl |
| CH₃—(CH₂)₃— | —N(CH₃)₂ | H | H | H | Cl |
| CH₃— | 3,4-dimethoxyphenyl-(CH₂)₂— | H | H | H | Cl |
| CH₃— | 2-chlorophenyl-(CH₂)₂— | H | H | H | Cl |

-continued

| R¹ | R² | R³ | R⁴ | R⁵ | Y |
|---|---|---|---|---|---|
| C₂H₅ | 1,3-benzodioxol-5-yl-(CH₂)₂— | H | H | H | Cl |
| —CH₂—CH(CH₃)₂ | cyclopentyl-CH₂— | H | H | H | Cl |
| CH₃-CH(CH₂-CH₃)— | cyclopropyl | H | H | H | Cl |
| —CH₂—CH(CH₃)₂ | cyclohexyl— | H | H | H | Cl |
| —CH₂—CH(CH₃)₂ | —(CH₂)₂—OCH₃ | H | H | H | Cl |
| —CH₂—CH(CH₃)₂ | —CH₂—CH=C(CH₃)₂ | H | H | H | Cl |
| —CH(CH₃)—CH₂—CH₃ | —CH₂—CH=CH₂ | H | H | H | Cl |
| —CH₂—CH(CH₃)₂ | 4-CH₃O-C₆H₄-CH₂— | H | H | H | Cl |
| —CH₂—CH(CH₃)₂ | furan-2-yl-CH₂— | H | H | H | Cl |
| (CH₃)₂N— | —CH₂—CH(CH₃)₂ | H | H | H | Cl |
| —(CH₂)₅CH₃ | cyclopropyl | H | H | H | Cl |
| cyclopropyl | cyclohexyl— | H | H | H | Cl |
| cyclopropyl | —CH₂—CH=C(CH₃)₂ | H | H | H | Cl |
| cyclopentyl— | cyclohexyl— | H | H | H | Cl |
| CH₂=CH—CH₂— | cyclohexyl— | H | H | H | Cl |
| CH₂=CH—CH(CH₃)— | cyclopentyl— | H | H | H | Cl |
| CH₃O—(CH₂)₂— | cyclohexyl— | H | H | H | Cl |
| (H₃C)₂N— | cyclohexyl— | H | H | H | Cl |
| [CH₃—(CH₂)₃]₂N— | cyclopentyl— | H | H | H | Cl |

-continued

| R¹ | R² | R³ | R⁴ | R⁵ | Y |
|---|---|---|---|---|---|
| CH₂=CH—CH₂— | 4-methoxybenzyl (CH₃O-C₆H₄-CH₂—) | H | H | H | Cl |
| H₃C—CH=CH—CH₂— | 2-pyridylmethyl (pyridine-CH₂—) | H | H | H | Cl |
| (H₃C)₂C=CH—CH₂— | —N(CH₃)₂ | H | H | H | Cl |
| CH₂=CH—CH₂— | 2-furylmethyl (furan-CH₂—) | H | H | H | Cl |
| H₅C₂— | H₅C₂— | H₅C₂— | H | H | Cl |
| CH₃— | —CH(CH₃)₂ | —CH₃ | H | H | Cl |
| H₃C— | cyclopropyl | —C₂H₅ | H | H | Cl |
| (H₃C)₂CH—CH₂— | CH₂=CH—CH₂— | —C₂H₅ | H | H | Cl |
| H₅C₂— | cyclohexyl | —C₂H₅ | H | H | Cl |
| H₃C— | methylcycloheptyl | —CH₃ | H | H | Cl |
| CH₂=CH—CH₂— | —(CH₂)₅—CH₃ | —CH₃ | H | H | Cl |
| H₃C— | 2,4-dimethoxybenzyl (CH₃O-C₆H₃(OCH₃)-CH₂—) | —C₂H₅ | H | H | Cl |
| H₃C— | 2-furylmethyl | —CH₃ | H | H | Cl |
| CH₃— | —CH(CH₃)₂ | C₂H₅— | H | H | Cl |
| CH₃— | —CH₂—CH(CH₃)₂ | —CH₃ | H | H | Cl |
| —N(CH₃)₂ | —N(CH₃)₂ | —C₂H₅ | H | H | Cl |
| —(CH₂)₂— | | —C₂H₅ | H | H | Cl |
| —(CH₂)₄— | | —CH₃ | H | H | Cl |
| —CH₂—C(CH₃)₂— | | —CH₃ | H | H | Cl |
| CH₃— | CH₃— | H | —CH₃ | H | Cl |
| CH₃— | CH₃— | C₂H₅ | —CH₃ | H | Cl |
| CH₃— | —CH(CH₃)₂ | H | —CH₃ | H | Cl |
| CH₃ | —CH₂—CH=CH₂ | H | —(CH₂)₃—CH₃ | H | Cl |
| CH₃ | CH₃ | H | —(CH₂)₅—CH₃ | H | Cl |
| CH₂=CH—CH₂— | —CH₃ | H | —C₂H₅ | H | Cl |
| CH₃— | cyclohexyl | —C₂H₅ | —CH₂—CH(CH₃)₂ | H | Cl |
| CH₃— | cyclopropyl | H | —(CH₂)₃—CH₃ | H | Cl |
| CH₃— | 6-methyl-2-pyridylmethyl | H | —(CH₂)₃—CH₃ | H | Cl |
| CH₃— | —CH₂—CH(OCH₃)— | | | | |

-continued

| R¹ | R² | R³ | R⁴ | R⁵ | Y |
|---|---|---|---|---|---|
| $CH_3-$ | $N(CH_3)_2$ | H | $-(CH_2)_3-CH_3$ | H | Cl |
| $-N(CH_3)_2$ | $-N(CH_3)_2$ | $-C_2H_5$ | $-CH(CH_3)_2$ | H | Cl |
| | $-(CH_2)_2-$ | H | $CH_3-$ | H | Cl |
| | $-(CH_2)_3-$ | H | $-CH(CH_3)_2$ | H | Cl |
| | $-(CH_2)_3-$ | Et | $-(CH_2)_3CH_3$ | H | Cl |
| $CH_3-$ | $CH_3-$ | $CH_3$ | $H_3C-CH-CH_2-$<br>$\quad\quad\quad\; OCH_3$ | H | Cl |
| $CH_3-$ | $(H_3C)_2CH-$ | H | $H_3C-CH-CH_2-$<br>$\quad\quad\quad\; OCH_3$ | H | Cl |
| $CH_3-$ | $-CH_2-CH(CH_3)_2$ | H | $H_5C_2O-(CH_2)_2$ | H | Cl |
| $CH_3-$ | 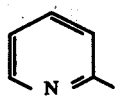 | H | $H_3CO-(CH_2)_2$ | H | Cl |
| $H_5C_2-$ | $H_3C-CH-CH_2-$<br>$\quad\quad\;\, O-CH_3$ | $H_5C_2-$ | $H_3CO-(CH_2)_2-$ | H | Cl |
| $H_2C=CH-CH_2-$ | $-N(CH_3)_2$ | H | $H_3C-O-(CH_2)_3$ | H | Cl |
| $CH_3-$ |  | H | $H_3C-CH-CH_2$<br>$\quad\quad\;\, OCH_3$ | H | Cl |
| $CH_3-$ | 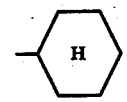 | H | $H_5C_2-O-(CH_2)_2$ | H | Cl |
| $H_3C-$ | $-(CH_2)_2-$ | H | $H_3CO-(CH_2)_2-$ | H | Cl |
| | $-CH(CH_3)_2$ | H | 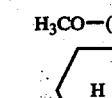 | H | Cl |
| $H_3C-$ | $-CH_2-CH=CH_2$ | H | 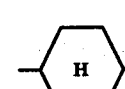 | H | Cl |
| | $-(CH_2)_3-$ | H | 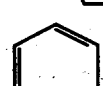 | H | Cl |
| $H_3C$ | $-CH_2-CH(CH_3)_2$ | H | 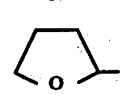 | H | Cl |
| $H_3C-$ | 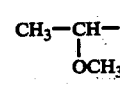 | H | 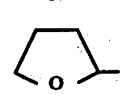 | H | Cl |
| $H_3C-$ |  | H | 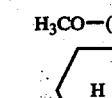 | H | Cl |
| $H_3C-$ |  | $CH_3$ | 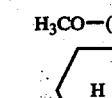 | H | Cl |
| $H_3C-$ | $CH_3-CH-CH_2-$<br>$\quad\quad\;\, OCH_3$ | H | 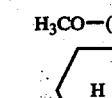 | H | Cl |
| $H_3C-$ | $-N(CH_3)_2$ | H | 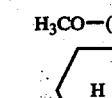 | H | Cl |
| $H_3C-$ | 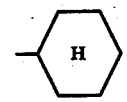 | H | 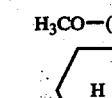 | H | Cl |
| $H_5C_2-$ | $H_5C_2-$ | H | 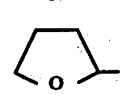 | H | Cl |

| R¹ | R² | R³ | R⁴ | R⁵ | Y |
|---|---|---|---|---|---|
| CH₃— | —CH₂—(cyclohexyl-H) | H | (cyclopropyl) | H | Cl |
| C₂H₅ | C₂H₅— | H | CH₂=CH—CH₂— | H | Cl |
| CH₃— | —CH(CH₃)₂ | H | CH₂=CH—CH₂— | H | Cl |
| CH₃— | (2-pyridyl)—CH₂— | H | CH₂=CH—CH₂— | H | Cl |
| H₅C₂— | CH₃—CH(OCH₃)—CH₂— | —C₂H₅ | CH₂=CH—CH₂— | H | Cl |
| CH₃— | —N(CH₃)₂ | H | CH₂=CH—CH(CH₃)— | H | Cl |
| H₅C₂— | —CH₂—(cyclopropyl) | H | CH₂=CH—CH₂— | H | Cl |
| CH₃— | (cyclopentyl) | H | CH₂=CH—CH₂— | H | Cl |
| CH₃—(CH₂)₃— | CH₃(CH₂)₃— | H | CH₂=CH—CH₂— | H | Cl |
| CH₃— | —CH₃ | H | (H₃C)₂C=CH—CH₂— | H | Cl |
| CH₃— | (2-pyridyl)—CH₂— | H | (H₃C)₂C=CH—CH₂— | H | Cl |
| CH₃— | (phenyl)—CH₂— | H | H₂C=CH—CH₂— | H | Cl |
| CH₃— | (cyclohexyl-H) | H | H₂C=CH—CH₂— | H | Cl |
| CH₃— | (2-furyl)—CH₂— | H | H₂C=CH—CH₂— | H | Cl |
| CH₃— | —CH(CH₃)₂ | H | (phenyl)—CH₂— | H | Cl |
| C₂H₅ | —C₂H₅ | H | (phenyl-H)—CH₂— | Cl | |
| CH₃— | —CH₂—CH(CH₃)₂ | C₂H₅— | (phenyl)—CH₂— | H | Cl |
| CH₃— | —CH(CH₃)₂ | H | 4-F—(phenyl)—CH₂— | H | Cl |
| CH₃— | (cyclohexyl-H) | H | (phenyl)—CH₂— | H | Cl |
| CH₃— | —CH(CH₃)₂ | H | 4-Cl—(phenyl)—CH₂— | H | Cl |

-continued

| R¹ | R² | R³ | R⁴ | R⁵ | Y |
|---|---|---|---|---|---|
| CH₃— | —CH(CH₃)₂ | H | C₆H₅—CH(CH₃)— | H | Cl |
| C₂H₅— | C₂H₅— | H | C₆H₅—CH(CH₃)— | H | Cl |
| H₅C₂— | —CH₂—CH=CH₂ | H | C₆H₅—CH₂— | H | Cl |
| CH₃— | —CH(CH₃)₂ | H | 2-Cl-C₆H₄—CH₂— | H | Cl |
| H₅C₂— | H₅C₂— | H | 2,4-Cl₂-C₆H₃—CH₂— | H | Cl |
| CH₃— | —CH(CH₃)₂ | H | 2,4-Cl₂-C₆H₃—CH₂— | H | Cl |
| CH₃— | —CH₂—CH=CH₂ | H | 4-F-C₆H₄—CH₂— | H | Cl |
| CH₃— | —CH₂—CH=CH₂ | H | 2-Cl-C₆H₄—CH₂— | H | Cl |
| H₅C₂— | cyclohexyl | H | 2-Cl-C₆H₄—CH₂— | H | Cl |
| H₃C— | —N(CH₃)₂ | H | 2-Cl-C₆H₄—CH₂— | H | Cl |
| H₃C— | —CH₂—C₆H₅ | H | 2-Cl-C₆H₄—CH₂— | H | Cl |
| H₃C— | 2-pyridyl-CH₂— | H | 2-CH₃-C₆H₄—CH₂— | H | Cl |
| H₃C— | —CH(CH₃)₂ | H | 4-CH₃-C₆H₄—CH₂— | H | Cl |
| C₂H₅— | 2-pyridyl-CH₂— | H | 2-Cl-C₆H₄—CH₂— | H | Cl |
| H₃C— | —N(CH₃)₂ | CH₃ | C₆H₅—CH₂— | H | Cl |

-continued

| R¹ | R² | R³ | R⁴ | R⁵ | Y |
|---|---|---|---|---|---|
| —(CH₂)₃— | | H | 2-chlorobenzyl | H | Cl |
| H₃C— | —CH(CH₃)₂ | H | 4-bromobenzyl | H | Cl |
| H₃C— | —CH₂—CH(CH₃)₂ | H | 1-(4-chlorophenyl)ethyl | H | Cl |
| H₅C₂— | —CH₂—CH=CH₂ | H | 4-methoxybenzyl | H | Cl |
| CH₃— | —CH₂—CH(CH₃)₂ | H | 4-methoxybenzyl | H | Cl |
| —(CH₂)₂— | | H | 2-methoxybenzyl | H | Cl |
| CH₃— | —CH(CH₃)₂ | H | 2,4-dimethoxybenzyl | H | Cl |
| C₂H₅— | C₂H₅— | C₂H₅ | 2,4-dimethoxybenzyl | H | Cl |
| CH₃— | cyclohexyl | H | 2,4-dimethoxybenzyl | H | Cl |
| —CH₂—CH=CH₂ | —CH₂—CH=CH₂ | H | 2,4-dimethoxybenzyl | H | Cl |
| CH₃— | —CH₂—C₆H₅ | H | 3,4,5-trimethoxybenzyl | H | Cl |
| C₂H₅ | —CH₂-(2-furyl) | H | 3,4,5-trimethoxybenzyl | H | Cl |
| CH₃— | N(CH₃)₂ | H | 2,3,4-trimethoxybenzyl | H | Cl |
| CH₃— | 2-pyridylmethyl | H | 2,3,4-trimethoxybenzyl | H | Cl |

-continued

| R¹ | R² | R³ | R⁴ | R⁵ | Y |
|---|---|---|---|---|---|
| CH₃— | 3-pyridyl-CH₂— | H | 2,4,6-trimethoxybenzyl (3,4,5-trimethoxyphenyl-CH₂—) | H | Cl |
| | —(CH₂)₃— | H | 3,4-dimethoxyphenyl-CH₂— | H | Cl |
| CH₃— | —CH₂-cyclopropyl | H | 3,4-dimethoxyphenyl-CH₂— | H | Cl |
| C₂H₅— | C₂H₅— | H | 2-(n-propoxy)phenyl-CH₂— | H | Cl |
| CH₃— | —CH₂—CH(CH₃)₂ | H | 3,4-methylenedioxyphenyl-CH₂— | H | Cl |
| CH₃— | 2-pyridyl-CH₂— | H | 3,4-methylenedioxyphenyl-CH₂— | H | Cl |
| H₅C₂— | —CH₂—CH=CH₂ | H | 3,4-methylenedioxyphenyl-CH₂— | H | Cl |
| H₅C₂— | 4-pyridyl-CH₂— | H | 3,4-ethylenedioxyphenyl-CH₂— | H | Cl |
| CH₃— | cyclopentyl | H | 3,4-ethylenedioxyphenyl-CH₂— | H | Cl |
| CH₃— | —N(CH₃)₂ | H | 3,4-ethylenedioxyphenyl-CH₂— | H | Cl |
| CH₃— | —CH₂-cyclopropyl | H | 3,4-methylenedioxyphenyl-CH₂— | H | Cl |
| H₅C₂— | —CH₂—C₆H₅ | H | 3,4-methylenedioxyphenyl-CH₂— | H | Cl |
| | —(CH₂)₃— | H | 3,4-methylenedioxyphenyl-CH₂— | H | Cl |

-continued

| R¹ | R² | R³ | R⁴ | R⁵ | Y |
|---|---|---|---|---|---|
| CH₃— | —CH(CH₃)₂ | H | C₆H₅—(CH₂)₂— | H | Cl |
| CH₃— | —CH(CH₃)₂ | C₂H₅ | C₆H₅—(CH₂)₃— | H | Cl |
| C₂H₅— | —CH₂—CH(CH₃)₂ | H | C₆H₅—(CH₂)₂— | H | Cl |
| CH₃— | cyclohexyl-H | CH₃ | C₆H₅—(CH₂)₂— | H | Cl |
| CH₃— | —N(C₂H₅)₂ | H | C₆H₅—(CH₂)₃— | H | Cl |
| CH₂=CH—CH₂— | CH₂=CH—CH₂— | H | C₆H₅—CH(CH₃)—CH₂— | H | Cl |
| CH₃— | —CH(CH₃)₂ | H | C₆H₅—CH(CH₃)—CH₂— | H | Cl |
| C₂H₅— | C₂H₅ | H | C₆H₅—CH₂—CH(CH₃)(H)— | H | Cl |
| CH₃— | 2-pyridyl-CH₂— | H | C₆H₅—(CH₂)₂— | H | Cl |
| CH₃— | —CH₂—CH(CH₃)—O—CH₃ | H | C₆H₅—(CH₂)₂— | H | Cl |
| C₂H₅— | C₂H₅— | H | 2-(C₂H₅)-C₆H₄—CH₂— | H | Cl |
| CH₃— | —CH(CH₃)₂ | CH₃— | 2-Cl-C₆H₄—(CH₂)₂— | H | Cl |
| CH₃— | 2-pyridyl-CH₂— | H | 2,4-Cl₂-C₆H₃—(CH₂)₂— | H | Cl |
| C₂H₅— | CH₂=CH—CH₂— | H | 4-Cl-C₆H₄—(CH₂)₂— | H | Cl |
| CH₃— | 2-furyl-CH₂— | H | 2-Cl-C₆H₄—(CH₂)₂— | H | Cl |

-continued

| R¹ | R² | R³ | R⁴ | R⁵ | Y |
|---|---|---|---|---|---|
| C₂H₅— | C₂H₅— | H | 2-Cl-C₆H₄-CH(CH₃)— | H | Cl |
| CH₃— | —CH(CH₃)₂ | CH₃— | 4-CH₃-C₆H₄-(CH₂)₂— | H | Cl |
| C₂H₅— | C₂H₅— | C₂H₅ | (1,3-benzodioxol-5-yl)-(CH₂)₂— | H | Cl |
| CH₃— | CH(CH₃)₂ | H | (1,4-benzodioxin-6-yl)-(CH₂)₂— | H | Cl |
| C₂H₅— | —CH₂—CH=CH₂ | H | (1,3-benzodioxol-5-yl)-CH(CH₃)— | H | Cl |
| CH₃— | (pyridin-2-yl)-CH₂— | H | (1,4-benzodioxin-6-yl)-(CH₂)₂— | H | Cl |
| C₂H₅— | C₂H₅ | C₂H₅ | furan-2-yl-CH₂— | H | Cl |
| CH₃— | —CH(CH₃)₂ | H | furan-2-yl-CH₂— | H | Cl |
| C₂H₅— | —CH(CH₃)—CH₂—CH₃ | H | furan-2-yl-CH₂— | H | Cl |
| CH₃— | CH₃ | H | 5-CH₃-furan-2-yl-CH₂— | H | Cl |
| CH₃— | —N(CH₃)₂ | H | 5-CH₃-furan-2-yl-CH₂— | H | Cl |
| CH₃— | CH₂=CH—CH₂— | H | furan-2-yl-CH₂— | H | Cl |
| C₂H₅— | (pyridin-2-yl)-CH₂— | H | furan-2-yl-(CH₂)₂— | H | Cl |
| CH₃ | cyclopentyl | H | furan-2-yl-(CH₂)₂— | H | Cl |
| CH₃ | CH₃ | H | thien-2-yl-CH₂— | H | Cl |
| CH₃ | —CH(CH₃)₂ | CH₃ | thien-2-yl-CH₂— | H | Cl |

-continued

| R¹ | R² | R³ | R⁴ | R⁵ | Y |
|---|---|---|---|---|---|
| C₂H₅— | —CH₂—CH(CH₃)₂ | H | 2-thienyl-CH₂— | H | Cl |
| CH₃— | —CH₂-cyclopropyl | H | 2-thienyl-CH₂— | H | Cl |
| CH₃— | cyclohexyl | H | 2-thienyl-CH₂— | H | Cl |
| C₂H₅— | 3-pyridyl-CH₂— | H | 2-thienyl-CH₂— | H | Cl |
| CH₂=CH—CH₂— | —N(C₂H₅)₂ | H | 2-thienyl-CH₂— | H | Cl |
| CH₃— | —CH(CH₃)₂ | H | 2-pyrrolyl-CH₂— | H | Cl |
| CH₃— | 2-pyridyl-CH₂— | H | 2-pyrrolyl-CH₂— | H | Cl |
| CH₂=CH—CH₂— | —N(CH₃)₂ | H | 2-pyrrolyl-CH₂— | H | Cl |
| CH₃— | CH₃— | H | 2-pyridyl-CH₂— | H | Cl |
| C₂H₅— | C₂H₅— | C₂H₅— | 2-pyridyl-CH₂— | H | Cl |
| CH₃— | —CH₂—CH(CH₃)₂ | H | 2-pyridyl-CH₂— | H | Cl |
| C₂H₅— | —CH(CH₃)₂ | H | 2-pyridyl-CH(CH₃)— | H | Cl |
| CH₃— | —N(CH₃)₂ | H | 2-pyridyl-CH(CH₃)— | H | Cl |
| CH₃— | 2-pyridyl-CH₂— | H | 2-pyridyl-CH₂— | H | Cl |
| CH₂=CH—CH₂— | CH₂=CH—CH₂— | CH₃— | 2-pyridyl-CH₂— | H | Cl |

-continued

| R¹ | R² | R³ | R⁴ | R⁵ | Y |
|---|---|---|---|---|---|
| C₂H₅— | furan-2-yl-CH₂— | H | pyridin-2-yl-CH₂— | H | Cl |
| CH₃— | —CH(CH₃)₂ | H | pyridin-2-yl-(CH₂)₂— | H | Cl |
| C₂H₅— | —N(CH₃)₂ | H | pyridin-2-yl-(CH₂)₂— | H | Cl |
| CH₃— | CH₃— | H | pyridin-2-yl-CH(CH₃)— | H | Cl |
| C₂H₅— | CH₃-CH(OCH₃)-CH₂— | H | pyridin-2-yl-CH₂— | H | Cl |
| CH₃— | CH₃— | H | pyridin-3-yl-CH₂— | H | Cl |
| C₂H₅ | C₂H₅ | H | pyridin-3-yl-CH₂— | H | Cl |
| CH₃— | —CH(CH₃)₂ | H | pyridin-3-yl-CH(CH₃)— | H | Cl |
| CH₃ | cyclopentyl | C₂H₅ | pyridin-3-yl-CH₂— | H | Cl |
| C₂H₅— | CH₂=C(cyclopentyl)-CH₂— | CH₃ | pyridin-3-yl-(CH₂)₂— | H | Cl |
| C₂H₅— | pyridin-2-yl-CH₂— | H | pyridin-3-yl-(CH₂)₂— | H | Cl |
| CH₃—(CH₂)₃— | CH₃—(CH₂)₃— | H | pyridin-3-yl-(CH₂)₂— | H | Cl |
| | —(CH₂)₃— | CH₃ | pyridin-2-yl-CH₂— | H | Cl |
| C₂H₅— | cyclopentyl | H | pyridin-2-yl-CH₂— | H | Cl |

-continued

| R¹ | R² | R³ | R⁴ | R⁵ | Y |
|---|---|---|---|---|---|
| $CH_3-$ | $(CH_3)_2C=CH-CH_2-$ | $CH_3$ | 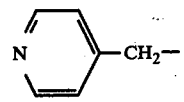 | H | Cl |
| $CH_3-$ | $-CH(CH_3)_2$ | H | 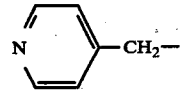 | H | Cl |
| $C_2H_5-$ | $C_2H_5-$ | H | 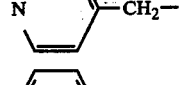 | H | Cl |
| $CH_3-$ |  | H | 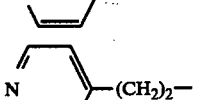 | H | Cl |
| | $-(CH_2)_3-$ | H | 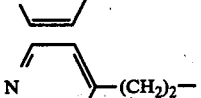 | H | Cl |
| $C_2H_5-$ | $-N(CH_3)_2$ | H | 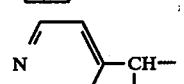 | H | Cl |
| $CH_3-CH_2-CH_2-$ | 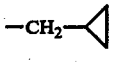 | H | 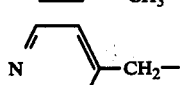 | H | Cl |
| $C_2H_5-$ | 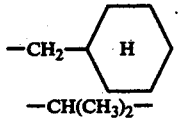 | H |  | H | Cl |
| $CH_3-$ | $-CH(CH_3)_2$ | H | $-(CH_2)_4-$ | | Cl |
| $C_2H_5-$ | $CH_2=CH-CH_2-$ | H | $-(CH_2)_4-$ | | Cl |
| $CH_3-$ | $CH_3-$ | H | $-(CH_2)_4-$ | | Cl |
| $CH_3-$ | $-CH(CH_3)_2$ | H | $-(CH_2)_5-$ | | Cl |
| $C_2H_5-$ | $-N(CH_3)_2$ | H | $-(CH_2)_5-$ | | Cl |
| $C_2H_5$ |  | H | $-(CH_2)_5-$ | | Cl |
| $CH_3-$ | $CH_3-$ | $C_2H_5$ | $-(CH_2)_4-$ | | Cl |
| | $-(CH_2)_3-$ | H | $-(CH_2)_5-$ | | Cl |
| $CH_3$ | $-CH_2-CH(CH_3)_2$ | H | $-(CH_2)-O-(CH_2)_2-$ | | Cl |
| $CH_3-C_2H_5-$ | $C_2H_5-$ | $-(CH_2)_2-O-(CH_2)_2-$ | Cl | | |
| $C_2H_5-$ | 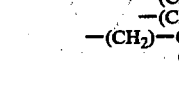 | H | $-(CH_2)_2-O-(CH_2)_2-$ | | Cl |
| $CH_2=CH-CH_2-$ | $-N(CH_3)_2$ | H | $-(CH_2)_2-O-(CH_2)_2-$ | | Cl |
| $C_2H_5-$ |  | H | $-(CH_2)_2-O-(CH_2)_2-$ | | Cl |
| $CH_3-$ | $-CH_2$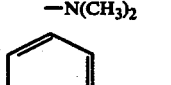 | H | $-(CH_2)_2-O-(CH_2)_2-$ | | Cl |
| $CH_3-$ | $CH_3$ | H | 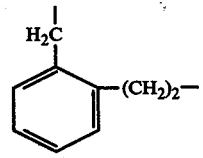 | | Cl |
| $CH_3-$ | $-CH(CH_3)_2$ | $C_2H_5-$ | $CH_3-$ | $CH_3-$ | Cl |
| $CH_3-$ | $CH_3$ | $CH_3-$ | $CH_3-$ | $CH_3-$ | Cl |
| $CH_3-$ | $-CH(CH_3)_2$ | H | $CH_3-$ | $CH_3-$ | Cl |
| $CH_3-$ | $-CH_2-CH(CH_3)_2$ | H | $CH_3-$ | $CH_3-$ | Cl |

-continued

| R¹ | R² | R³ | R⁴ | R⁵ | Y |
|---|---|---|---|---|---|
| C₂H₅— | | H | CH₃— | CH₃— | Cl |
| C₂H₅— | pyridin-2-yl-CH₂— | H | CH₃— | CH₃— | Cl |
| C₂H₅— | furan-2-yl-CH₂— | H | CH₃— | CH₃— | Cl |
| CH₃— | CH₂=CH—CH₂— | H | CH₃— | CH₃— | Cl |
| C₂H₅— | phenyl | H | CH₃— | CH₃— | Cl |
| CH₃— | (tetrahydrofuran-2-yl)-CH₂— | H | CH₃— | CH₃— | Cl |
| CH₃— | —CH₂—phenyl | H | CH₃— | CH₃— | Cl |
| C₂H₅— | —N(C₂H₅)₂ | H | CH₃— | CH₃— | Cl |
| CH₃— | —N(CH₃)₂ | H | CH₃— | CH₃— | Cl |
| CH₃— | cyclohexyl | H | CH₃— | CH₃— | Cl |
| C₂H₅— | —CH₂-cyclopropyl | H | CH₃— | CH₃— | Cl |
| CH₃— | —CH₂-cyclopentyl | H | CH₃— | CH₃— | Cl |
| C₂H₅— | pyridin-3-yl-CH₂— | H | CH₃— | CH₃— | Cl |
| CH₃— | CH₃O—(CH₂)₂ | H | CH₃— | CH₃— | Cl |
| C₂H₅— | CH₃OCH(CH₃)—CH₂— | H | CH₃— | CH₃— | Cl |
| —(CH₂)₃CH₃ | —CH₂-cyclopropyl | H | C₂H₅— | C₂H₅— | Cl |
| C₂H₅— | cyclopentyl | H | C₂H₅— | C₂H₅— | Cl |
| C₂H₅— | CH₂=CH—CH₂— | H | CH₃— | C₂H₅— | Cl |
| CH₃— | pyridin-2-yl-CH₂— | H | CH₃— | C₂H₅— | Cl |
| CH₃— | 2-hydroxyphenyl | H | CH₃— | —(CH₂)₃—CH₃ | Cl |
| CH₃ | —CH(CH₃)₂ | CH₃ | CH₃— | —(CH₂)₃—CH₃ | Cl |
| CH₂=CH—CH₂— | —N(CH₃)₂ | H | CH₃— | —(CH₂)₃—CH₃ | Cl |
| CH₃— | CH₃OCH(CH₃)—CH₂— | H | CH₃— | —CH(CH₃)₂ | Cl |
| CH₃— | furan-2-yl-CH₂— | H | CH₃— | —CH(CH₃)₃ | Cl |

-continued

| R¹ | R² | R³ | R⁴ | R⁵ | Y |
|---|---|---|---|---|---|
| CH₃— | —CH(CH₃)—CH₂—CH₃ | H | C₂H₅— | —CH₂—CH(CH₃)₃ | Cl |
|  |  | —CH₃ | C₂H₅— | —CH₂—CH(CH₃)₃ | Cl |
| —CH₃ | —CH(CH₃)₂ | H | —(CH₂)₃—CH₃ | —(CH₂)₃—CH₃ | Cl |
| CH₃— | CH₂=CH—CH₂— | H | —(CH₂)₃—CH₃ | —(CH₂)₃—CH₃ | Cl |
| CH₃— | —N(CH₃)₂ | H | —(CH₂)₃—CH₃ | —(CH₂)₃—CH₃ | Cl |
| CH₃— | CH₃— | H | CH₃O—(CH₂)₂— | —CH₃ | Cl |
| CH₃— | —CH(CH₃)₂ | H |  | CH₃ | Cl |
| CH₃— | CH₂=CH—CH₂— | H |  | CH₃ | Cl |
| CH₃— |  | H |  | CH₃ | Cl |
| C₂H₅— | C₂H₅ | H | CH₂=CH—CH₂— | CH₃ | Cl |
| CH₃— | —CH(CH₃)₂ | H |  | CH₃ | Cl |
| CH₃— | —CH₂— | H |  | CH₃ | Cl |
| —(CH₂)₃—CH₃ | —N(CH₃)₂ | H |  | (CH₂)₂CH₃ | Cl |
| C₂H₅— | C₂H₅ | H |  | CH₃ | Cl |
| CH₃— | CH₂=CH—CH₂— | H |  | CH₃ | Cl |
| CH₃ | CH(CH₃)₂ | H |  | CH₃ | Cl |
| —(CH₂)₃—CH₃ |  | H |  | CH₃ | Cl |
| CH₃— |  | H |  | CH₃ | Cl |
| | —(CH₂)₂— | H |  | CH₃ | Cl |
| C₂H₅— |  | H |  | —CH₂—CH₃ | Cl |

-continued

| R¹ | R² | R³ | R⁴ | R⁵ | Y |
|---|---|---|---|---|---|
| CH₃ | —CH₂—CH(CH₃)₂ | H | benzodioxole-CH₂— | CH₃ | Cl |
| CH₂=CH—CH₂— | cyclopropyl | H | benzodioxole-CH₂— | CH₃ | Cl |
| CH₃— | 2-pyridyl(C₂H₅)-CH₂— | H | benzodioxole-CH₂— | (CH₂)₃CH₃ | Cl |
| C₂H₅— | H | 3,4-(CH₃O)₂-C₆H₃-CH₂— | CH₃ | Cl |
| C₂H₅— | C₂H₅— | H | 2-furyl-CH₂— | —CH₃ | Cl |
| CH₃ | CH₂=CH—CH₂— | H | 2-furyl-CH₂— | —CH₃ | Cl |
| CH₃— | 2-pyridyl-CH₂— | H | 2-furyl-CH₂ | —(CH₂)₃CH₃ | Cl |
| CH₃— | —CH(CH₃)₂ | H | 2-pyridyl-CH₂— | CH₃ | CL |
| CH₂H₅— | 2-methylcyclohexyl | H | | | |
| 2-pyridyl-CH₂— CH₃— | CH₂=CH—CH₂— | CH₃ Cl | 3-pyridyl-CH₂— | CH₃ | Cl |
| CH₃— | 2-pyridyl-CH₂— | H | 3-pyridyl-CH₂— | CH₃ | Cl |
| CH₃— | —N(CH₃)₂ | H | 2-pyridyl-CH₂— | (CH₂)₂CH₃ | CL |
| C₂H₅— | —CH₂-cyclopropyl | H | 2-pyridyl-CH₂— | (CH₂)₃CH₃ | Cl |
| CH₃— | CH₃— | H | H | H | F |
| C₂H₅— | —CH(CH₃)₃ | H | H | H | F |
| CH₃— | C₂H₅— | C₂H₅ | H | H | F |
| C₂H₅— | CH₂=CH—CH₂— | H | H | H | F |
| CH₃— | | H | H | H | F |
| —CH₂—CH₂—CH₃ | —CH₂-cyclopropyl | H | H | H | F |
| C₂H₅— | 2-cyclopentyl | CH₃ | H | H | F |
| CH₃— | —N(CH₃)₂ | H | H | H | F |

-continued

| R¹ | R² | R³ | R⁴ | R⁵ | Y |
|---|---|---|---|---|---|
| C₂H₅— | 2-pyridyl-CH₂— | H | H | H | F |
| CH₃— | 2-furyl-CH₂— | H | H | H | F |
| C₂H₅— | C₆H₅—CH₂— | H | H | H | F |
| CH₃— | —CH(CH₃)₂ | H | 2-Cl-C₆H₄-CH₂— | H | F |
| C₂H₅— | C₂H₅— | C₂H₅ | CH₃— | H | F |
| CH₃— | 2-pyridyl-CH₂— | H | C₄H₉— | H | F |
| CH₃— | CH₂=CH—CH₂— | H | CH₃— | CH₃— | F |
| CH₃— | cyclopentyl— | H | CH₃— | CH₃— | F |
| CH₃— | —CH(CH₃)₂ | C₂H₅ | C₆H₅—CH₂— | CH₃— | F |
| CH₃— | —CH(CH₃)—CH₂—CH₃ | H | C₆H₅—CH₂— | CH₃— | F |
| C₂H₅— | CH₃—CH(OCH₃)—CH₂— | H | C₆H₅—CH₂— | CH₃— | F |
| CH₃— | —N(CH₃)₂ | H | 2,4-(CH₃O)₂-C₆H₃-CH₂— | CH₂—CH₃— | F |
| C₂H₅— | C₂H₅ | H | C₆H₅—(CH₂)₂— | CH₃— | F |
| CH₃— | —CH(CH₃)₃ | H | 3,4-methylenedioxy-C₆H₃-CH₂— | CH₃— | F |
| —CH₃— | —CH₃— | H | H | H | Br |
| CH₃— | CH₃— | —C₂H₅ | H | H | Br |
| —CH₃ | —CH(CH₃)₂ | CH₃ | H | H | Br |
| —CH₃ | —CH(CH₃)₂ | H | H | H | Br |
| —C₂H₅ | —CH₂—CH(CH₃)₂ | H | H | H | Br |
| CH₃— | cyclohexyl— | H | H | H | Br |
| C₂H₅— | 2-pyridyl-CH₂— | H | H | H | Br |
| C₂H₅— | CH₂=CH—CH₂— | H | H | H | Br |
| C₂H₅— | —N(CH₃)₂ | H | H | H | Br |
| C₂H₅— | —CH₂-cyclopentyl | H | H | H | Br |

-continued

| R¹ | R² | R³ | R⁴ | R⁵ | Y |
|---|---|---|---|---|---|
| CH₃— | cyclopropyl | H | H | H | Br |
| CH₃— | —CH(CH₃)₂ | H | CH₃— | H | Br |
| CH₃—(CH₂)₃— | —CH(CH₃)₂ | H | CH₃— | H | Br |
| CH₃— | CH₂=CH—CH₂— | H | CH₃—(CH₂)₄— | H | Br |
| C₂H₅— | 2-pyridylmethyl (pyridin-2-yl-CH₂—) | H | CH₃—(CH₂)₄— | H | Br |
| CH₃— | cyclohexylmethyl | CH₃ | C₂H₅— | H | Br |
| CH₃— | cyclohexyl | H | CH₃—(CH₂)₃— | H | Br |
| C₂H₅— | C₂H₅— | H | (CH₃)₂CH— | H | Br |
| CH₃— | —CH(CH₃)₂ | H | 2-chlorobenzyl | H | Br |
| CH₃— | cyclopentyl | H | 2-chlorobenzyl | H | Br |
| CH₃— | —CH(CH₃)₂ | H | —(CH₂)₂—phenyl | H | Br |
| C₂H₅— | C₂H₅— | H | 2,4-dimethoxybenzyl | H | Br |
| CH₃— | —CH(CH₃)₂ | H | benzyl (—CH₂—phenyl) | CH₃— | Br |
| CH₃— | —CH₂—CH(CH₃)₂ | H | CH₃— | CH₃— | Br |
| CH₂=CH—CH₂— | cyclopropylmethyl | H | CH₃— | CH₃— | Br |
| CH₃— | 2-pyridylmethyl | H | CH₃— | CH₃— | Br |
| CH₃— | CH₃— | H | H | H | CF₃ |
| CH₃— | CH₃— | C₂H₅— | H | H | CF₃ |
| CH₃— | —CH(CH₃)₂ | H | H | H | CF₃ |
| —C₂H₅ | —C₂H₅ | H | H | H | CF₃ |
| CH₃— | CH₃—(CH₂)₄— | H | H | H | CF₃ |
| cyclopropyl | cyclopropylmethyl | CH₃— | H | H | CF₃ |
| C₂H₅— | cyclopentyl | H | H | H | CF₃ |
| CH₃— | cyclohexyl | H | H | H | CF₃ |
| CH₃—CH₂—CH₂— | —CH₂—cyclopropyl | H | H | H | CF₃ |
| CH₃— | —(CH₂)₃— | H | H | H | CF₃ |
| C₂H₅— | CH₂=CH—CH₂— | H | H | H | CF₃ |
| | —N(CH₃)₂ | H | H | H | CF₃ |

-continued

| R¹ | R² | R³ | R⁴ | R⁵ | Y |
|---|---|---|---|---|---|
| CH₃— | —CH₂—C₆H₅ | H | H | H | CF₃ |
| CH₃— | 2-pyridyl-CH₂— | H | H | H | CF₃ |
| C₂H₅— | 2-furyl-CH₂— | CH₃ | H | H | CF₃ |
| CH₃— | CH₃—CH(OCH₃)—CH₂— | H | H | H | CF₃ |
| —(CH₂)₂—CH₃ | —(CH₂)₂—CH₃ | H | H | H | CF₃ |
| C₂H₅— | 3-pyridyl-CH₂— | C₂H₅ | H | H | CF₃ |
| CH₃— | CH₃ | C₂H₅ | —CH₃ | H | CF₃ |
| CH₃— | —CH(CH₃)₂ | H | —(CH₂)₃—CH₃ | H | CF₃ |
| C₂H₅— | C₂H₅— | H | —C₂H₅ | H | CF₃ |
| CH₃(CH₂)₃— | CH₃—(CH₂)₃— | H | —CH₂—CH₂—CH₃ | H | CF₃ |
| CH₃ | cyclohexyl | H | —CH₃ | H | CF₃ |
| C₂H₅— | —CH₂—cyclopropyl | H | —(CH₂)₃—CH₃ | H | CF₃ |
| CH₃— | —CH₂—C₆H₅ | H | —CH(CH₃)₂ | H | CF₃ |
| CH₃— | 2-pyridyl-CH₂— | H | —CH(CH₃)₂ | H | CF₃ |
| C₂H₅— | CH₂=CH—CH₂— | H | —C₂H₅ | H | CF₃ |
| CH₃— | —N(CH₃)₂ | H | —C₂H₅ | H | CF₃ |
| CH₃— | —CH(CH₃)₂ | H | cyclopentyl | H | CF₃ |
| C₂H₅— | C₂H₅— | C₂H₅— | cyclopentyl | H | CF₃ |
| CH₃ | cyclopentyl | H | cyclohexyl | CH₃ | CF₃ |
| CH₃— | CH₃— | H | —(CH₂)₃—CH₃ | cyclohexyl | CF₃ |
| CH₃— | CH₂=CH—CH₂— | H | cyclohexyl | H | CF₃ |
| CH₃— | —CH₂—CH(CH₃)₂ | H | cyclohexyl-CH₂— | H | CF₃ |

-continued

| R¹ | R² | R³ | R⁴ | R⁵ | Y |
|---|---|---|---|---|---|
| | —(CH₂)₃— | CH₃— | cyclohexyl-CH₂— | C₂H₅ | CF₃ |
| CH₃— | 3-pyridyl-CH₂— | H | cyclopentyl- | H | CF₃ |
| CH₃— | —CH(CH₃)₂ | H | 2-Cl-C₆H₄-CH₂— | H | CF₃ |
| C₂H₅— | CH₂=CH—CH₂— | H | 2-Cl-C₆H₄-CH₂— | H | CF₃ |
| C₂H₅— | —C₂H₅ | H | C₆H₅-(CH₂)₂— | H | CF₃ |
| CH₃— | —CH₂—CH(CH₃)₂ | H | 2,4-(CH₃O)₂-C₆H₃-CH₂— | H | CF₃ |
| C₂H₅— | cyclopentyl- | H | 3,4-(CH₃O)₂-C₆H₃-CH₂— | H | CF₃ |
| C₂H₅— | 2-furyl-CH₂— | H | 3,4-(CH₃O)₂-C₆H₃-CH₂— | H | CF₃ |
| C₂H₅— | 2-pyridyl-CH₂— | H | 3,4-methylenedioxy-C₆H₃-CH₂— | H | CF₃ |
| CH₃— | —CH(CH₃)₂ | H | 3,4-methylenedioxy-C₆H₃-CH₂— | H | CF₃ |
| CH₃— | —CH₃ | H | C₆H₅-CH₂— | —CH₃ | CF₃ |
| C₂H₅— | —C₂H₅ | H | C₆H₅-CH₂— | —(CH₂)₃CH₃ | CF₃ |
| CH₃— | —CH(CH₃)—CH₂—CH₃ | H | C₆H₅-CH₂— | —CH(CH₃)₂ | CF₃ |
| C₂H₅— | —C₂H₅ | H | CH₃— | —CH₃ | CF₃ |
| CH₃— | —CH₂—CH(CH₃)₂ | H | CH₃— | —CH₃ | CF₃ |
| CH₃— | cyclopentyl- | H | CH₃— | —CH₃ | CF₃ |
| CH₃— | 2-pyridyl-CH₂— | CH₃— | CH₃— | —CH₃ | CF₃ |
| | —(CH₂)₂— | H | CH₃— | —CH₃ | CF₃ |

-continued

| R¹ | R² | R³ | R⁴ | R⁵ | Y |
|---|---|---|---|---|---|
| CH₃— | CH₃— | H | 2-Cl-C₆H₄-CH₂— | H | CF₃ |
| CH₃ | CH₃— | H | 2,4-(CH₃O)₂-C₆H₃-CH₂— | H | CF₃ |
| CH₃— | —CH₃ | H | H | H | CH₃ |
| CH₃— | —CH₃ | C₂H₅— | H | H | CH₃ |
| CH₃— | CH₃—(CH₂)₅— | H | H | H | CH₃ |
| C₂H₅— | H | H | H | H | CH₃ |
| CH₃— | —CH₂-cyclopropyl | H | H | H | CH₃ |
| | cyclohexyl | | | | |
| C₂H₅— | CH₂=CH—CH₂— | H | H | H | CH₃ |
| | —(CH₂)₃— | H | H | H | OH |
| C₂H₅— | 2-pyridyl-CH₂— | H | H | H | CH₃ |
| CH₃— | 2-furyl-CH₂— | H | H | H | CH₃ |
| C₂H₅— | 2-tetrahydrofuryl-CH₂— | CH₃— | H | H | CH₃ |
| CH₃— | —CH₂-C₆H₅ | H | H | H | CH₃ |
| C₂H₅— | —N(CH₃)₂ | C₂H₅— | H | H | CH₃ |
| CH₃— | H₃C-CH(OCH₃)-CH₂— | H | H | H | CH₃ |
| CH₃— | 3-pyridyl-CH₂— | CH₃— | H | H | CH₃ |
| CH₃— | CH₃— | C₂H₅— | —C₂H₅ | H | CH₃ |
| CH₃— | —CH(CH₃)₂ | H | —(CH₂)₃—CH₃ | H | CH₃ |
| C₂H₅— | CH₃-CH-CH₂-CH₃ | H | —CH₂—CH₂—CH₃ | H | CH₃ |
| CH₃— | cyclohexyl | H | —(CH₂)₃CH₃ | H | CH₃ |
| CH₃— | —CH(CH₃)₂ | H | —CH₂—CH(CH₃)₂ | H | CH₃ |
| C₂H₅— | —CH₂—CH(CH₃)₂ | H | cyclohexyl | H | CH₃ |
| CH₃— | CH₂=CH—CH₂— | CH₃— | cyclohexyl | H | CH₃ |
| CH₃— | —CH(CH₃)₂ | H | cyclohexyl-CH₂— | H | CH₃ |

-continued

| R¹ | R² | R³ | R⁴ | R⁵ | Y |
|---|---|---|---|---|---|
| C₂H₅— | 2-pyridyl-CH₂— | H | cyclohexyl-CH< (H) | H | CH₃ |
| C₂H₅— | CH₂=CH—CH₂— | H | 2-Cl-C₆H₄-CH₂— | H | CH₃ |
| C₂H₅— | cyclopentyl-H | H | 2-Cl-C₆H₄-CH₂— | H | CH₃ |
| CH₃— | CH₃-CH(—)-CH₂-CH₃ | H | C₆H₅-CH(CH₃)— | H | CH₃ |
| CH₃— | —N(CH₃)₂ | H | C₆H₅-(CH₂)₂— | H | CH₃ |
| CH₃— | CH₃— | CH₃— | 2,4-(CH₃O)₂-C₆H₃-CH₂— | H | CH₃ |
| CH₃— | —CH₂—CH(CH₃)₂ | H | 2,4-(CH₃O)₂-C₆H₃-CH₂— | H | CH₃ |
| C₂H₅— | CH₂=CH—CH₂— | H | 2,4-(CH₃O)₂-C₆H₃-CH₂— | H | CH₃ |
| C₂H₅— | cyclopentyl-H | H | 3,4-(CH₃O)₂-C₆H₃-CH₂— | H | CH₃ |
| CH₂=CH—CH₂— | 2-pyridyl-CH₂— | H | 3,4-(CH₃O)₂-C₆H₃-CH₂— | H | CH₃ |
| C₂H₅— | C₂H₅— | CH₃— | 3,4-methylenedioxy-C₆H₃-CH₂— | H | CH₃ |
| CH₃— | —CH(CH₃)₂ | H | 3,4-methylenedioxy-C₆H₃-CH₂— | H | CH₃ |
| C₂H₅— | —CH₂—CH=CH₂ | H | 3,4-ethylenedioxy-C₆H₃-CH₂— | H | CH₃ |

-continued

| R¹ | R² | R³ | R⁴ | R⁵ | Y |
|---|---|---|---|---|---|
| C₂H₅ | —CH(CH₃)₂ | H | benzyl (C₆H₅—CH₂—) | CH₃— | CH₃ |
| CH₃— | CH₂=CH₂—CH₂— | H | benzyl (C₆H₅—CH₂—) | —CH₃ | CH₃ |
| CH₃— | —CH(CH₃)₂ | H | 3,4-methylenedioxybenzyl | —(CH₂)₃—CH₃ | CH₃ |
| CH₃— | CH₃— | H | CH₃— | CH₃— | CH₃ |
| C₂H₅— | —CH₂—CH(CH₃)₂ | H | CH₃— | CH₃— | CH₃ |
| C₂H₅— | C₂H₅— | CH₃— | CH₃— | CH₃— | CH₃ |
| CH₃ | (CH₂)₂OCH₃ | H | H | H | Cl |
| C₂H₅ | (CH₂)₂OCH₃ | H | H | H | Cl |
| CH₃ | (CH₂)₂OCH₃ | H | n-C₃H₇— | H | Cl |
| CH₃ | (CH₂)₂OCH₃ | H | H | H | Br |
| CH₃ | (CH₂)₃OCH₃ | H | H | H | Cl |
| CH₃ | (CH₂)₂OC₂H₅ | H | H | H | Cl |
| n-C₃H₇ | (CH₂)₂OC₂H₅ | H | H | H | Cl |
| C₂H₅ | CH₂—CH—CH₃<br>\|<br>OCH₃ | H | H | H | Cl |
| C₂H₅ | CH₂—CH—CH₃<br>\|<br>O—C₂H₅ | H | H | H | Cl |
| CH₃ | CH₂—CH—C₂H₅<br>\|<br>OCH₃ | H | H | H | Cl |
| CH₃ | CH₂—CH—C₂H₅<br>\|<br>OCH₃ | H | n-C₃H₇ | H | Cl |
| C₂H₅ | CH₂—CH—C₂H₅<br>\|<br>O—C₂H₅ | H | H | H | Cl |
| CH₃ | CH₂—CH—C₂H₅<br>\|<br>O—C₂H₅ | H | CH₂—C₆H₅ | H | Cl |
| CH₃ | CH₂—CH—C₂H₅<br>\|<br>O—C₂H₅ | H | H | H | Br |

The products of the invention are valuable medicaments and are distinguished by a very good diuretical and saluretical activity. 4-aryl-1,3-thiazolidine-4-ol-derivatives having an anorectic, diuretic acitivity stimulating the CNS are known from German Offenlegungsschrift No. 1,938,674 or U.S. Pat. No. 3,671,534, these compounds have no sulfonamide groups on the aromatic nucleus and their diuretic action depends to a high degree on a specific substitution of the thiazolidine ring. It was surprising that the new products of the instant invention have a high salidiuretic activity independent of that specific ring substitution by the introduction of a sulfonamide group in 3-position of the benzene nucleus, which are distinctly superior in quality and quantity to these known thiazolidine derivatives. Moreover, the anorectic and CNS-stimulating action less desired is largely oppressed.

The salidiuretic activity of the new products of the invention was determined on the rat in a dosage unit of 50 mg/kg per os. They are superior to the salidiuretic activity of known commercial products of the thiazide group, for example the hydrochlorothiazide and that of the chlorothalidone. Moreover, the products of the invention are distinguished by a long-lasting activity which is about the same as that of chlorothalidone. For this reason, the products of the invention are especially suitable for the treatment of hypertonic states, on human beings in which case they can be combined, as it is generally usual, nowadays, optionally with an antihypertonic agent.

Suitable therapeutic administration forms are, above all, tablets, dragees, capsules, suppositories and ampoules for parenteral administration (intravenous, subcutaneous and intramuscular). The products of the invention are contained in these administration forms preferably in the form of their acid addition products. The therapeutical dosage unit is between 5 and 500 mg, preferably 10–100 mg. These composition may contain especially for the treatment of high blood pressure on human beings, in addition to the usual expedients an antihypertensive agent, for example, reserpin, hydralazin, guanethidin, -methyldopa or clonidin.

Moreover, therapeutical combination preparations with potassium retaining compounds, such as aldosteronantagonists, for example spironolacton, or pseudoaldosteronantagonists, such as triamterene or amiloride are convenient, furthermore, K⁺-substitution in various application forms, such as dragees, tablets, effervescent tablets, juices and others.

The following Examples illustrate the invention, the melting and decomposition points are not corrected. The IR-spectra were taken in KBr, the indicated IR-spectroscopic data are taken from routine spectra and are also not corrected.

EXAMPLE 1

4-(4-Chloro-3-sulfamoylphenyl)-3-methyl-2-methylimino-1,3-thiazolidine-4-ol-hydrobromide (a) 4.7 g of 4'-chloro-3'-sulfamoylacetophenone were suspended in 50 ml of ethyl acetate and to that suspension, some drops of a solution of 3.2 g of bromine were added until the mixture was distinctly brown. The suspension was heated to about 60°–70° C. until the color changed (addition of a drop of 48% hydrobromic acid possible), cooled and the residual amount of the bromine solution was added dropwise at room temperature, while stirring. After distilling off the solvent, 2-bromo-4'-chloro-3'-sulfamoylacetophenone was obtained which melted at 169° C. (from n-butanol).

(b) The residue was dissolved in 70 ml of acetone without further isolating the 2-bromo-4'-chloro-3'-sulfamoylacetophenone to which solution 2.1 g of 1,3-dimethylthiourea were added. Shortly thereafter, the oily 4-(4-chloro-3-sulfamoylphenyl)-3-methyl-2-methylimino-1,3-thiazolidine-4-ol-hydrobromide was separated and crystallized upon heating the reaction mixture to 40° C., forming colorless crystals that melted at 218°–219° C. (decomposition).

EXAMPLE 2

4-(4-Chloro-3-sulfamoylphenyl)-3-methyl-2-methylimino-1,3-thiazolidine-4-ol (a) 4-(4-Chloro-3-chlorosulfonylphenyl-3-methyl-2-methylimino-1,3-thiazolidine-4-ol-hydrobromide. 5.1 g of 4'-chloro-3'-chlorosulfonyl-acetophenone were reacted in the manner described in Example 1(a) with 3.2 g bromine in ethyl acetate to yield the 2-bromo-4'-chlorosulfonylacetophenone (melting point: 111° C. from chloroform, $\bar{\gamma}C=O$ 1700 cm$^{-1}$) which was reacted without further isolation, as described in Example 1(b) with 2.1 g of 1,3-dimethylthiourea in 50 ml of acetone. The mixture was stirred for 30 minutes at 30°–35° C., cooled to 10° C. and the 4-(4-chloro-3-chlorosulfonylphenyl)-3-methyl-2-methylimino-1,3-thazolidine-4-ol-hydrobromide was filtered. Colorless crystals melting at 162° C. (decomposition).

(b) 4.4 g of 4-(4-chloro-3-chlorosulfonylphenyl)-3-methyl-2-methylimino-1,3-thiazolidine-4-ol-hydrobromide were introduced portionwise, while stirring, into 30 ml of a 8% methanolic ammonia solution. The mixture was allowed to dwell over night at room temperature, the precipitate of (4(4-chloro-3-sulfamoylphenyl)-3-methyl-2-methylimino-1,3-thiazolidine-4-ol) was filtered and washed several times with water. Colorless crystals were obtained which melted at 188° C. (decomposition), $\bar{\gamma}C=N$ 1620 cm$^{-1}$.

(c) 10 g of powdered 4-(4-chloro-3-sulfamoylphenyl)-3-methyl-2-methylimino-1,3-thiazolidine-4-ol-hydrobromide were dissolved in 500 ml of water at 50° C., while stirring, 100 ml of saturated sodium bicarbonate solution were added and the solution was thoroughly stirred for 2 hours at 5°–10° C., 4-(4-chloro-3-sulfamoylphenyl)-3-methyl-2-methylimino-1,3-thiazolidine-4-ol was filtered off and washed several times with water. Melting point: 187°–188° C. (decomposition).

EXAMPLE 3

4-(4-Chloro-3-sulfamoylphenyl)-3-methyl-2-methylimino-1,3-thiazolidine-4-ol-hydrochloride (a) 20 g of 4'-chloro-3'-sulfamoyl-diazoacetophenone were introduced, portionwise, while cooling and stirring, into a mixture of 200 ml of diethyleneglycol dimethyl ether. 2,4'-dichloro-3'-sulfamoylacetophenone was precipitated (melting point: 179° C.) with 1 liter of ice water.

5.3 g of 2,4'-dichloro-3'-sulfamoylacetophenone were suspended in 35 ml of methanol to which 2.1 g of 1,3-dimethylthiourea were added. The mixture was stirred for 30 minutes at 40° C., cooled to 5° C. and 4-(4-chloro-3-sulfamoylphenyl)-3-methyl-2-methylimino-1,3-thiazolidine-4-ol-hydrochloride was filtered off.

(b) 3 g of 4'-chloro-3'-sulfamoyl-2-hydroxyacetophenone were boiled under reflux for 2 hours in 30 ml of thionylchloride and the thionyl chloride was distilled off. The residue was treated with 20 ml of 80% methanol while cooling (heavy reaction), the solvent was expelled under reduced pressure and the residue was reacted without isolating the 2,4'-dichloro-3'-sulfamoylacetophenone in 20 ml of acetone with 1.7 g of 1,3-dimethylthiourea, as has been described in Example 3(a).

4-(4-Chloro-3-sulfamoylphenyl)-3-methyl-2-methylimino-1,3-thiazolidine-4-ol-hydrochloride precipitated and was filtered off.

(c) 10 g of 4-(4-chloro-3-sulfamoylphenyl)-3-methyl-2-methylimino-1,3-thiazolidine-4-ol were suspended in 50 ml of ethanol to which suspension a 15% ethanolic hydrochloric acid solution was rapidly added dropwise, while stirring and cooling with ice, until the test paper showed a heavy acid reaction. The reaction temperature should not be exceeded. After shortly clearing the mixture, 4-(4-chloro-3-sulfamoylphenyl)-3-methyl-2-methylimino-1,3-thiazolidine-4-ol-hydrochloride precipitated Stirring was continued for 10 minutes, 30 ml of ethyl acetate were added, the mixture was stirred for another 10 minutes at room temperature and the crystals were filtered off. They were colorless and melted at 210° C. (decomposition).

EXAMPLE 4

4(4-Chloro-3-sulfamoylphenyl)-3-methyl-2-methylimino-1,3-thiazolidine-4-ol-p-toluenesulfonate 1 g of p-toluene sulfonic acid was added to a suspension of 1.5 g of 4-(4-chloro-3-sulfamoylphenyl)-3-methyl-2-methylimino-1,3-thiazolidine-4-ol in 10 ml of ethanol. The clear solution was poured into 60 ml of diisopropyl ether and the oil so obtained was crystallized by treating with diethyl ether. Colorless crystals were obtained which were decomposed from 94° C. onwards.

EXAMPLE 5

4-(4-Chloro-3-sulfamoylphenyl)-3-methyl-2-methylimino-1,3-thiazolidine-4-ol-methansulfonate 1.5 g of 4-(4-chloro-3-sulfamoylphenyl)-3-methyl-2-methyl imino-1,3-thiazolidine-4-ol were reacted in 10 ml of ethanol with 0.5 g of methanesulfonic acid and the colorless crystals were filtered off after stirring for 3 hours. Melting point: 168° C. (decomposition).

EXAMPLE 6

4-(4-Chloro-3-sulfamoylphenyl)-3-methyl-2-methylimino-1,3-thiazolidine-4-ol-amidosulfonate 4.5 g of 4-(4-chloro-3-sulfamoylphenyl)-3-methyl-2-methylimino-1,3-thiazolidine-4-ol were reacted with 1.5 g of ground amidosulfonic acid in 70 ml of ethanol. After 1 hour at 50° C. and subsequent stirring for 10 hours at room temperature the desired salt precipitated in the form of colorless crystals which melted at 171° C.

EXAMPLE 7

4-(4-Chloro-3-sulfamoylphenyl)-3-methyl-2-methylimino-1,3-thiazolidine-4-ol-formiate According to the method of Example 5 there was obtained from 1.5 g of 4-(4-chloro-3-sulfamoylphenyl)-3-methyl-2-methylimino-1,3-thiazolidine-4-ol and 0.25 g of formic acid the desired formate in the form of colorless crystals which melted at 154° C. (decomposition).

EXAMPLE 8

4-(4-Chloro-3-sulfamoylphenyl)-3-methyl-2-methylimino-1,3-thiazolidine-4-ol-lactate To 1.5 g of 4-(4-chloro-3-sulfamoylphenyl)-3-methyl-2-methylimino-1,3-thiazolidine-4-ol 0.7 g of lactic acid were added in 10 ml of ethanol, the mixture was stirred for 3 hours at room temperature and precipitated with diisopropyl ether. After decanting of the solvent the oil was dissolved in water and lyophilized. The result was a colorless, amorphous solid substance that was decomposed from 120° C onwards, $\bar{\gamma}C=N$ 1630 cm$^{-1}$.

EXAMPLE 9

4-(4-Chloro-3-sulfamoylphenyl)-3-methyl-2-methylimino-1,3-thiazolidine-4-ol-maleinate 1.5 g of 4-(4-chloro-3-sulfamoylphenyl)-3-methyl-2-methylimino-1,3-thiazolidine-4-ol were stirred in 10 ml of ethanol with 0.7 of maleic acid for 1 hour at room temperature, the salt desired was precipitated with 50 ml of diisopropyl ether and crystallized under fresh diisopropyl ether/ethyl acetate to yield colorless crystals which melted at 167° C. (decomposition).

EXAMPLE 10

4-(4-Chloro-3-sulfamoylphenyl)-3-methyl-2-methylimino-1,3-thiazolidine-4-ol-citrate 1.5 g of 4-(4-chloro-3-sulfamoylphenyl)-3-methyl-2-methylimino-1,3-thiazolidine-4-ol were reacted in the manner described in example 8 with 1 g of ground citric acid and worked up. Colorless amorphous solid substance, decomposition from 130° C. on, $\bar{\gamma}C=N$ 1620 cm$^{-1}$.

EXAMPLE 11

4-(4-Chloro-3-sulfamoylphenyl)-3-methyl-2-methylimino-1,3-thiazolidine-4-ol-salizylate 1.5 g of 4-(4-chloro-3-sulfamoylphenyl)-3-methyl-2-methylimino-1,3-thiazolidine-4-ol were reacted with 0.7 g of salizylic acid in the manner described in Example 8 and worked up. Colorless, amorphous solid substance: decomposition from 131° C., $\bar{\gamma}C=N$ 1630 cm$^{-1}$.

EXAMPLE 12

3-Ethyl-2-ethylimino-4-(4-chloro-3-sulfamoylphenyl)-1,3-thiazolidine-4-ol-hydrobromide To 6.2 g of 2-bromo-4'-chloro-3'-sulfamoylacetophenone 2.2 g of ground 1,3-diethyl-thiourea were added in 40 ml of methanol, the mixture was stirred for 10 minutes at 40° C. and for 3 hours at room temperature and the salt was precipitated by adding diethyl ether. After decanting the solvent, the oily product was crystallized with diisopropyl ether heated to 30°-40° C. Colorless crystals melting at 203° C. (decomposition).

EXAMPLE 13

3-Ethyl-2-ethylimino-4-(4-chloro-3-sulfamoylphenyl)-1,3-thiazolidine-4-ol-hydrochloride (a) 5.2 g of 2,4'-dichloro-3'-sulfamoylacetophenone were reacted in the manner described in Example 12, the end product was precipitated with diethyl ether and crystallized with ethyl acetate. Reprecipitation from 1 part of methanol (active charcoal) and 3 parts of ethyl acetate led to colorless crystals which melted at 177° C. (decomposition).

(b) 17 g of 3-ethyl-2-ethylimino-4-(4-chloro-3-sulfamoylphenyl)-1,3-thiazolidine-4-ol-hydrobromide were suspended in 100 ml of methanol and shortly heated to boiling after the addition of 10 ml of triethyl amine. The solvent was distilled off under reduced pressure, 150 ml of water were added to the residue and the mixture was extracted with 200 ml of ethyl acetate. After drying the organic phase over sodium sulfate the solvent was distilled off under reduced pressure. The residue was dissolved in 100 ml of acetone, the solution was acidified with 15% ethanolic HCl and the oily precipitate of the end product was crystallized with acetone heated to 40° C. Melting point: 177° C. (decomposition).

EXAMPLE 14

3-Ethyl-2-ethylimino-4-(4-chloro-3-sulfamoylphenyl)-5-methyl-1,3-thiazolidine-4-ol-hydrobromide 4.6 g of 4'-chloro-3'-sulfamoyl-propiophenone were reacted according to the prescription given in Example 1(a) with 1 ml of bromine and the solvent was distilled off under reduced pressure. The oily residue of the 2-bromo-4'-chloro-3'-sulfamoyl-propiophenone was dissolved without further purification in 50 ml of ethanol, stirred for 2 hours at room temperature after adding 2.6 g of 1,3-diethylthio urea and allowed to dwell over night. The end product was precipitated with ether, the solvent was decanted, the oily residue was dissolved in water and lyophilized. Colorless, amorphous solid body: decomposition from 140° C. on, $\bar{\gamma}C=N$ 1610 cm$^{-1}$.

EXAMPLE 15

5-Ethyl-4-(4-chloro-3-sulfamoylphenyl)-3-methyl-2-methylimino-1,3-thiazolidine-4-ol-hydrobromide (a) 6.1 g of 4'-chloro-3'-sulfamoyl-butyrophenone were reacted according to the prescription given in Example 1(a) with 3.85 g of bromine in 100 ml of ethyl acetate, the solvent was decanted under reduced pressure and the oily residue of the 2-bromo-4'-chloro-3'-sulfamoyl-butyrophenone was crystallized with a small amount of diisopropyl ether. Melting point: 59° C.

(b) 5.6 g of 2-bromo-4'-chloro-3'-sulfamoyl-butyrophenone and 1.7 g of 1,3-dimethylthio urea were heated in 50 ml of methanol for 10 minutes to 40° C. and stirred for another 2 hours at room temperature. Precipitation followed by adding diisopropyl ether and the oily end product was crystallized with diethyl ether. Colorless solid body: decomposition from 98° C. on, $\bar{\gamma}C=N$ 1620 cm$^{-1}$.

EXAMPLE 16

4-(4-Chloro-3-sulfamoylphenyl)-3-propyl-2-propylimino-1,3-thiazolidine-4-ol-hydrochloride 5.3 g of 2,4'-dichloro-3'-sulfamoylacetophenone and 3.2 g of ground 1,3-dipropylthio urea were heated in 45 ml of methanol for 5 minutes to 50° C. and stirred for another 30 minutes at room temperature. After pouring the reaction mixture into 120 ml of diethyl ether the end product was obtained as a visquous mass which crystallized under mild heating rapidly with ether. Colorless solid body: melting point: 175° C. (decomposition).

EXAMPLE 17

4-(4-Chloro-3-sulfamoylphenyl)-2-isopropylimino-3-methyl-1,3-thiazolidine-4-ol-hydrobromide 6.1 g of 2-bromo-4'-chloro-3'-sulfamoylacetophenone were heated with 2.4 g of 1-methyl-3-isopropylthiourea in 50 ml of acetone for 10 minutes to 40° C., the separating oil was triturated to form crystals and the crystalline suspension was stirred for 1 hour at room temperature. Colorless solid body: melting point: 195° C. (decomposition).

EXAMPLE 18

4-(4-Chloro-3-sulfamoylphenyl)-2-isopropylimino-3-methyl-1,3-thiazolidine-4-ol 7 g of ground 4-(4-chloro-3-sulfamoylphenyl)-2-isopropylimino-3-methyl-1,3-thiazolidine-4-ol-hydrobromide were dissolved in 80 ml of 40° C. hot water and stirred for 30 minutes at 40° C. after adding it to a mixture of 60 ml of saturated sodium bicarbonate solution and 100 ml of water. After cooling to room temperature, the mixture was extracted with 200 ml of diethyl ether, the organic phase was dried over sodium sulfate and the solvent was distilled off under reduced pressure. The residue was dissolved in 40 ml of diisopropyl ether and the end product was precipitated by pouring it into 200 ml of stirred petroleum ether. Colorless solid body: decomposition beginning at 100° C., $\bar{\gamma}C=N$ 1610 cm$^{-1}$.

EXAMPLE 19

4-(4-Chloro-3-sulfamoylphenyl)-2-isopropylimino-3-methyl-1,3-thiazolidine-4-ol-hydrochloride A solution of 6 g of 4-(4-chloro-3-sulfamoylphenyl)-2-isopropylimino-3-methyl-1,3-thiazolidine-4-ol in 30 ml of ethyl acetate was made acid by adding, dropwise, 15% ethanolic hydrochloric acid. The solution was triturated to crystallize, allowed to stand over night at 0° C. and the crystals were filtered off. Colorless solid body: melting point: 186° C. (decomposition).

EXAMPLE 20

4-(4-Chloro-3-sulfamoylphenyl)-3-isopropyl-2-isopropylimino-1,3-thiazolidine-4-ol-hydrochloride 5.2 g of 2,4'-dichloro-3'-sulfamoylacetophenone were reacted with 3.2 g of 1,3-diisopropylthio urea and worked up in the manner prescribed in Example 12. Colorless solid body: melting point: 191° C. (decomposition).

EXAMPLE 21

3-n-Butyl-2-n-butylimino-4-(4-chloro-3-sulfamoylphenyl)-1,3-thiazolidine-4-ol-hydrobromide 6.2 g of 2-bromo-4'-chloro-3'-sulfamoylacetophenone were reacted with 3.8 g of 1,3-di-n-butylthiourea according to the prescription given in Example 12 and the end product was precipitated with diisopropyl ether. Colorless amorphous solid body: decomposition beginning at 100° C., $\bar{\gamma}C=N$ 1615 cm$^{-1}$.

EXAMPLE 22

3-n-Butyl-2-n-butylimino-4-(4-chloro-3-sulfamoylphenyl)-1,3-thiazolidine-4-ol-hydrochloride 5.2 g of 2,4'-dichloro-3'-sulfamoylacetophenone were reacted with 3.8 g of 1,3-di-n-butylthiourea according to the prescription given in Example 12 and the end product was precipitated with diisopropyl ether. Colorless crystalline solid body: melting point: 164° C. (decomposition).

EXAMPLE 23

3-Ethyl-4-(4-chloro-3-sulfamoylphenyl)-2-isopropylimino-1,3-thiazolidine-4-ol-hydrochloride 6.2 g of 2-bromo-4'-chloro-3'-sulfamoylacetophenone and 2.92 g of 1-ethyl-3-isopropylthiourea were heated in 40 ml of acetone for 15 minutes to 40° C., the mixture was stirred for another 30 minutes at room temperature and the crystals were filtered. Colorless crystalline solid body: melting point: 188° C. (decomposition).

EXAMPLE 24

3-Ethyl-4-(4-chloro-3-sulfamoylphenyl)-2-isopropylimino-1,3-thiazolidine-4-ol-hydrochloride 5.5 g of 3-ethyl-4-(4-chloro-3-sulfamoylphenyl)-2-isopropylimino-1,3-thiazolidine-4-ol-hydrochloride were dissolved in 30 ml of hot water and added to a stirred mixture of 50 ml of ethyl acetate and 20 ml of saturated aqueous sodium bicarbonate solution. The organic phase was separated, dried over sodium sulfate and the solvent was distilled off under reduced pressure. The oily 3-ethyl-4-(4-chloro-3-sulfamoylphenyl)-2-isopropylimino-1,3-thiazolidine-4-ol was dissolved in 15 ml of ethanol, 15% ethanolic hydrochloric acid was added dropwise while cooling and the end product was precipitated by adding diisopropyl ether. Colorless crystalline solid body: melting point: 175° C. (decomposition).

EXAMPLE 25

3-sec.-Butyl-2-sec.-butylimino-4-(4-chloro-3-sulfamoylphenyl)-1,3-thiazolidine-4-ol-hydrochloride 5.3 g of 2,4'-dichloro-3'-sulfamoylacetophenone and 3.8 g of 1,3-di-sec.-butylthiourea was reacted in the manner described in Example 16, the reaction mixture was introduced into a solution of 40 ml of diethyl ether and 120 ml of ethyl acetate and the colorless, crystalline end product was filtered off after stirring for 4 hours at room temperature. Melting point: 186° C. (decomposition).

EXAMPLE 26

4-(4-Chloro-3-sulfamoylphenyl)-3-isobutyl-2-isobutylimino-1,3-thiazolidine-4-ol-hydrochloride 5.3 g of 2,4'-dichloro-3'-sulfamoylacetophenone and 3.8 g of 1,3-diisobutylthiourea were reacted according to the prescription made in Example 16 and worked up as described in Example 25. Colorless, crystalline end product: melting point: 176° C. (decomposition).

EXAMPLE 27

4-(4-Chloro-3-sulfamoylphenyl)-2-isobutylimino-3-methyl-1,3-thiazolidine-4-ol-hydrobromide 6.2 g of 4'-chloro-3'-sulfamoyl-2-bromoacetophenone and 3.0 g of 1-isobutyl-3-methylthiourea were reacted according to the prescription made in Example 23 and the colorless end product was precipitated with 200 ml of diethyl ether. Decomposition beginning at 122° C., $\bar{\gamma}C\!=\!N$ 1620 cm$^{-1}$.

EXAMPLE 28

4-(4-Chloro-3-sulfamoylphenyl)-2-isobutylimino-3-methyl-1,3-thiazolidine-4-ol 8 g of 4-(4-chloro-3-sulfamoylphenyl)-2-isobutylimino-3-methyl-1,3-thiazolidine-4-ol-hydrobromide were dissolved in 30 ml of water and the end product was precipitated by pouring it into 20 ml of a saturated and stirred sodium carbonate solution. Colorless, amorphous solid body, $\bar{\gamma}C\!=\!N$ 1615 cm$^{-1}$.

EXAMPLE 29

2-sec.-Butylimino-4-(4-chloro-3-sulfamoylphenyl)-3-methyl-1,3-thiazolidine-4-ol-hydrobromide 4.7 g of 2-bromo-4'-chloro-3'-sulfamoylacetophenone and 2.19 g of 1-sec.-butyl-3-methylthiourea were reacted according to the prescription given in Example 23 and the crystals were filtered off. Melting point: 163° C. (decomposition).

EXAMPLE 30

2-sec.-Butylimino-4-(4-chloro-3-sulfamoylphenyl)-3-methyl-1,3-thiazolidine-4-ol 6 g of 4-(4-chloro-3-sulfamoylphenyl)-2-sec.-butylimino-3-methyl-1,3-thiazolidine-4-ol-hydrobromide were reacted according to the prescription given in Example 28. Colorless solid body: decomposition beginning at 99° C., $\bar{\gamma}C\!=\!N$ cm$^{-1}$.

EXAMPLE 31

4-(4-Chloro-3-sulfamoylphenyl)-3-n-hexyl-2-n-hexylimino-1,3-thiazolidine-4-ol-hydrochloride 5.2 g of 2,4'-dichloro-3'-sulfamoylacetophenone and 4.8 g of 1,3-di-n-hexyl-thiourea were reacted according to the prescription given in Example 12, the end product was precipitated with diethyl ether and the remaining oil was treated with cyclohexane. Colorless, amorphous solid body: decomposition beginning at 75° C., $\bar{\gamma}C\!=\!N$ 1615 cm$^{-1}$.

EXAMPLE 32

3-Allyl-2-allylimino-4-(4-chloro-3-sulfamoylphenyl)-1,3-thiazolidine-4-ol-hydrochloride 5.2 g of 2,4'-dichloro-3'-sulfamoylacetophenone and 2.5 g of 1,3-diallyl-thiourea were reacted according to the prescription given in Example 12, the end product was precipitated with diisopropyl ether and the oil obtained was crystallized with diethyl ether/ethyl acetate (1:1). Colorless solid body: melting point: 158° C. (decomposition).

EXAMPLE 33

3-Allyl-4-(4-chloro-3-sulfamoylphenyl)-2-isopropylimino-1,3-thiazolidine-4-hydrobromide 6.2 g of 2-bromo-4'-chloro-3'-sulfamoylacetophenone and 3.16 g of 1-allyl-3-isopropylthiourea were reacted according to the prescription given in Example 23 and the colorless crystalline end product was filtered off. Melting point: 180° C. (decomposition).

EXAMPLE 34

3-Allyl-4-(4-chloro-3-sulfamoylphenyl)-2-cyclopropylimino-1,3-thiazolidine-4-ol-hydrobromide 6.2 g of 2-bromo-4'-chloro-3'-sulfamoylacetophenone and 3.1 g of 1-allyl-3-cyclopropylthiourea were reacted and worked up according to the prescription given in Example 12. Colorless, amorphous solid body: decomposition beginning at 90° C., $\bar{\gamma}C\!=\!N$ 1600 cm$^{-1}$.

EXAMPLE 35

3-Allyl-4-(4-chloro-3-sulfamoylphenyl)-2-cyclopropylimino-1,3-thiazolidine-4-ol 6.2 g of 3-allyl-4-(4-chloro-3-sulfamoylphenyl)-2-cyclopropylimino-1,3-thiazolidine-4-ol-hydrobromide were reacted according to the prescription given in Example 28. Colorless, crystalline solid body: melting point: 140° C. (decomposition).

EXAMPLE 36

4-(4-Chloro-3-sulfamoyl-phenyl)-2-cyclopropylimino-3-methyl-1,3-thiazolidine-4-ol-hydrobromide 4.15 g of 2-bromo-4'-chloro-3'-sulfamoylacetophenone were reacted with 1.95 g of 1-cyclopropyl-3-methylthiourea according to the prescription given in Example 23 and the oily precipitate was crystallized with diisopropyl ether. Colorless, crystalline solid body: melting point: 204° C. (decomposition).

EXAMPLE 37

4-(4-Chloro-3-sulfamoylphenyl)-2-cyclopentylmethylimino-3-methyl-1,3-thiazolidine-4-ol-hydrobromide 4.7 g of 2-bromo-4'-chloro-3'-sulfamoylacetophenone were reacted with 2.6 g of 1-cyclopentylmethyl-3-methylthiourea according to the prescription given in Example 23 and the colorless crystalline final product was filtered off. Melting point: 189° C. (decomposition).

EXAMPLE 38

4-(4-Chloro-3-sulfamoylphenyl)-2-cyclopentylmethylimino-3-methyl-1,3-thiazolidine-4-ol 6 g of 4-(4-chloro-3-sulfamoylphenyl)-2-cyclopentylmethylimino-3-methyl-1,3-thiazolidine-4-ol-hydrobromide were reacted according to the prescription given in Example 2(c) with sodium bicarbonate. Colorless solid body: decomposition beginning at 115° C. $\bar{\gamma}C\!=\!N$ 1615 cm$^{-1}$.

EXAMPLE 39

4-(4-Chloro-3-sulfamoylphenyl)-2-cyclohexylimino-3-methyl-1,3-thiazolidine-4-ol-hydrobromide 4.7 g of 2-bromo-4'-chloro-3'-sulfamoylacetophenone were reacted with 2.6 g of 1-cyclohexyl-3-methylthiourea in the manner described in Example 23 and the colorless crystalline end product was filtered off. Melting point: 178° C. (decomposition).

EXAMPLE 40

4-(4-Chloro-3-sulfamoylphenyl)-2-cyclohexylimino-3-methyl-1,3-thiazolidine-4-ol 6 g of 4-(4-chloro-3-sulfamoylphenyl)-2-cyclohexylimino-3-methyl-1,3-thiazolidine-4-ol-hydrobromide were reacted according to the prescription made in Example 28. Colorless solid body: decomposition beginning at 106° C., $\bar{\gamma}$ C=N 1610 cm$^{-1}$.

EXAMPLE 41

4-(4-Chloro-3-sulfamoylphenyl)-3-cyclopropyl-2-cyclopropylimino-1,3-thiazolidine-4-ol-hydrochloride 5.2 g of 2,4'-dichloro-3'-sulfamoylacetophenone and 3.1 g of 1,3-dicyclopropylthiourea were reacted according to the prescription given in Example 12 and the colorless crystalline precipitate of the end product was filtered off.

EXAMPLE 42

4-(4-Chloro-3-sulfamoylphenyl)-3-cyclohexyl-2-cyclohexylimino-1,3-thiazolidine-4-ol-hydrochloride 5.2 g of 2,4'-dichloro-3'-sulfamoylacetophenone and 4.8 g of 1,3-dicyclohexylthiourea were reacted according to the prescription made in Example 12, the end product was precipitated with 200 ml of diethyl ether and the oil was crystallized after decanting the solvent with diethyl ether. Colorless, crystalline solid body: melting point: 177° C. (from acrylonitrile).

EXAMPLE 43

4-(4-Chloro-3-sulfamoylphenyl)-3-cyclooctyl-2-cyclooctylimino-1,3-thiazolidine-4-ol-hydrochloride 5.2 g of 2,4'-dichloro-3'-sulfamoylacetophenone and 5.8 g of 1,3-dicyclooctylthiourea were reacted according to the prescription made in Example 12 and worked up according to the prescription of Example 42. Colorless solid body: decomposition beginning at 118° C., $\bar{\gamma}$C=N 1600 cm$^{-1}$.

EXAMPLE 44

3-(4-Chloro-3-sulfamoylphenyl)-3-hydroxy-2,3,5,6-tetrahydroimidazo-[2,1-b]-thiazole-hydrobromide 6.2 g of 2-bromo-4'-chloro-3'-sulfamoylacetophenone and 2 g of ground 2-imidazolidine-thione were reacted according to the prescription given in Example 12 and the crystalline precipitate was filtered off. Colorless solid body: decomposition beginning at 100° C., $\bar{\gamma}$C=N 1590 cm$^{-1}$.

EXAMPLE 45

3-(4-Chloro-3-sulfamoylphenyl)-3-hydroxy-2,3,6,7-tetrahydro-5H-thiazole[3,2-a]pyrimidine-hydrobromide 6.2 g of 2-bromo-4'-chloro-3'-sulfamoylacetophenone and 2.4 g of ground 3,4,5,6-tetrahydro-2-pyrimidine-thiol were reacted according to the prescription given in Example 12, the reaction mixture was poured into 400 ml of ethyl acetate and the oily precipitate of the end product was crystallized by heating to 50°-60° C. Colorless, crystalline solid body: melting point: 330°-333° C. (water separation at 210°-220° C.).

EXAMPLE 46

3-(4-chloro-3-sulfamoylphenyl)-3-hydroxy-2,3,6,7-tetrahydro-5H-thiazolo[3,2-a]pyrimidine-hydrochloride 5.2 g of 2,4'-dichloro-3'-sulfamoylacetophenone and 2.4 g of ground 3,4,5,6-tetrahydro-2-pyrimidine-thiol were reacted in the manner described in Example 12, the reaction mixture was precipitated with 200 ml of diethyl ether, the solvent was decanted and the oily end product was crystallized under warm ethyl acetate. Colorless crystalline solid body, melting point: 180° C. (decomposition).

EXAMPLE 47

3-(4-Chloro-3-sulfamoylphenyl)-6,6-dimethyl-3-hydroxy-2,3,5,6-tetrahydro-imidazo[2,1-b]thiazole-hydrobromide 3.1 g of 2-bromo-4'-chloro-3'-sulfamoylacetophenone and 1.3 g of 4,4-dimethyl-2-imidazolidine-thione were reacted as described in Example 12 in 15 ml of methanol, the reaction mixture was precipitated with 70 ml of diethyl ether and the oily precipitate was crystallized with ethyl acetate at 40° to 50° C. Colorless, crystalline solid body: melting point: 164° C. (decomposition).

EXAMPLE 48

3-(4-Chloro-3-sulfamoylphenyl)-3-hydroxy-2,3-dihydro-5H-thiazolo[3,2-b]quinazoline 3 g of 3-(4-chloro-3-sulfamoylphenyl-3-hydroxy-2,3-dihydro-5H-thiazolo[3,2-b]quinazoline-hydrobromide were reacted according to the prescription of Example 2(c) with aqueous sodium bicarbonate solution and the colorless crystals were filtered off. Melting point: 181° C. (decomposition) (from water/methanol).

EXAMPLE 49

4-(4-Chloro-3-sulfamoylphenyl)-2-(2-chlorobenzylimino)-3-methyl-1,3-thiazolidine-4-ol-hydrobromide 4.7 g of 2-bromo-4'-chloro-3'-sulfamoylacetophenone and 3.1 g of 1-(2-chlorobenzyl)-3-methylthiourea were reacted according to Example 23 and the crystalline end product was filtered off. Colorless crystalline solid body: melting point: 182° C. (decomposition).

EXAMPLE 50

4-(4-Chloro-3-sulfamoylphenyl)-2-(2-chlorobenzylimino)-3-methyl-1,3-thiazolidine-4-ol 6 g of 4-(4-chloro-3-sulfamoylphenyl)-2-(2-chlorobenzylimino)-3-methyl-1,3-thiazolidine-4-ol-hydrobromide were reacted according to the prescription given in Example 2(c). Colorless solid body: decomposition beginning at 114° C., $\bar{\gamma}$C=N 1615 cm$^{-1}$.

EXAMPLE 51

2-Benzylimino-4-(4-chloro-3-sulfamoylphenyl)-3-methyl-1,3-thiazolidine-4-ol 4.7 g of 2-bromo-4'-chloro-3'-sulfamoylacetophenone and 2.7 g of 1-benzyl-3-methylthiourea were reacted as prescribed in Example 23 and the reaction mixture was introduced into 200 ml of diethyl ether while stirring.

The hygroscopic crystals of the 2-benzylimino-4-(4-chloro-3-sulfamoylphenyl)-3-methyl-1,3-thiazolidine-4-ol-hydrobromide were rapidly filtered off, dissolved in 70 ml of water and converted into the end product according to the prescription of Example 28. Colorless solid body: decomposition beginning at 110° C., $\bar{\nu}$C=N 1610 cm$^{-1}$.

EXAMPLE 52

4-(4-Chloro-3-sulfamoylphenyl)-3-methyl-2-(3,4-methylenedioxybenzyl)-1,3-thiazolidine-4-ol-hydrobromide 4.7 g of 2-bromo-4'-chloro-3'-sulfamoylacetophenone and 3.36 g of 1-methyl-3-(3,4-methylenedioxybenzyl)-thiourea were reacted according to the prescription of Example 23 and the crystalline end product was filtered off. Melting point: 145° C. (decomposition).

EXAMPLE 53

4-(4-Chloro-3-sulfamoylphenyl)-3-dimethylamino-4-hydroxy-1,3-thiazolidine-2-N,N-dimethylhydrazone-hydrochloride 5.2 g of 2,4'-dichloro-3'-sulfamoylacetophenone and 3.2 g of 1,1,5,5-tetramethylthiocarbohydrazide were reacted as prescribed in Example 12 and the reaction mixture was poured into diethyl ether. After decanting the solvent, the oily end product was crystallized under diisopropyl ether. Colorless crystals: melting point 117° C. (decomposition).

EXAMPLE 54

4-(4-Chloro-3-sulfamoylphenyl)-3-cyclohexyl-4-hydroxy-1,3-thiazolidine-2-N,N-dimethylhydrazone 4.7 g of 2-bromo-4'-chloro-3'-sulfamoylacetophenone and 3 g of 4-cyclohexyl-1,1-dimethylthiosemicarbazide were reacted according to the prescription of Example 23, the 4-(4-chloro-3-sulfamoylphenyl)-3-cyclohexyl-4-hydroxy-1,3-thiazolidine-2-N,N-dimethylhydrazone-hydrobromide was precipitated with 200 ml of diethyl ether, the hygroscopic crystals were rapidly filtered off and dissolved in 30 ml of warm water. The end product was obtained according to the prescription of Example 2(c) by treating with saturated sodium carbonate solution. Colorless crystalline solid body: melting point 119° C. (decomposition).

EXAMPLE 55

4-(4-Chloro-3-sulfamoylphenyl)-3-dimethylamino-2-isopropylimino-1,3-thiazolidine-4-ol-hydrobromide 4.7 g of 2-bromo-4'-chloro-3'-sulfamoylacetophenone and 2.4 g of 1,1-dimethyl-4-isopropylthiosemicarbazide were reacted according to the prescription of Example 23 and the crystalline end product was filtered off. Colorless crystals: melting point: 189° C. (decomposition).

EXAMPLE 56

4-(4-Chloro-3-sulfamoylphenyl)-4-hydroxy-3-methyl-1,3-thiazolidine-2-N,N-dimethylhydrazone-hydrobromide 4.7 g of 2-bromo-4'-chloro-3'-sulfamoylacetophenone and 2 g of 1,1,4-trimethylthiosemicarbazide were reacted according to the prescription of Example 23 and the crystalline end product was filtered off. Colorless crystals: melting point: 145° C. (decomposition).

EXAMPLE 57

4-(4-Chloro-3-sulfamoylphenyl)-2-(2-furylmethylimino)-3-methyl-1,3-thiazolidine-4-ol-hydrobromide 4.7 g of 2-bromo-4'-chloro-3'-sulfamoylacetophenone and 2.55 g of 1-(2-furylmethyl)-3-methylthiourea were reacted according to the prescription of Example 23 and the end product was precipitated by adding 100 ml of diethyl ether. Colorless crystalline solid body: melting point: 168° C. (decomposition).

EXAMPLE 58

4-(4-Chloro-3-sulfamoylphenyl)-3-methyl-2-(2-methoxypropylimino)-1,3-thiazolidine-4-ol-hydrobromide 4.7 g of 2-bromo-4'-chloro-3'-sulfamoylacetophenone and 2.19 g of 1-methyl-3-(2-methoxypropyl)-thiourea were reacted as prescribed in Example 23 and the crystalline end product was filtered off. Colorless solid crystals: melting point: 167° C. (decomposition).

EXAMPLE 59

4-(4-Chloro-3-sulfamoylphenyl)-3-methyl-2-(2-methoxypropylimino)-1,3-thiazolidine-4-ol 5 g of 4-(4-chloro-3-sulfamoylphenyl)-3-methyl-2-(2-methoxypropylimino)-1,3-thiazolidine-4-ol-hydrobromide were reacted as prescribed in Example 18 and the end product was extracted with 150 ml of ethyl acetate. After drying the organic phase over sodium sulfate, the solvent was distilled off under reduced pressure, the solid residue was additioned with 40 ml of diisopropyl ether and the colorless crystals were filtered off. Melting point: 149° C. (decomposition).

EXAMPLE 60

4-(4-Chloro-3-sulfamoylphenyl)-3-methyl-2-(2-pyridylmethylimino)-1,3-thiazolidine-4-ol-hydrochloride 5.2 g of 2,4'-dichloro-3'-sulfamoylacetophenone and 3.5 g of 1-methyl-3-(2-pyridylmethyl)-thiourea were reacted as prescribed in Example 12 and the end product was precipitated with 400 ml of ethyl acetate while stirring. Colorless crystals, melting point 152° C. (decomposition) $\bar{\nu}$C=N 1620 cm$^{-1}$.

EXAMPLE 61

4-(4-Chloro-3-sulfamoylphenyl)-3-methyl-2-(3-pyridylmethylimino)-1,3-thiazolidine-4-ol 4.7 g of 2-bromo-4'-chloro-3'-sulfamoylacetophenone and 2.7 g of 1-methyl-3-(3-pyridylmethyl)-thiourea were reacted as prescribed in Example 23, whereupon the 4-(4-chloro-3-sulfamoylphenyl)-3-methyl-2-(3-pyridylmethylimino)-1,3-thiazolidine-4-ol-hydrobromide precipitated in the form of colorless hygroscopic crystals. The substance was rapidly filtered off, introduced into 30 ml of saturated sodium bicarbonate solution while stirring and the end product was crystallized by trituration. Fair yellow crystals melting at 184° C. (decomposition).

EXAMPLE 62

3-Allyl-4-(4-chloro-3-sulfamoylphenyl)-2-(3-pyridylmethylimino)-1,3-thiazolidine-4-ol-hydrobromide 4.7 g of 2-bromo-4'-chloro-3'-sulfamoylacetophenone and 3 g of 1-allyl-3-(3-pyridylmethyl)-thiourea were reacted as prescribed in Example 23 and the end product was filtered off. Colorless solid body, decomposition beginning at 82° C. $\bar{\gamma}$C=N 1605 cm$^{-1}$.

EXAMPLE 63

4(4-Chloro-3-sulfamoylphenyl)-3-cyclohexyl-2-(3-pyridylmethylimino)-1,3-thiazolidine-4-ol-hydrobromide 4.7 g of 2-bromo-4'-chloro-3'-sulfamoylacetophenone and 3.7 g of 1-cyclohexyl-3-(3-pyridylmethyl)-thiourea were reacted as prescribed in Example 23. The end product precipitated first as oil and crystallized after stirring for several hours at room temperature. Colorless crystals, melting point 140° C., decomposition beginning at 165° C., $\bar{\gamma}$C=N 1600 cm$^{-1}$.

EXAMPLE 64

4-(4-Chloro-3-sulfamoylphenyl)-3-cyclohexyl-2-(2-pyridylmethylimino)-1,3-thiazolidine-4-ol-hydrobromide 4.7 g of 2-bromo-4'-chloro-3'-sulfamoylacetophenone and 3.75 g of 1-cyclohexyl-3-(2-pyridylmethyl)-thiourea were reacted according to the prescription given in Example 23 and the crystals were filtered off. Colorless solid body, melting point: 249° C. (decomposition).

EXAMPLE 65

3-Ethyl-4-(4-chloro-3-sulfamoylphenyl)-2-(2-pyridylmethylimino)-1,3-thiazolidine-4-ol 4.7 g of 2-bromo-4'-chloro-3'-sulfamoylacetophenone and 3 g of 1-ethyl-3-(2-pyridylmethyl)-thiourea were reacted according to the prescription given in Example 23 and 150 ml of diethyl ether were added to the reaction mixture. The hygroscopic 3-ethyl-4-(4-chloro-3-sulfamoylphenyl)-2-(2-pyridylmethylimino)-1,3-thiazolidine-4-ol-hydrobromide which had separated as crystals was rapidly filtered off, dissolved in 50 ml of water and converted into the end product as described in Example 28. Colorless solid body, decomposition beginning at 135° C., $\bar{\gamma}$C=N 1615 cm$^{-1}$.

EXAMPLE 66

3-Ethyl-2-ethylimino-4-(4-bromo-3-sulfamoylphenyl)-1,3-thiazolidine-4-ol-hydrochloride (a) 4-Bromo-3-sulfamoylbenzoyl chloride 10 g of 4-bromo-3-sulfamoylbenzoic acid were heated under reflux in a mixture of 80 ml of thionyl chloride and 50 ml of dioxane until HCl had completely developped. Then, the reaction mixture was concentrated under reduced pressure to 40 ml, 200 ml of petroleum ether were added and the crystals were filtered off. Melting point: 138° C. (decomposition).

(b) 4'-Bromo-3'-sulfamoyl-2-chloroacetophenone

The operational method described hereinafter has to be carried out under the precautions generally to be taken when working with N-nitroso-N-methyl urea and diazomethane.

26 g of freshly prepared N-nitroso-N-methyl urea were introduced portionwise at 0° to −5° C. into a stirred two-phase mixture of 200 ml of diethyl ether (or diisopropyl ether) and 80 ml of 40% aqueous potassium hydroxide solution, the ice-cold etheral diazomethane solution was separated in the separating funnel and dried over a small amount of solid potassium hydroxide at −10° C. during 3 hours. The dry solution of the diazomethane in diethyl ether (or diisopropyl ether) was cooled to −5° C. to −10° C. in a 500 ml three-neck flask provided with stirrer, inner thermometer and KOH drying tube. A suspension of 16.8 g of 4-bromo-3-sulfamoylbenzoyl chloride was added in small portions into 40 ml of anhydrous ethyl acetate, the temperature of the reaction mixture not being allowed to exceed +5° C. After the addition of 4-bromo-3-sulfamoylbenzoyl chloride stirring was continued for another 10 minutes at +5° C. and the fair yellow crystalline precipitate of 4'-bromo-3'-sulfamoyl-diazoacetophenone was filtered off. The 4'-bromo-3'-sulfamoyl-diazoacetophenone so obtained was introduced without further purification in small portions into a stirred mixture cooled to 0° C. of 30 ml of diethylene glycol dimethyl ether and 20 ml of concentrated HCl (37%). After nitrogen development had finished, stirring was continued for another 10 minutes at 0° C., 150 ml of water were added and after dwelling for 1 hour at 0° C. the crystalline precipitate of 4'-bromo-3'-sulfamoyl-2-chloroacetophenone was filtered off. Colorless crystals, melting point: 152° C.

(c) 3-Ethyl-2-ethylimino-4-(4-bromo-3-sulfamoylphenyl)-1,3-thiazolidine-4-ol-hydrochloride 4.6 g of 4'-bromo-3'-sulfamoyl-2-chloroacetophenone and 1.8 g of ground 1,3-diethylthiourea were reacted and worked up according to the prescription given in Example 12. Colorless solid body, decomposition beginning at 103° C., C=N 1615 cm$^{-1}$.

EXAMPLE 67

3-Ethyl-2-ethylimino-4-(4-methyl-3-sulfamoylphenyl)-1,3-thiazolidine-4-ol-hydrochloride (a) 4-Methyl-3-sulfamoylbenzoyl chloride 10 g of 4-methyl-3-sulfamoylbenzoic acid were boiled under reflux for 8 hours in 50 ml of thionyl chloride and the reaction mixture was allowed to stand over night at 0° C. The crystals were collected on a sinter glass frit and washed with petroleum ether and diisopropyl ether. Melting point: 180° C. (decomposition).

(b) 4'-Methyl-3'-sulfamoyl-diazoacetophenone 12 g of 4-methyl-3-sulfamoylbenzoyl chloride were reacted as prescribed in Example 66(b) with diazomethane in diethyl ether and the substance precipitating as fair yellow precipitate was filtered off. Melting point: 176° C. (decomposition).

(c) 4'-Methyl-3'-sulfamoyl-2-chloroacetophenone 10 g of 4'-methyl-3'-sulfamoyl-diazoacetophenone were reacted as prescribed in Example 66(b) in diethylene glycol dimethyl ether with 37% HCl and worked up. Colorless crystals, melting point: 166° C. (from isopropanol).

(d) 3-Ethyl-2-ethylimino-4-(4-methyl-3-sulfamoylphenyl)-1,3-thiazolidine-4-ol-hydrochloride 5 g of 2-chloro-4'-methyl-3'-sulfamoylacetophenone and 2.7 g of 1,3-diethylthiourea were reacted as prescribed in Example 12. After addition of 200 ml of diisopropyl ether the solvent was decanted and the oily end product was crystallized under ethyl acetate heated to 40° to 50° C. Colorless solid body, melting point: 160° C. (decomposition).

EXAMPLE 68

3-Hydroxy-3-(4-methyl-3-sulfamoylphenyl)-2,3,6,7-tetrahydro-5H-thiazolo[3,2-a]pyrimidine-hydrochloride 5 g of 2-chloro-4'-methyl-3'-sulfamoylacetophenone and 2.35 g of ground 3,4,5,6-tetrahydro-2-pyrimidinethiol were reacted as prescribed in Example 12 and worked up as prescribed in Example 67(d). Colorless crystals, melting point: 190° C. (decomposition).

EXAMPLE 69

3-Isopropyl-2-isopropylimino-4-(4-methyl-3-sulfamoylphenyl)-1,3-thiazolidine-4-ol-hydrochloride 5 g of 2-chloro-4'-methyl-3'-sulfamoylacetophenone and 3.2 g of 1,3-diisopropyl thiourea were reacted as prescribed in Example 12 and worked up according to Example 67(d). Colorless crystals, melting point: 152° C. (decomposition).

EXAMPLE 70

3-Ethyl-2-ethylimino-4-(4-isopropyl-3-sulfamoylphenyl)-1,3-thiazolidine-4-ol-hydrochloride (a) 4-Isopropyl-3-sulfamoylbenzoic acid 10.3 g of 4-isopropyl benzoic acid were heated to 100° C. during 20 minutes in 30.5 ml of chlorosulfonic acid. The temperature was raised to 120° C. and maintained at that level until the HCl development had finished. Then, the reaction mixture was cooled to 10° C. and poured dropwise onto 200 g of ice while stirring. The crystalline precipitate of 3-chlorosulfonyl-4-isopropyl benzoic acid was filtered, washed with water several times and the still moist product was introduced in 80 ml of 25% aqueous ammonia solution, the temperature being maintained below 25° C. After dwelling over night, the reaction mixture was heated to 80° C. for 2 hours, the hot mixture was stirred for 15 minutes after the addition of a teaspoonfull of active charcoal and the charcoal was filtered off. The filtrate was adjusted to pH 1 with concentrated HCl, the crystalline 4-isopropyl-3-sulfamoylbenzoic acid was filtered off and washed with water several times. Colorless crystals, melting point: 245° C. (from water/ethanol).

(b) 4-Isopropyl-3-sulfamoylbenzoylchloride 5 g of 4-isopropyl-3-sulfamoylbenzoic acid were boiled under reflux in 50 ml of thionylchloride until completely dissolved and the reaction mixture was then concentrated to 25 ml under reduced pressure. After allowing to dwell over night at 0° C., the crystals were filtered off over a sinter glass frit and washed with petroleum ether. Colorless body, melting point: 177° C.

(c) 2-Chloro-4'-isopropyl-3'-sulfamoylacetophenone 13.5 g of 4-isopropyl-3-sulfamoylbenzoyl chloride were reacted as prescribed in Example 66(b) with diazomethane in ether, the 4'-isopropyl-3'-sulfamoyl-diazoacetophenone remaining in solution without precipitating as crystals. The solution so obtained was allowed to flow into a mixture of 200 ml of diethylene glycol-dimethyl ether and 100 ml of concentrated hydrochloric acid while stirring and cooling with ice, whereafter the solvent was largely distilled off under reduced pressure. To the oily residue, 500 ml of water were added and the solution was extracted with 200 ml of ethyl acetate. Drying followed over sodium sulfate and the solvent was distilled off under reduced pressure. The oily residue crystallized in the course of 1 to 3 days and was then triturated under a small amount of xylene and filtered off. Melting point: 141° C.

(d) 3-Ethyl-2-ethylimino-4-(4-isopropyl-3-sulfamoylphenyl)-1,3-thiazolidine-4-ol-hydrochloride 5.5 g of 2-chloro-4'-isopropyl-3'-sulfamoylacetophenone and 2.2 g of 1,3-diethylthio urea were reacted and worked up as prescribed in Example 12. Colorless solid body, decomposition beginning at 96° C., $\bar{\gamma}$ C=N 1610 cm$^{-1}$.

EXAMPLE 71

3-Methyl-2-methylimino-4-(3-sulfamoylphenyl)-1,3-thiazolidine-4-ol-hydrochloride (a) 3-Sulfamoylbenzoyl chloride 10 g of ground 3-sulfamoylbenzoic acid were reacted as prescribed in Example 70(b), the thionyl chloride was distilled off and the residue was crystallized under a mixture of petroleum ether and diethyl ether (1:1). Melting point: 123° C.

(b) 3'-Sulfamoyl-diazoacetophenone 11 g of 3-sulfamoylbenzoyl chloride were reacted as prescribed in Example 66(b) with diazomethane in diethyl ether and the crystals were filtered off. Melting point: 142° C.

(c) 2-Chloro-3'-sulfamoylacetophenone 9.5 g of 3'-sulfamoyl-diazoacetophenone were reacted as prescribed in Example 66(b) with 37% HCl in diethylene glycol dimethyl ether and worked up. Colorless crystals, melting point: 118° C. (from a small amount of ethanol).

(d) 3-Methyl-2-methylimino-4-(3-sulfamoylphenyl)-1,3-thiazolidine-4-ol-hydrochloride 3.5 g of 2-chloro-3'-sulfamoylacetophenone and 1.56 g of ground 1,3-dimethylthiourea were reacted as prescribed in Example 12 and the end product was precipitated with a mixture of 1 part of diethyl ether and 2 parts of ethyl acetate. Colorless crystals, melting point: 184° C.

EXAMPLE 72

3-Ethyl-2-ethylimino-4-(3-sulfamoylphenyl)-1,3-thiazolidine-4-ol-hydrochloride 3.5 g of 2-chloro-3'-sulfamoylacetophenone and 2.1 g of ground 1,3-diethylthiourea were reacted as prescribed in Example 12. 150 ml of diisopropyl ether were added, the solvent was decanted and the amorphous end product was crystallized under ethyl acetate. Colorless solid body, decomposition beginning at 80° C., $\bar{\gamma}$ C=N 1615 cm$^{-1}$.

EXAMPLE 73

3-Ethyl-2-ethylimino-4-(4-chloro-3-methylsulfamoylphenyl)-1,3-thiazolidine-4-ol-hydrochloride (a) 4'-chloro-3'-methylsulfamoyl-diazoacetophenone 14 g of 4-chloro-3-sulfamoylbenzoylchloride were reacted as prescribed in Example 66(b) with diazomethane in diethyl ether and the crystallized precipitate was filtered. Fair yellow crystals, melting point: 174° C. (decomposition).

(b) 2,4'-Dichloro-3'-methylsulfamoylacetophenone 12 g of 4'-chloro-3'-methylsulfamoyl-diazoacetophenone were reacted as prescribed in Example 66(b) with concentrated HCl in diethyleneglycol dimethyl ether und worked up. Colorless crystals, melting point: 153° C.

(c) 3-Ethyl-2-ethylimino-4-(4-chloro-3-methylsulfamoylphenyl)-1,3-thiazolidine-4-ol-hydrochloride 5.6 g of 2,4'-dichloro-3'-methylsulfamoylacetophenone and 2.7 g of 1,3-diethylthiourea were reacted as prescribed in Example 12. After the addition of 100 ml of diisopropyl ether and a dwelling period of 1 hour at 0° C., the solvent was decanted and the oily end product was crystallized under boiling diethyl ether. Colorless solid body, melting point: 168° C. (decomposition).

EXAMPLE 74

3-Ethyl-2-ethylimino-4-(3-n-butylsulfamoyl-4-chlorophenyl)-1,3-thiazolidine-4-ol-hydrochloride (a) 3-n-Butylsulfamoyl-4-chlorobenzoylchloride 29.4 g of 3-n-butylsulfamoyl-4-chlorobenzoic acid were boiled under reflux in 140 ml of thionyl chloride until complete dissolution and until HCl had finished to develop (about 2 hours), the thionyl chloride was distilled off under reduced pressure and the residue was crystallized under diisopropyl ether. Colorless crystals, melting point: 110° C.

(b) 3'-n-Butylsulfamoyl-2,4'-dichloroacetophenone 17 g of 3-n-butylsulfamoyl-4-chlorobenzoyl chloride were reacted as prescribed in Example 66(b) with diazomethane in diethyl ether, the 3'-butylsulfamoyl-4'-chlorodiazoacetophenone remaining in solution without being separated. To the total of the reaction mixture, concentrated HCl in diethylene glycol dimethyl ether was added as prescribed in Example 70(c). The diethyl ether was distilled off under reduced pressure, the remaining solution was poured into 600 ml of water and the colorless crystals were filtered off. Melting point: 89° C.

(c) 3-Ethyl-2-ethylimino-4-(3-n-butylsulfamoyl-4-chlorophenyl)-1,3-thiazolidine-4-ol-hydrochloride 6.4 g of 3'-n-butylsulfamoyl-2,4'-dichloroacetophenone and 2.7 g of ground 1,3-diethylthiourea were reacted as prescribed in Example 12. With the addition of 200 ml of diisopropyl ether, the oily end product was precipitated and the solvent was decanted. The amorphous residue was dissolved in 100 ml of water and liophylized. Colorless solid body, decomposition beginning at 130° C., $\bar{\gamma}$ C=N 1620 cm$^{-1}$.

EXAMPLE 75

4-(3-tert.-Butylsulfamoyl-4-chlorophenyl)-3-methyl-2-methylimino-1,3-thiazolidine-4-ol-hydrochloride (a) 3-tert.-Butylsulfamoyl-4-chlorobenzoic acid To a mixture of 36.5 g (0.5 mol) of tert.-butylamine and 250 ml of ethanol were added 25.5 g (0.1 mol) of 4-chloro-3-chlorosulfonylbenzoic acid in small portions while stirring and cooling, the reaction temperature being maintained at about 30° C. After a dwelling time over night at room temperature, the solvent was distilled off, the residue was dissolved in about 200 ml of water, the pH was adjusted to 1 with concentrated HCl and the crystals were filtered off. Melting point: 250° C.

When reacting and working up correspondingly, there were obtained from 0.1 mol of 4-chloro-3-chlorosulfonylbenzoic acid and (a) 0.5 mol of n-butyl amine
3-n-butylsulfamoyl-4-chlorobenzoic acid, melting point: 134° C. (from ethanol/water)

(b) 0.5 mol of cyclohexyl amine
4-chloro-3-cyclohexylsulfamoyl-benzoic acid, melting point: 179°–180° C.

(c) 0.12 mol of o-chlorobenzyl amine and 0.4 mol of triethyl amine
4-chloro-3-o-chlorobenzylsulfamoylbenzoic acid, melting point: 195°–197° C.

(d) 0.12 mol of β-phenylethyl amine and 0.4 mol of triethyl amine
4-chloro-3-β-phenethylsulfamoylbenzoic acid, melting point: 123° C. (from toluene and active charcoal)

(e) 75 ml of 40% aqueous dimethyl amine solution
4-chloro-3-dimethylsulfamoylbenzoic acid, melting point: 242° C.

(f) 0.5 mol of diethyl amine
4-chloro-3-diethylsulfamoylbenzoic acid, melting point: 162° C.

(g) 0.5 mol of dipropyl amine
4-chloro-3-dipropylsulfamoylbenzoic acid, melting point: 145° C.

(h) 0.5 mol of di-n-butyl amine
4-chloro-3-di-n-butylsulfamoylbenzoic acid, melting point: 73°–75° C. (from methylcyclohexane)

(i) 0.4 mol of cyclohexyl-N-methyl amine
4-chloro-3-N-cyclohexyl-N-methylsulfamoylbenzoic acid, melting point: 157° C.

(j) 0.5 mol of piperidine
4-chloro-3-N-piperidinosulfonylbenzoic acid, melting point: 213° C.

(k) 0.4 mol of morpholine
4-chloro-3-N-morpholinosulfonylbenzoic acid, melting point: 187° C. (from ethanol/water).

(b) 3-tert.-Butylsulfamoyl-4-chlorobenzoylchloride 29 g of tert.-butylsulfamoyl-4-chlorobenzoic acid were reacted as prescribed in Example 74(a) and the residue was crystallized under petroleum ether after distilling off thionyl chloride. Colorless crystals, melting point: 97° C.

(c) 3'-tert.-Butylsulfamoyl-2,4'-dichloroacetophenone 16 g of 3-tert.-butylsulfamoyl-4-chlorobenzoyl chloride were reacted as prescribed in Example 66(b) with a solution of diazomethane in diisopropyl ether, sparingly soluble 3'-tert.-butylsulfamoyl-4'-chlorodiazoacetophenone being separated. The crystals were filtered and converted as prescribed in Example 66(b) with concentrated HCl in diethyleneglycol dimethyl ether to yield 3'-tert.-butyl-2,4'-dichloroacetophenone. Colorless crystals, melting point: 159° C.

(d) 4-(3-tert.-Butylsulfamoyl-4-chlorophenyl)-3-methyl-2-methyl-imino-1,3-thiazolidine-4-ol-hydrochloride 4.8 g of 3'-tert.-butylsulfamoyl-2,4'-dichloroacetophenone and 1.5 g of 1,3-dimethylthiourea were reacted as prescribed in Example 23 and the end product was filtered off with the addition of 30 ml of ethyl acetate. Colorless crystals, melting point: 288° C. (decomposition).

EXAMPLE 76

4-(4-Chloro-3-cyclopentylmethylsulfamoylphenyl)-3-methyl-2-methylimino-1,3-thiazolidine-4-ol 8.8 g of 4-(4-chloro-3-chlorosulfonylphenyl)-3-methyl-2-methylimino-1,3-thiazolidine-4-ol-hydrobromide were introduced portionwise at 20° C. in a stirred mixture of 4 g of cyclopentylmethyl amine, 8 g of triethyl amine and 100 ml of ethanol and the reaction mixture was allowed to stand over night. The solvent was distilled off under reduced pressure and the amorphous end product was crystallized under 80 ml of water. Colorless solid body, decomposition beginning at 80° C., $\bar{\gamma}$ C=N 1620 cm$^{-1}$.

EXAMPLE 77

4-(4-Chloro-3-β-dimethylaminoethylsulfamoylphenyl)-3-methyl-2-methylimino-1,3-thiazolidine-4-ol 6 g of 4-(4-chloro-3-chlorosulfonylphenyl)-3-methyl-2-methylimino-1,3-thiazolidine-4-ol-hydrobromide were reacted as prescribed in Example 76 with 1.8 g of β-dimethyl-aminoethyl amine and 6 g of triethyl amine in 100 ml of ethanol and worked up. The amorphous residue was treated with water and saturated sodium carbonate solution. Colorless solid body, decomposition beginning at 115° C., $\bar{\gamma}$ C=N 1620 cm$^{-1}$.

EXAMPLE 78

4-[4-Chloro-3-(2-methoxypropylsulfamoyl)-phenyl]-3-methyl-2-methylimino-1,3-thiazolidine-4-ol 6.5 g of 4-(4-chloro-3-chlorosulfonylphenyl)-3-methyl-2-methylimino-1,3-thiazolidine-4-ol-hydrobromide were reacted as prescribed in Example 76 with 5 g of 2-methoxypropyl amine in 100 ml of ethanol and worked up. Colorless crystalline solid substance, melting point: 148° C. (acetonitrile/active charcoal).

EXAMPLE 79

4-(3-Allylsulfamoyl-4-chlorophenyl)-3-methyl-2-methylimino-1,3-thiazolidine-4-ol 8.7 g of 4-(4-chloro-3-chlorosulfonylphenyl)-3-methyl-2-methylimino-1,3-thiazolidine-4-ol-hydrobromide were reacted as prescribed in Example 76 with 1.5 g of allyl amine and 4 g of triethyl amine in 50 ml of ethanol and worked up. The water was decanted and the amorphous end product was crystallized under diethyl ether. Colorless solid body, melting point: 146° C. (decomposition).

EXAMPLE 80

4-(4-Chloro-3-cyclopropylsulfamoylphenyl)-3-methyl-2-methylimino-1,3-thiazolidine-4-ol 6.6 g of 4-(4-chloro-3-chlorosulfonylphenyl)-3-methyl-2-methylimino-1,3-thiazolidine-4-ol-hydrobromide were reacted as prescribed in Example 76 with 1.5 g of cyclopropyl amine and 4 g of triethyl amine in 50 ml of ethanol and worked up. Fair yellow crystals, melting point: 180° C. (decomposition).

EXAMPLE 81

4-(4-Chloro-3-cyclohexylsulfamoylphenyl)-3-methyl-2-methylimino-1,3-thiazolidine-4-ol-hydrochloride (a) 4-Chloro-3-cyclohexylsulfamoylbenzoylchloride 30 g of 4-chloro-3-cyclohexylsulfamoylbenzoic acid were reacted as prescribed in Example 74(a) with thionyl chloride and worked up analogously after HCl had finished to develop. Colorless crystals, melting point 119° C. (from diisopropyl ether.)

(b) 2,4'-Dichloro-3'-cyclohexylsulfamoylacetophenone 17 g of 4-chloro-3-cyclohexylsulfamoylbenzoyl chloride were reacted as prescribed in Example 66(b) with a solution of diazomethane in diisopropyl ether, the sparingly soluble 4'-chloro-3'-cyclohexylsulfamoyl-diazoacetophenone being separated. The crystals were filtered and converted according to Example 66(b) with concentrated HCl in diethyleneglycol dimethyl ether to yield the 2,4'-dichloro-3'-cyclohexylsulfamoylacetophenone. Colorless crystals, melting point: 117° C.

(c) 4-(4-Chloro-3-cyclohexylsulfamoylphenyl)-3-methyl-2-methyl-imino-1,3-thiazolidine-4-ol-hydrochloride 5 g of 2,4'-dichloro-3'-cyclohexylsulfamoylacetophenone were reacted as prescribed in Example 23 with 1.7 g of 1,3-dimethylthiourea. To the reaction mixture were added 30 ml of ethyl acetate and the end product was filtered off. Colorless crystals, melting point: 261° C. (decomposition).

EXAMPLE 82

4-(4-Chloro-3-cyclooctylsulfamoylphenyl)-3-methyl-2-methyl-imino-1,3-thiazolidine-4-ol-hydrochloride (a) 4-Chloro-3-cyclooctylsulfamoylbenzoyl chloride 25.5 g of 4-chloro-3-chlorosulfonylbenzoic acid were reacted as prescribed in Example 75(a) with 45 g of cyclooctyl amine and worked up. The crystallized 4-chloro-3-cyclooctylsulfamoylbenzoic acid so obtained was dried end reacted without further purification in thionyl chloride as prescribed in Example 74(a). Colorless crystals, melting point: 134° C.

(b) 2,4'-Dichloro-3'-cyclooctylsulfamoylacetophenone 18 g of 4-chloro-3-cyclooctylsulfamoylbenzoyl chloride were reacted as prescribed in Example 66(b) with a solution of diazomethane in diisopropyl ether, the 4'-chloro-3'-cyclooctylsulfamoyl-diazoacetophenone remaining in solution without being separated. The total of the reaction mixture was reacted with concentrated HCl in diethyleneglycol dimethyl ether as prescribed in Example 70(c), worked up analogously, whereupon 2,4'-dichloro-3'-cyclooctylsulfamoylacetophenone was obtained as colorless to fair yellow visquous oil.

(c) 4-(4-Chloro-3-cyclooctylsulfamoylphenyl)-3-methyl-2-methylimino-1,3-thiazolidine-4-ol-hydrochloride 5.2 g of 2,4'-dichloro-3'-cyclooctylsulfamoylacetophenone and 1.8 g of 1,3-dimethylthiourea were reacted as prescribed in Example 23. To the reaction mixture were added 30 ml of ethyl acetate and the end product was filtered off. Colorless crystals, melting point: 192° C. (decomposition).

EXAMPLE 83

4-(4-Chloro-3-phenylsulfamoylphenyl)-3-methyl-2-methylimino-1,3-thiazolidine-4-ol-hydrochloride (a) 4-'Chloro-3'-phenylsulfamoylacetophenone 12.6 g of 4'-chloro-3'-chlorosulfonylacetophenone were introduced, while stirring, in a mixture of 5.6 g of aniline, 7.5 g of triethyl amine and 100 ml of dioxane. The mixture was allowed to dwell over night at 20° C., it was heated to 60° C. during 30 minutes while stirring and the separated triethylamine-hydrochloride was separated. The filtrate was concentrated under reduced pressure and the residue was crystallized under water. Colorless crystals (from isopropanol/active charcoal), melting point: 142° C.

(b) 2-Bromo-4'-chloro-3'-phenylsulfamoylacetophenone 8.8 g of copper-II-bromide in form of a fine powder were heated to boiling temperature in 75 ml of ethyl acetate and to the thoroughly stirred suspension was added a solution of 6.3 g of 4'-chloro-3'-phenylsulfamoylacetophenone in 75 ml of chloroform. The mixture was boiled at the reflux cooler while continuing thorough stirring until the black copper-II-bromide had disappeared and had turned into the colorless copper-I-bromide (about 6 hours). The colorless CuBr was filtered off and the solvent was evaporated under reduced pressure. Colorless crystals (from isopropanol/active charcoal), melting point: 154° C.

(c) 4-(4-Chloro-3-phenylsulfamoylphenyl)-3-methyl-2-methylimino-1,3-thiazolidine-4-ol-hydrobromide 5.2 g of 2-bromo-4'-chloro-3'-phenylsulfamoylacetophenone and 1.5 g of 1,3-dimethylthiourea were reacted as prescribed in Example 23 and the precipitated end product was filtered off. Colorless crystals, melting point: 82° C. (decomposition).

EXAMPLE 84

4-(3-Benzhydrylsulfamoyl-4-chlorophenyl)-3-methyl-2-methyl-imino-1,3-thiazolidine-4-ol 6.5 g of 4-(4-chloro-3-chlorosulfonylphenyl)-3-methyl-2-methylimino-1,3-thiazolidine-4-ol-hydrobromide were reacted as prescribed in Example 76 with 2.7 g of benzhydrylamine and 4 g of triethyl amine and worked up. Colorless solid body, decomposition beginning at 103° C., $\bar{\gamma}$ C=N 1620 cm$^{-1}$.

EXAMPLE 85

4-(4-Chloro-3-$\beta$-phenethylsulfamoylphenyl)-3-methyl-2-methylimino-1,3-thiazolidine-4-ol-hydrochloride (a) 4-Chloro-3-$\beta$-phenethylsulfamoylbenzoyl chloride 30 g of 4-chloro-3-$\beta$-phenethylsulfamoylbenzoic acid were reacted as prescribed in Example 74(a) in 200 ml of thionyl chloride and worked up. Melting point: 112° C.

(b) 4'-Chloro-3'-$\beta$-phenethylsulfamoyl-diazoacetophenone 18 g of 4-chloro-3-$\beta$-phenethylsulfamoylbenzoyl chloride were reacted as prescribed in Example 66(b) with diazomethane in diethyl ether and the crystalline precipitate was filtered off. Melting point: 128° C. (decomposition).

(c) 2,4'-Dichloro-3'-$\beta$-phenethylsulfamoylacetophenone 15 g of 4'-chloro-3'-$\beta$-phenethylsulfamoyl-diazoacetophenone were reacted as prescribed in Example 66(b) with 50 ml of concentrated HCl in 100 ml of diethyleneglycol dimethyl ether and worked up. Colorless crystals, melting point: 127° C.

(d) 4-(4-Chloro-3-$\beta$-phenethylsulfamoylphenyl)-3-methyl-2-methyl-imino-1,3-thiazolidine-4-ol-hydrochloride 5.5 g of 2,4'-dichloro-3'-$\beta$-phenethylsulfamoylacetophenone were reacted as prescribed in Example 23 with 1.5 g of 1,3-dimethylthiourea and the crystals were filtered. Melting point: 155° C.

EXAMPLE 86

4-(4-Chloro-3-o-chlorobenzylsulfamoylphenyl)-3-methyl-2-methylimino-1,3-thiazolidine-4-ol-hydrobromide (a) 4'-Chloro-3'-o-chlorobenzylsulfamoylacetophenone 25.5 g of 4'-chloro-3'-chlorosulfonylacetophenone were reacted with 16 g of o-chloro-benzyl amine and 25.5 g of triethyl amine and worked up. Colorless crystals from isopropanol (active charcoal), melting point: 102° C.

(b) 4-(4-Chloro-3-o-chlorobenzylsulfamoylphenyl)-3-methyl-2-methylimino-1,3-thiazolidine-4-ol-hydrobromide 7.2 g of 4'-chloro-3'-o-chlorobenzylsulfamoylacetophenone were reacted as prescribed in Example 1(a) with 3.2 g of bromine and the solvent was distilled off. The 2-bromo-4'- without further purification according to Example 23 with 2.3 g of 1,3-dimethylthiourea and worked up. Colorless crystals, melting point: 165° C. (decomposition)

EXAMPLE 87

4-(4-Chloro-3-o-chlorobenzylsulfamoylphenyl)-3-methyl-2-methylimino-1,3-thiazolidine-4-ol (a) 8.2 g of 4-(4-chloro-3-o-chlorobenzylsulfamoylphenyl)-3-methyl-2-methylimino-1,3-thiazolidine-4-ol-hydrobromide were treated in the manner described in Example 2(c) with aqueous sodium bicarbonate and the end product was filtered. Colorless crystals, melting point: 169° C.

(b) 6.6 g of 4-(4-chloro-3-chlorosulfonyl)-3-methyl-2-methyl-imino-1,3-thiazolidine-4-ol-hydrobromide were reacted as prescribed in Example 76 with 2.5 g of o-chlorobenzyl amine and 4 g of triethyl amine and worked up. The visquous residue contained in water was crystallized under a small amount of ethanol. Colorless crystals, melting point: 168°-169° C.

EXAMPLE 88

4-(4-Chloro-3-o-chlorobenzylsulfamoylphenyl)-3-methyl-2-methylimino-1,3-thiazolidine-4-ol-hydrochloride 8 g of 4-(4-chloro-3-o-chlorobenzylsulfamoylphenyl)-3-methyl-2-methylimino-1,3-thiazolidine-4-ol were reacted as prescribed in Example 3(c) with ethanolic HCl solution and the end product was precipitated by adding ethyl acetate. Colorless crystals, melting point: 170° C. (decomposition).

EXAMPLE 89

3-Ethyl-2-ethylimino-4-(4-chloro-3-o-chlorobenzylsulfamoylphenyl)-1,3-thiazolidine-4-ol-hydrochloride 30 g of 4-chloro-3-o-chlorobenzylsulfamoylbenzoic acid were reacted as prescribed in Example 74(a) and the residue was crystallized after distilling off thionyl chloride under petroleum ether. Colorless crystals, melting point: 125°-127° C.

(b) 2,4'-Dichloro-3'-o-chlorobenzylsulfamoylacetophenone 19 g of 4-chloro-3-o-chlorobenzylsulfamoylbenzoyl chloride were reacted as prescribed in Example 66(b)

with diazomethane in diethyl ether, the 4'-chloro-3'-o-chlorobenzylsulfamoyl-diazoacetophenone remaining in solution without being separated. To the total of the reaction mixture, there was added, according to Example 70(c) concentrated HCl in diethylene glycol dimethyl ether and the mixture was worked up. The oily residue crystallized in the course of 1–3 days. It was triturated under diisopropyl ether and the crystals were filtered off. Melting point: 94° C.

(c) 3-Ethyl-2-ethylimino-4-(4-chloro-3-o-chlorobenzyl-sulfamoyl-phenyl-1,3-thiazolidine-4-ol-hydrochloride 7.8 g of 2,4'-dichloro-3'-o-chlorobenzylsulfamoylacetophenone and 2.5 g of 1,3-diethylthiourea were reacted as prescribed in Example 12 and worked up. Colorless crystals, decomposition beginning at 94° C., $\bar{\gamma}$ C=N 1615 cm$^{-1}$.

EXAMPLE 90

4-(4-Chloro-3-o-chlorobenzylsulfamoylphenyl)-3-propyl-2-propylimino-1,3-thiazolidine-4-ol-hydrobromide 7.2 g of 4'-chloro-3'-o-chlorobenzylsulfamoylacetophenone were reacted with 3.2 g of bromine according to Example 1(a), the solvent was distilled off, the 2-bromo-4'-chloro-3'-o-chlorobenzylacetophenone so obtained was reacted without further purification according to Example 23 with 3 g of 1,3-dipropylthiourea and the end product was filtered off. Colorless crystals, melting point: 193°–194° C. (decomposition).

EXAMPLE 91

4-(4-Chloro-3-o-chlorobenzylsulfamoylphenyl)-3-propyl-2-propyl-imino-1,3-thiazolidine-4-ol-hydrochloride 9 g of 4-(4-chloro-3-o-chlorobenzylsulfamoylphenyl)-3-propyl-2-propylimino-1,3-thiazolidine-4-ol-hydrobromide were reacted with 4 g of triethyl amine in 250 ml of methanol, the reaction mixture was stirred for 1 hour at room temperature and the solvent was distilled off under reduced pressure. The residue was introduced into 100 ml of water and 4-(4-chloro-3-o-chlorobenzylsulfamoylphenyl)-3-propyl-2-propylimino-1,3-thiazolidine-4-ol were extracted with 100 ml of ethyl acetate. The organic phase was dried over sodium sulfate, the solvent was distilled off under reduced pressure and the residue was dissolved in 30 ml of ethanol. After acidifying with 15% ethanolic hydrochloric acid, the end product was precipitated with diethyl ether. Colorless crystals, melting point: 167° C.

EXAMPLE 92

4-[4-Chloro-3-(2,4-dimethoxybenzylsulfamoyl)-phenyl]-3-methyl-2-methylimino-1,3-thiazolidine-4-ol-hydrochloride 8.8 g of 4-(4-chloro-3-chlorosulfonylphenyl)-3-methyl-2-methylimino-1,3-thiazolidine-4-ol-hydrobromide were reacted as prescribed in Example 76 with 5 g of triethyl amine and 3.5 g of 2,4-dimethoxybenzyl amine and worked up. After treating with water, the amorphous 4-[4-chloro-3-(2,4-dimethoxybenzylsulfamoyl)-phenyl]-3-methyl-2-methylimino-1,3-thiazolidine-4-ol was extracted with 70 ml of ethyl acetate, dried over sodium sulfate and the solvent was acidified with ethanolic hydrochloric acid (15%). The amorphous precipitated end product was crystallized under isopropanol. Melting point: 163° C. (decomposition).

EXAMPLE 93

4-[4-Chloro-3-(3,4-methylenedioxybenzylsulfamoyl)-phenyl]-3-methyl-2-methylimino-1,3-thiazolidine-4-ol 6.5 g of 4-(4-chloro-3-chlorosulfonylphenyl)-3-methyl-2-methylimino-1,3-thiazolidine-4-ol-hydrobromide were reacted as prescribed in Example 76 with 2.4 g of 3,4-methylenedioxybenzyl amine and 3.5 g of triethyl amine and worked up. Colorless crystals from isopropanol, melting point: 131°–132° C. (decomposition).

EXAMPLE 94

4-[4-Chloro-3-(2-furylmethylsulfamoyl)-phenyl]-3-methyl-2-methylimino-1,3-thiazolidine-4-ol 6.5 g of 4-(4-chloro-3-chlorosulfonylphenyl)-3-methyl-2-methylimino-1,3-thiazolidine-4-ol-hydrobromide were reacted as prescribed in Example 76 with 1.5 g of 2-furylmethyl amine and 3.5 g of triethyl amine and worked up. Melting point: 154° C. (decomposition).

EXAMPLE 95

4-[4-Chloro-3-(2-picolylsulfamoyl)-phenyl]-3-methyl-2-methyl-imino-1,3-thiazolidine-4-ol 8.8 g of 4-(4-chloro-3-chlorosulfonylphenyl)-3-methyl-2-methylimino-1,3-thiazolidine-4-ol-hydrobromide were reacted with 3.0 g of 2-picolyl amine and 5 g of triethyl amine as prescribed in Example 76 and the end product precipitating as crystals was filtered off. Melting point: 166° C. (decomposition).

EXAMPLE 96

4-[4-Chloro-3-(3-picolylsulfamoyl)-phenyl]-3-methyl-2-methylimino-1,3-thiazolidine-4-ol 8.8 g of 4-(4-chloro-3-chlorosulfonylphenyl)-3-methyl-2-methylimino-1,3-thiazolidine-4-ol-hydrobromide were reacted with 3.0 g of 3-picolyl amine and 5 g of triethyl amine according to Example 76, the solvent was distilled off under reduced pressure and the residue was taken up in 70 ml of water. Three extractions followed with 60 ml of ethyl acetate, the organic phase was dried over sodium sulfate and the solvent was evaporated under reduced pressure. The residue crystallized under diisopropyl ether. Melting point: 152°–153° C.

EXAMPLE 97

4-(4-Chloro-3-dimethylsulfamoylphenyl)-3-methyl-2-methylimino-1,3-thiazolidine-4-ol-hydrobromide (a) 4'-Chloro-3'-dimethylsulfamoylacetophenone To a stirred mixture of 10 ml of 40% dimethyl amine solution and 60 ml of methanol, there were added, portionswise, 5.1 g of 4'-chloro-3'-chlorosulfonylacetophenone, so that the reaction temperature did not exceed 30° C. The reaction mixture was stirred for 3 hours at room temperature and 15 minutes at 60° C. After cooling, the reaction mixture was poured into 200 ml of water and the crystals were filtered off. Melting point: 108° C.

(b) 2-Bromo-4'-chloro-3'-dimethylsulfamoylacetophenone 7.9 g of 4'-chloro-3'-dimethylsulfamoylacetophenone were reacted according to Example 1(a) with 4.8 g of bromine and worked up. Colorless crystals from isopropanol, melting point: 98° C.

(c) 4-(4-Chloro-3-dimethylsulfamoylphenyl)-3-methyl-2-methylimino-1,3-thiazolidine-4-ol-hydrobromide (c1) 6.8 g of 2-bromo-4'-chloro-3'-dimethylsulfamoylacetophenone and 2.2 g of 1,3-dimethylthiourea were reacted as prescribed in Example 23 and the end product was precipitated by adding 20 ml of ethyl acetate. Colorless crystals, melting point: 161° C.

(c2) To a solution of 6.4 g of 2-bromo-4'-chloro-3'-dimethylsulfamoylacetophenone in 28 ml of methanol were added dropwise, at a reaction temperature of 5° C., a solution of 0.6 g of sodium borohydride in 5 ml of methanol and the solution was then stirred for 1 hour at room temperature. The reaction mixture was acidified while cooling (+5° C.) with 2 N HCl and the solvent was distilled off under reduced pressure. After adding 70 ml of water, extraction followed with 200 ml of diethyl ether, the organic phase was dried over sodium sulfate, the solvent was distilled off and 2-bromo-1-(4-chloro-3-dimethylsulfamoylphenyl)-ethanol was obtained as fair yellow to colorless oil.

(c3) 6.4 g of 2-bromo-1-(4-chloro-3-dimethylsulfamoylphenyl)-ethanol were reacted as prescribed in Example 23 with 2.1 g of 1,3-dimethylthiourea and 2-(4-chloro-3-dimethylsulfamoylphenyl)-2-hydroxyethyl-N,N-dimethylisothiouronium-bromide was precipitated with 200 ml of diisopropyl ether. The highly hygroscopic crystals ($\bar{\gamma}$ C=N 1620 cm$^{-1}$ in chloroform) were rapidly filtered off and stored in the exsiccator.

(c4) 4.5 g of 2-(4-chloro-3-dimethylsulfamoylphenyl)-2-hydroxyethyl-N,N-dimethylisothiuronium-bromide were dissolved in 200 ml of methylene chloride and after adding 40 g of active manganese dioxide, stirred at room temperature for 30 hours. The organic precipitate was filtered off and the solvent was distilled off under reduced pressure. The amorphous residue of the 4-(4-chloro-3-dimethylsulfamoylphenyl)-3-methyl-2-methylimino-1,3-thiazolidine-4-ol-hydrobromide was crystallized under ethyl acetate heated to 40° C.

EXAMPLE 98

4-(4-Chloro-3-dimethylsulfamoylphenyl)-3-methyl-2-methylimino-1,3-thiazolidine-4-ol 9.4 g of 4-(4-chloro-3-dimethylsulfamoylphenyl)-3-methyl-2-methylimino-1,3-thiazolidine-4-ol-hydrobromide were reacted according to Example 2(c) and the amorphous precipitate of the end product was crystallized under boiling diisopropyl ether. Colorless crystals from ethyl butylate, melting point: 157°–158° C.

EXAMPLE 99

4-(4-Chloro-3-dimethylsulfamoylphenyl)-3-methyl-2-methylimino-1,3-thiazolidine-4-ol-hydrochloride (a) 12 g of 4-(4-chloro-3-dimethylsulfamoylphenyl)-3-methyl-2-methylimino-1,3-thiazolidine-4-ol were reacted as prescribed in Example 3(c) and worked up. Colorless crystals, melting point: 169° C. (decomposition).

(b) 5.2 g of 4-chloro-3-dimethylsulfamoylacetophenone were stirred in a mixture of 100 ml of anhydrous carbon tetrachloride and 2.6 g of sulfuryl chloride with the exclusion of air humidity for 2 hours at room temperature and then boiled for 6 hours under reflux. The solvent was distilled off, the residue was decomposed under ice water and 2,4'-dichloro-3'-dimethylsulfamoylacetophenone was extracted with 100 ml of ethyl acetate. After drying the organic phase over sodium sulfate, the solvent was distilled off, the residue was reacted with 2.0 g of 1,3-dimethylthiourea according to Example 23 and crystalline 4-(4-chloro-3-dimethylsulfamoylphenyl)-3-methyl-2-methylimino-1,3-thiazolidine-4-ol-hydrochloride was filtered off.

EXAMPLE 100

4-(4-Chloro-3-dimethylsulfamoylphenyl)-3-methyl-2-methylimino-1,3-thiazolidine-4-ol-methylsulfonate (a) 4-Chloro-3-dimethylsulfamoylbenzoyl chloride 26.4 g of 4-chloro-3-dimethylsulfamoylbenzoic acid were reacted and worked up as prescribed in Example 74(a). Melting point: 103°–105° C.

(b) 4'-Chloro-3'-dimethylsulfamoyl-diazoacetophenone 14.1 g of 4-chloro-3-dimethylsulfamoylbenzoyl-chloride were reacted as prescribed in Example 66(b) with diazomethane in diethyl ether and the crystalline product was filtered off. Melting point: 136°–137° C. (decomposition).

(c) Methanesulfonic acid-(4'-chloro-3'-dimethylsulfamoylacetophenone-2-yl)-ester 5 g of 4'-chloro-3'-dimethylsulfamoyl-diazoacetophenone were introduced portionwise into 20 ml of ice-cold and stirred methanesulfonic acid and stirred for 30 minutes at room temperature. 100 ml of water were added and the crystals were filtered off. Melting point: 116° C.

(d) 4-(4-Chloro-3-dimethylsulfamoylphenyl)-3-methyl-2-methylimino-1,3-thiazolidine-4-ol-methylsulfonate 2 g of methanesulfonic acid-(4'-chloro-3'-dimethylsulfamoylacetophenone-2-yl)-ester and 0.7 g of 1,3-dimethylthiourea were reacted as prescribed in Example 23 and the crystalline end product was filtered off. Melting point: 166° C. (decomposition).

EXAMPLE 101

3-Ethyl-2-ethylimino-4-(4-chloro-3-dimethylsulfamoylphenyl)-1,3-thiazolidine-4-ol-hydrobromide 6.8 g of 2-bromo-4'-chloro-3'-dimethylsulfamoylacetophenone and 2.7 g of 1,3-diethylthiourea were reacted as prescribed in Example 23. The solvent was decanted and the oily precipitate of the end product was crystallized under fresh acetone. Colorless solid body, decomposition beginning at 154° C., $\bar{\gamma}$ C=N 1610 cm$^{-1}$.

EXAMPLE 102

3-Ethyl-2-ethylimino-4-(4-chloro-3-dimethylsulfamoylphenyl)-1,3-thiazolidine-4-ol-hydrochloride 10 g of 3-ethyl-2-ethylimino-4-(4-chloro-3-dimethylsulfamoylphenyl)-1,3-thiazolidine-4-ol-hydrobromide were reacted according to Example 2(c) and the yellow precipitate of 3-ethyl-2-ethylimino-4-(4-chloro-3-dimethylsulfamoylphenyl)-1,3-thiazolidine-4-ol was rapidly filtered off. The compound so obtained was treated according to Example 3(c) with ethanolic hydrochloric acid and the end product was precipitated by adding diisopropyl ether. The solvent was decanted, 200 ml of water were added to the amorphous residue and the aqueous solution was lyophilized. Colorless amorphous solid body, decomposition beginning at 134° C., $\bar{\gamma}$ C=N 1615 cm$^{-1}$.

EXAMPLE 103

4-(4-Chloro-3-dimethylsulfamoylphenyl)-3-propyl-2-propylimino-1,3-thiazolidine-4-ol-hydrochloride 6.8 g of 2-bromo-4'-chloro-3'-dimethylsulfamoylacetophenone were reacted according to Example 23 with 3.3 g of 1,3-dipropylthiourea. After adding 200 ml of diethyl ether, 4-(4-chloro-3-dimethylsulfamoylphenyl)-3-propyl-2-propylimino-1,3-thiazolidine-4-ol-hydrobromide was separated as an oil. The solvent was decanted, the product was dissolved in 30 ml of water and extracted with 100 ml of ethyl acetate. After drying over sodium sulfate, the solvent was distilled off under reduced pressure, the amorphous residue was dissolved in 30 ml of ethanol and acidified with ethanolic hydrochloric acid. The solvent was distilled off, the residue was dissolved in 40 ml of water and the end product was obtained by lyophilization. Colorless amorphous solid body, decomposition beginning at 128° C., $\bar{\gamma}$ C=N 1615 cm$^{-1}$.

EXAMPLE 104

4-(4-Chloro-3-dimethylsulfamoylphenyl)-3-cyclohexyl-2-cyclohexylimino-1,3-thiazolidine-4-ol (a) 4'-Chloro-3'-dimethylsulfamoylacetophenone-2-thiol 1.34 g of thioacetic acid were dissolved under nitrogen atmosphere in 15 ml of ethanol and made exactly neutral by adding a 40% aqueous potassium hydroxide solution. Then, 4.8 g of 2-bromo-4'-chloro-3'-dimethylsulfamoylacetophenone were added to the solution and stirring followed for 30 minutes at room temperature. The reaction mixture was poured into 100 ml of water and crystalline 2-acetylthio-4'-chloro-3'-dimethylsulfamoylacetophenone was filtered off. Melting point: 71° C. The compound so obtained was introduced into 35 ml of a 5% aqueous sodium hydroxide solution and the solution was stirred under nitrogen atmosphere for 45 minutes at room temperature. The solution was adjusted to pH 1 with 2 N hydrochloric acid and the end product was filtered off. Fair yellow crystals from ethanol, melting point: 93°-95° C.

(b) 4-(4-Chloro-3-dimethylsulfamoylphenyl)-3-cyclohexyl-2-cyclohexylimino-1,3-thiazolidine-4-ol To a solution of 2.9 g of 4'-chloro-3'-dimethylsulfamoylphenylacetophenone-2-thiol in 30 ml of anhydrous tetrahydrofurane were added dropwise, with the exclusion of air humidity a solution of 2 g of dicyclohexylcarbodiimide in 20 ml of anhydrous tetrahydrofurane, the reaction temperature being maintained between 10° and 15° C. The reaction mixture was stirred for 20 hours at room temperature, the solvent was distilled off under reduced pressure and the residue was crystallized under 40 ml of water. Colorless solid body, decomposition beginning at 89° C., $\bar{\gamma}$ C=N 1625 cm$^{-1}$.

EXAMPLE 105

4-(4-Chloro-3-dimethylsulfamoylphenyl)-3-cyclohexyl-2-cyclohexylimino-1,3-thiazolidine-4-ol-hydrobromide 2.5 g of 4-(4-chloro-3-dimethylsulfamoylphenyl)-3-cyclohexyl-2-cyclohexylimino-1,3-thiazolidine-4-ol were dissolved in 10 ml of methanol and adjusted to pH 3 by adding dropwise 48% hydrobromic acid. The solvent was distilled off under reduced pressure and the amorphous end product was crystallized under diethyl ether. Colorless crystals, melting point: 131° C. (decomposition).

EXAMPLE 106

3-(4-Chloro-3-dimethylsulfamoylphenyl)-3-hydroxy-2,3,5,6-tetra-hydro-imidazo[2,1-b]thiazol-hydrobromide To 3 g of 2-bromo-1-imidazoline in 50 ml isopropanol were added 5.9 g of 4'-chloro-3'-dimethylsulfamoylacetophenone-2-thiol and the mixture was stirred for 10 hours at room temperature and a further 2 hours at 35° C. After cooling the end product was precipitated with 100 ml of diethyl ether and the solvent was decanted. The residue was stirred for 4 hours in 30 ml of acetone at room temperature and the crystalline precipitated was filtered off. Melting point: 155° C. (decomposition).

EXAMPLE 107

3-(4-Chloro-3-dimethylsulfamoylphenyl)-3-hydroxy-2,3,5,6-tetra-hydro-imidazo[2,1-b]thiazole 7.3 g of 3-(4-chloro-3-dimethylsulfamoylphenyl)-3-hydroxy-2,3,5,6-tetrahydro-imidazo[2,1-b]thiazol-hydrobromide were dissolved in 100 ml of water at 35°-40° C. After adding a solution of 6 g of sodium bicarbonate in 200 ml of water, the mixture was stirred for 15 minutes at room temperature and the end product was filtered off. Colorless crystals, melting point: 154° C. (decomposition).

EXAMPLE 108

4-(4-Chloro-3-diethylsulfamoylphenyl)-3-methyl-2-methylimino-1,3-thiazolidine-4-ol-hydrochloride (a) 4'-Chloro-3'-diethylsulfamoyl-diazoacetophenone 39 g of 4-chloro-3-diethylsulfamoylbenzoic acid were boiled under reflux in 200 ml of thionyl chloride until the development of HCl had finished and the thionyl chloride was then distilled off under reduced pressure. 4-chloro-3-diethylsulfamoylbenzoyl chloride was obtained as fair yellow oil.

16 g of the 4-chloro-3-diethylsulfamoylbenzoyl-chloride so obtained were reacted as prescribed in Example 66(b) with diazomethane in diisopropyl ether and crystalline 4'-chloro-3'-diethylsulfamoyl-diazoacetophenone was filtered off. Fair yellow crystals, melting point: 120° C. (decomposition).

(b) 3'-Diethylsulfamoyl-2,4'-dichloroacetophenone 12 g of 4'-chloro-3'-diethylsulfamoyl-diazoacetophenone were reacted as prescribed in Example 66(b) with concentrated HCl in diethyleneglycol dimethyl ether and worked up. Colorless crystals, melting point: 63°-65° C.

(c) 4-(4-Chloro-3-diethylsulfamoylphenyl)-3-methyl-2-methylimino-1,3-thiazolidine-4-ol-hydrochloride 4.8g of 3'-diethylsulfamoyl-2,4'-dichloroacetophenone and 1.5 g of 1,3-dimethylthiourea were reacted as prescribed in Example 23 and the crystalline end product was filtered off. Melting point: 165° C. (decomposition).

EXAMPLE 109

4-(4-Chloro-3-dipropylsulfamoylphenyl)-3-methyl-2-methylimino-1,3-thiazolidine-4-ol-hydrochloride (a) 2,4'-Dichloro-3'-dipropylsulfamoylacetophenone 43 g of 4-chloro-3-dipropylsulfamoylbenzoic acid were reacted as prescribed in Example 108(a) with thionyl chloride and worked up.

17 g of the 4-chloro-3-dipropylsulfamoylbenzoyl chloride so obtained as an oil were reacted according to Example 66(b) with diazomethane in diisopropyl ether, the 4'-chloro-3'-dipropylsulfamoyl-diazoacetophenone remaining in solution without crystallizing out. The ethereal solution was treated according to Example 70(c) with hydrochloric acid and worked up accordingly, 2,4'-dichloro-3'-dipropylsulfamoylacetophenone being obtained as colorless crystalline product. (Melting point: 76° C.).

(b) 4-(4-Chloro-3-dipropylsulfamoylphenyl)-3-methyl-2-methylimino-1,3-thiazolidine-4-ol-hydrochloride 4.8 g of 2,4'-dichloro-3'-dipropylsulfamoylacetophenone and 1.5 g of 1,3-dimethylthiourea were reacted as prescribed in Example 23 and worked up. Colorless crystals, melting point: 166° C. (decomposition).

EXAMPLE 110

3-Ethyl-2-ethylimino-4-(3-di-n-butylsulfamoyl-4-chlorophenyl)-1,3-thiazolidine-4-ol-hydrochloride (a) 3'-Di-n-butylsulfamoyl-2,4'-dichloroacetophenone 15 g of 3-di-n-butylsulfamoyl-4-chlorobenzoic acid were treated as prescribed in Example 108(a) with thionyl chloride and reacted.

18 g of the 3-di-n-butylsulfamoyl-4-chlorobenzoyl-chloride so obtained as an oil were reacted as prescribed in Example 70(c) in diethyl ether with diazomethane and then with concentrated HCl in diethyleneglycol dimethyl ether and worked up, 3'-di-n-butylsulfamoyl-2,4'-dichloroacetophenone being obtained in the form of colorless crystals having a melting point of 71° C.

(b) 3-Ethyl-2-ethylimino-4-(3-di-n-butylsulfamoyl-4-chloro-phenyl)-1,3-thiazolidine-4-ol-hydrochloride 7.0 g of 3'-di-n-butylsulfamoyl-2,4'-dichloro-acetophenone were reacted according to Example 12 with 2.7 g of 1,3-diethylthiourea and worked up. Colorless solid body, decomposition beginning at 139° C., $\gamma$C=N 1615 cm$^{-1}$.

EXAMPLE 111

4-(4-Chloro-3-N-cyclohexyl-N-methylsulfamoylphenyl)-3-methyl-2-methylimino-1,3-thiazolidine-4-ol-hydrochloride (a) 2,4'-Dichloro-3'-N-cyclohexyl-N-methylsulfamoylacetophenone 16 g of 4-chloro-3-N-cyclohexyl-N-methylsulfamoylbenzoic acid were reacted and worked up as prescribed in Example 108(a).

18 g of the 4-chloro-3-N-cyclohexyl-N-methylsulfamoylbenzoyl chloride so obtained as an oil were reacted as prescribed in Example 66(b) with diazomethane in diisopropyl ether and 4'-chloro-3'-N-cyclohexyl-N-methylsulfamoyl-diazoacetophenone (melting at 118° C.) were converted according to Example 66(b) into 2,4'-dichloro-3'-N-cyclohexyl-N-methylsulfamoylacetophenone. Colorless crystals, melting point: 84°–86° C.

(b) 4-(4-Chloro-3-N-cyclohexyl-N-methylsulfamoylphenyl)-3-methyl-2-methylimino-1,3-thiazolidine-4-ol-hydrochloride 5.4 g of 2,4'-dichloro-3'-N-cyclohexyl-N-methylsulfamoylacetophenone and 1.6 g of 1,3-dimethylthiourea were reacted as prescribed in Example 23 and worked up. Colorless crystals, melting point: 164° C. (decomposition).

EXAMPLE 112

3-Ethyl-2-ethylimino-4-(4-chloro-3-N-piperidinosulfonylphenyl)-1,3-thiazolidine-4-ol-hydrochloride (a) 2,4'-Dichloro-3'-N-piperidinosulfonylacetophenone 15 g of 4-chloro-3-N-piperidinosulfonylbenzoic acid were converted as prescribed in Example 108(a) into 4-chloro-3-N-piperidinosulfonylbenzoyl chloride which was then reacted according to Example 66(b) to yield 2,4'-dichloro-3'-N-piperidinosulfonylacetophenone. Colorless crystals, melting point: 134° C.

(b) 3-Ethyl-2-ethylimino-4-(4-chloro-3-N-piperidinosulfonylphenyl)-1,3-thiazolidine-4-ol-hydrochloride 5.1 g of 2,4'-dichloro-3'-N-piperidinosulfonylacetophenone and 2.0 g of 1,3-diethylthiourea were reacted and worked up as prescribed in Example 12. Colorless solid body, decomposition beginning at 110° C. $\gamma$C=N 1615 cm$^{-1}$.

EXAMPLE 113

3-Ethyl-2-ethylimino-4-(4-chloro-3-N-morpholinosulfonylphenyl)-1,3-thiazolidine-4-ol-hydrochloride (a) 4-Chloro-3-N-morpholinosulfonylbenzoyl chloride 30.6 g of 4-chloro-3-N-morpholinosulfonylbenzoic acid were reacted and worked up as prescribed in Example 74(a). Colorless crystals, melting point: 120°–122° C.

(b) 2,4'-Dichloro-3'-N-morpholinosulfonylacetophenone 17 g of 4-chloro-3-N-morpholinosulfonylbenzoyl chloride were reacted as prescribed in Example 66(b) with 4'-chloro-3'-N-morpholinosulfonyl-diazoacetophenone (fair yellow crystals, melting point: 186° C. (decomposition) to yield 2,4'-dichloro-3'-N-morpholinosulfonylacetophenone. Colorless crystals, melting point: 130° C.

(c) 3-Ethyl-2-ethylimino-4-(4-chloro-3-N-morpholinosulfonyl-phenyl)-1,3-thiazolidine-4-ol-hydrochloride 6.8 g of 2,4'-dichloro-3'-N-morpholinosulfonylacetophenone and 2.6 g of diethylthiourea were reacted as prescribed in Example 12, the end product was precipitated with diisopropyl ether and the solvent was decanted. The amorphous residue was dissolved in 100 ml of water and lyophilized. Colorless solid body, decomposition beginning at 139° C., $\gamma$C=N 1615 cm$^{-1}$.

EXAMPLE 114

4-(4-Chloro-3-N-methyl-N-phenylsulfamoylphenyl)-3-methyl-2-methylimino-1,3-thiazolidine-4-ol-hydrobromide (a) 4'-Chloro-3'-N-methyl-N-phenylsulfamoylacetophenone 6 g of 4'-chloro-3'-chlorosulfonylacetophenone were reacted and worked up as prescribed in Example 83(a). Colorless crystals, melting point: 80°–81° C.

(b) 2-Bromo-4'-chloro-3'-N-methyl-N-phenylsulfamoylacetophenone 9.6 g of 4′-chloro-3′-N-methyl-N-phenylsulfamoylacetophenone in 150 ml of chloroform were reacted as prescribed in Example 83(b) with 14 g of powdered copper-II-bromide in 150 ml of ethyl acetate and worked up. Colorless crystals from n-butanol/active charcoal, melting point: 144°–145° C.

(c) 4-(4-Chloro-3-N-methyl-N-phenylsulfamoylphenyl)-3-methyl-2-methylimino-1,3-thiazolidine-4-ol-hydrobromide 4 g of 2-bromo-4′-chloro-3′-N-methyl-N-phenyl-sulfamoylacetophenone were reacted as prescribed in Example 23 with 1.1 g of 1,3-dimethylthiourea and the end product was precipitated with diisopropyl ether. Colorless solid body, decomposition beginning at 98° C., $\bar{\gamma}$C=N 1630 cm$^{-1}$.

EXAMPLE 115

4-(3-N-Benzyl-N-methylsulfamoyl-4-chlorophenyl)-3-methyl-2-methylimino-1,3-thiazolidine-4-ol-hydrochloride (a) 3′-N-Benzyl-N-methylsulfamoyl-2,4′-dichloroacetophenone 25.5 g of 4-chloro-3-chlorosulfonylbenzoic acid were introduced in a stirred mixture of 60 ml of pyridine and 12.2 g of N-methyl-N-benzyl amine in such a way that the reaction temperature did not exceed 35° C. The mixture was stirred for 20 hours at room temperature and the solvent was distilled off. The residue was taken up in 200 ml of water, adjusted to pH 1 with 2 N HCl and the precipitate was extracted with 200 ml of ethyl acetate. After drying the organic phase over sodium sulfate, the solvent was distilled off, the amorphous residue of the 3-N-benzyl-N-methylsulfamoyl-4-chlorobenzoic acid was reacted according to Example 108(a) with thionyl chloride and worked up analogously. The 3-N-benzyl-N-methylsulfamoyl-4-chlorobenzoyl chloride obtained as an oil was reacted as prescribed in Example 66(b) with diazomethane in diisopropyl ether and the crystallized precipitate of 3′-N-benzyl-N-methyl-sulfamoyl-4′-chloro-diazoacetophenone (melting point 122° C. with decomposition) was converted as prescribed in Example 66(b) into 3′-N-benzyl-N-methylsulfamoyl-2,4′-dichloroacetophenone. Colorless crystals, melting point: 124° C.

(b) 4-(3-N-Benzyl-N-methylsulfamoyl-4-chlorophenyl)-3-methyl-2-methylimino-1,3-thiazolidine-4-ol-hydrochloride 5.3 g of 3′-N-benzyl-N-methylsulfamoyl-2,4′-dichloroacetophenone were reacted as prescribed in Example 23 with 1,3-dimethylthiourea and the crystallized end product was filtered off. Colorless crystals, melting point: 160° C. (decomposition).

EXAMPLE 116

4-[4-Chloro-3-N-(2-hydroxy-1-methyl-2-phenylethyl)-N-methylsulfamoyl-phenyl]-3-methyl-2-methylimino-1,3-thiazolidine-4-ol 4.3 g of 4-(4-chloro-3-chlorosulfonylphenyl)-3-methyl-2-methylimino-1,3-thiazolidine-4-ol-hydrobromide were reacted as prescribed in Example 76 with 4.3 g of ephedrine and 4.1 g of triethyl amine and worked up. Colorless solid body, decomposition beginning at 134° C., $\bar{\gamma}$C=N 1620 cm$^{-1}$.

EXAMPLE 117

4-[4-Chloro-3-N-(2-furylmethyl)-N-methylsulfamoylphenyl]-3-methyl-2-methylimino-1,3-thiazolidine-4-ol 4.4 g of 4-(4-chloro-3-chorosulfonylphenyl)-3-methyl-2-methylimino-1,3-thiazolidine-4-ol-hydrobromide were reacted analogously to Example 76 with 1.6 g of 2-furylmethyl-N-methylamine and 4 g of triethyl amine and worked up. Colorless solid body, decomposition beginning at 158° C. $\bar{\gamma}$C=N 1625 cm$^{-1}$.

EXAMPLE 118

3-(4-Chloro-3-dimethylsulfamoylphenyl)-3-hydroxy-2,3,4,5,6-tetrahydroimidazo-[2,1-b]thiazole-hydrobromide (a) 5-Bromo-2-chloroaniline 90 g of 5-bromo-2-chloronitrobenzene were hydrogenated in 500 ml of methanol at room temperature and under normal pressure with Raney-Nickel as catalyst and hydrogen. Colorless crystals, melting point: 47° C.

(b) 5-Bromo-2-chlorobenzenedimethylsulfonic acid amide 13.6 g of 5-bromo-2-chloroaniline were diazotized in 50 ml of concentrated hydrochloric acid at 0°–5° C. with 4.7 g of sodium nitrite in 19 ml of water. The solution obtained was added to a solution of 6.6 g of sodium bisulfite and 1.5 g of copper-II-chloride in 40 ml of water, the solution was stirred for 30 minutes, diluted with 100 ml of water and the crystalline 5-bromo-2-chlorobenzenesulfonic acid chloride was filtered off; it was introduced without further purification into a mixture of 70 ml of ethanol and 50 ml of aqueous concentrated dimethylamine solution. After standing overnight it was diluted with water and the colorless crystals were suction-filtered. Melting point: 87° C. (from diisopropyl ether).

(c) 3-(4-Chloro-3-dimethylsulfamoylphenyl)-3-hydroxy-2,3,5,6-tetrahydroimidazo[2,1-b] thiazole-hydrobromide To a thoroughly stirred solution of 0.05 mol of butyl-lithium in 150 ml of absolute tetrahydrofurane, 14.9 g of 5-bromo-2-chlorobenzenedimethylsulfonic acid amide in 100 ml of absolute tetrahydrofurane were added slowly at −45° C. with the exclusion of oxygen and air humidity and the solution was further stirred for 20 minutes at 31 40° C. To the so-obtained solution of 4-chloro-3-dimethylsulfamoyl-phenyllithium, a solution of 7 g of 5,6-dihydroimidazo [2,1-b]thiazole-3-(2H)-one in 200 ml of absolute tetrahydrofurane were added dropwise in the course of 60 minutes, the solution was stirred overnight at room temperature and the reaction mixture was treated under ice-cooling with 25 ml of saturated ammonium chloride solution. The precipitate was filtered off, the filtrate was dried over magnesium sulfate, and treated with dry hydrogen bromide. Colorless crystals, melting point: 153°–155° C. (decomposition).

In an analogous manner as described under Example 23, there were obtained in the following Examples:

EXAMPLE 119 from
4.9 g of 2-bromo-4′-chloro-3′-methylsulfamoylacetophenone and
1.8 g of 1-isopropyl-3-methyl thiourea 4-(4-chloro-3-methylsulfamoylphenyl)-2-iso-
propylimino-3-methyl-1,3-thiazolidine-4-ole hydrobromide,
melting point: 244° C. (decomposition),

EXAMPLE 120 from
5.1 g of 2-bromo-4'-chloro-3'-dimethylsulfamoylacetophenone and
1.8 g of 1-isopropyl-3-methylthiourea
4-(4-chloro-3-dimethylsulfamoylphenyl)-2-isopropylimino-3-methyl-1,3-thiazolidine-4-ole-hydrobromide,
melting point: 242° C. (decomposition),

EXAMPLE 121 from
6 g of 2-bromo-3'-benzylsulfamoyl-4'-chloroacetophenone
and
2 g of 1,3-diethylthiourea and following precipitation with diisopropyl ether,
3-ethyl-2-ethylimino-4-(3-benzyl-sulfamoyl-4-chlorophenyl)-1,3-thiazolidine-4-ole-hydrobromide,
melting point: 114° C. (decomposition),

EXAMPLE 122 from
6.3 g of 2-bromo-4'-chloro-3'-sulfamoylacetophenone
and
3.2 g of 1-ethyl-3-isobutylthiourea
3-ethyl-4-(4-chloro-3-sulfamoylphenyl)-2-isobutylimino-1,3-thiazolidine-4-ole-hydrobromide,
melting point: 187° C. (decomposition), which was converted with sodium bicarbonate solution as described in Example 28 into 3-ethyl-4-(4-chloro-3-sulfamoylphenyl)-2-isobutylimino-1,3-thiazolidine-4-ole (decomposition beginning at 125° C.). By treating with methanolic hydrochloric acid and following crystallization under acetone there was obtained the corresponding 3-ethyl-4-(4-chloro-3-sulfamoylphenyl)-2-isobutylimino-1,3-thiazolidine-4-ole-hydrochloride from this compound in ether.
Melting point: 175° C. (decomposition),

EXAMPLE 123 from
6.3 g of 2-bromo-4'-chloro-3'-sulfamoylaccetophenone and
2.6 g of 1-methyl-3-propargylthiourea (melting point: 65° C., prepared from 2.8 g of propargyl amine and 3.4 g of methyl mustard oil in 34 ml of toluene) in the presence of a small amount of methanol
4-(4-chloro-3-sulfamoylphenyl)-3-methyl-2-propargylimino-1,3-thiazolidine-4-ole-hydrobromide,
melting point: 168° C. (decomposition),

EXAMPLE 124 from
7.2 g of 2,4'-dibromo-3'-sulfamoylacetophenone and
2.1 g of 1,3-dimethylthiourea
4-(4-bromo-3-sulfamoylphenyl)-3-methyl-2-methylimino-1,3-thiazolidine-4-ole-hydrobromide,
melting point: 169° C. (decomposition). (Preparation of 2,4'-dibromo-3'-sulfamoylacetophenone:
5.35 g of 3'-amino-4'-bromoacetophenone, melting point: 113° C., were diazotized in 50 ml of semi-concentrated hydrochloric acid with 1.75 g of sodium nitrite at 0°–5° C. and then decomposed according to Meerwein with 62 ml of sulfur-dioxide-saturated glacial acetic acid solution and 2 g of copper-II-chloride-dihydrate. chloride-dihydrate. After the addition of 62 ml of water, the 4'-bromo-3'-chlorosulfonylacetophenone was obtained which melted at 107° C. and could be introduced without further purification into about 50 ml of liquid ammonia. After evaporation of the ammonia and treatment with water, 4'-bromo-3'-sulfamoylacetophenone were obtained which melted at 161° C.

In an analogous manner as described under Example 12, 4.8 g of 4'-bromo-3'-sulfamoylacetophenone were reacted with 2.8 g of bromine and the 2,4'-dibromo-3'-sulfamoylacetophenone was recrystallized from isopropanol.
Melting point: 179° C.).

EXAMPLE 125 from
7.2 g of 2,4'-dibromo-3'sulfamoylacetophenone and
3.5 g of 1-cyclohexyl-3-methylthiourea
4-(4-bromo-3-sulfamoylphenyl)-2-cyclohexylimino-3-methyl-1,3-thiazolidine-4-ole-hydrobromide,
melting point: 172° C., decomposition,

EXAMPLE 126 from
7.2 g of 2,4'-dibromo-3'-sulfamoylacetophenone and
3 g of 1-ethyl-3-isopropylthiourea and following precipitation with diisopropyl ether
the 3-ethyl-4-(4-bromo-3-sulfamoylphenyl)-2-isopropylimino-1,3-thiazolidine-4-ole-hydrobromide,
(decomposition beginning at 135° C.),

EXAMPLE 127 from
7.2 g of 2,4'-dibromo-3'-sulfamoylacetophenone and
3.2 g of 1,3-diallylthiourea and following precipitation with diisopropyl ether
the 3-allyl-2-allylimino-4-(4-bromo-3-sulfamoylphenyl)-1,3-thiazolidine-4-ole-hydrobromide,
melting point: 156° C. (decomposition),

EXAMPLE 128 from
3 g of 2-bromo-4'-fluoro-3'-sulfamoylacetophenone and
1 g of 1,3-dimethylthiourea
the 4-(4-fluoro-3-sulfamoylphenyl)-3-methyl-2-methylimino-1,3-thiazolidine-4-ole-hydrobromide,
melting point: 164° C. (decomposition). (Preparation of 2-bromo-4'-fluoro-3'-sulfamoylacetophenone:
(a) 39 g of 4'-fluoro-3'-nitroacetophenone, melting point: 44° C., were hydrogenated in 390 ml of methanol at 20 atm. and 40° C. in the presence of Raney-Nickel to give the 3'-amino-4'-fluoro-acetophenone, melting point: 70° C.).
(b) 4.9 g of 3'-amino-4'-fluoroacetophenone were diazotized in 25 ml of concentrated hydrochloric acid at 0° to 5° C. with a solution of 2.3 g of NaNO$_2$ in 5 ml of water and treated with a solution, prepared from 2.7 g of sodium bisulfite in 5 ml of water and 25 ml of concentrated hydrochloric acid and the oily 3'-chlorosulfonyl-4'-fluoroacetophenone was reacted with 20 ml of liquid ammonia to give the 4'-fluoro-3'-sulfamoylacetophenone, melting point: 135° C. from glacial acetic acid.

(c) 12.5 g of 4'-fluoro-3'-sulfamoylacetophenone were reacted as described in Example 12 with 9.2 g of bromine to give the 2-bromo-4'-fluoro-3'-sulfamoylacetophenone, melting point: 125° C.

EXAMPLE 129 from
3 g of 2-bromo-4'-fluoro-3'-sulfamoylacetophenone
and
1.2 g of 1,3-diethylthiourea,
the 3-ethyl-2-ethylimino-4-(4-fluoro-3-sulfamoylphenyl)-1,3-thiazolidine-4-ole-hydrobromide, decomposition beginning at 120° C.,

EXAMPLE 130 from
3.6 g of 2-bromo-4'-chloro-3'-propylsulfamoylacetophenone
and
1.1 g of 1,3-dimethylthiourea
the 4-(4-chloro-3-propylsulfamoylphenyl)-3-methyl-2-methylimino-1,3-thiazolidine-4-ole-hydrobromide, decomposition beginning at 120° C.
(Preparation of 2-bromo-4'-chloro-3'-propylsulfamoylacetophenone:
(a) 12.5 g of 4'-chloro-3'-chlorosulfonylacetophenone were reacted in 150 ml of ethanol with 18 g of n-propylamine and the 4'-chloro-3'-propylsulfamoylacetophenone was filtered off (melting point: 115° C. from a small amount of isopropanol).
(b) 13.8 g of 4'-chloro-3'-propylsulfamoylacetophenone were reacted as described in Example 1(a) with 8 g of bromine to give the 2-bromo-4'-chloro-3'-propylsulfamoylacetophenone, melting point: 96° C., from isopropanol).

EXAMPLE 131 from
6.2 g of 2-bromo-4'-chloro-3'-sulfamoylacetophenone
3.8 g of 1-methyl-4,4-pentamethylenethiosemicarbazide (prepared from methylisothiocyanate and N-aminohomopiperidine, melting point: 192° C.)
the 4-(4-chloro-3-sulfamoylphenyl)-3-methyl-4-hydroxy-1,3-thiazolidine-2-one-N,N-pentamethylenehydrazone-hydrobromide, melting point: 165° C., decomposition.

In an analogous manner to Example 15(b) there were obtained in the following Examples:

EXAMPLE 132 from
4.7 g of 2-bromo-4'-chloro-3'-sulfamoylacetophenone
and
2.2 g of 1-ethyl-3-cyclopropylthiourea (melting point: 106° C.), prepared from 9 g of ethylisothiocyanate and 5.7 g of cyclopropyl amine in toluene; the 3-ethyl-4-(4-chloro-3-sulfamoylphenyl)-2-cyclohexylimino-1,3-thiazolidine-4-ole-hydrobromide, which was converted after dissolution in water and with sodium bicarbonate solution in an analogous manner as to Example 2(c) into the 3-ethyl-4-(4-chloro-3-sulfamoylphenyl)-2-cyclopropylimino-1,3-thiazolidine-4-ole, melting point 125 C., decomposition,

EXAMPLE 133 from
4.7 g of 2-bromo-4'-chloro-3'-sulfamoylacetophenone
and
2.8 g of 1-ethyl-3-cyclohexylthiourea
the 3-ethyl-4-(4-chloro-3-sulfamoylphenyl)-2-cyclohexylimino-1,3-thiazolidine-4-ole-hydrobromide,
which was converted after dissolution in water in an analogous manner to Example 2(c) into the 3-ethyl-4-(4-chloro-3-sulfamoylphenyl)-2-cyclohexylimino-1,3-thiazolidine-4-ole, (decomposition beginning at 125° C.).

EXAMPLE 134 from
4.7 g of 2-bromo-4'-chloro-3'-sulfamoylacetophenone
and
2.8 g of 1-ethyl-3-(2-methoxypropyl)-thiourea
the 3-ethyl-4(-4-chloro-3-sulfamoylphenyl)-2-methoxypropylimino-1,3-thiazolidine-4-ole-hydrobromide,
which yielded a solid substance after dissolution in water and lyophilization, (decomposition beginning at 120° C.).

EXAMPLE 135 from
4.7 g of 2-bromo-4'-chloro-3'-sulfamoylacetophenone
and
2.7 g of 1-ethyl-3-(2-furylmethyl)-thiourea
the 3-ethyl-4-(4-chloro-3-sulfamoylphenyl)-2-(2-furylmethylimino)-1,3-thiazolidine-4-ole-hydrobromide,
which was converted in an analogous manner to Example 2(c) with aqueous NaHCO$_3$ solution into the 3-ethyl-4-(4-chloro-3-sulfamoylphenyl)-2-(2-furylmethylimino)-1,3-thiazolidine-4-ole, decomposition beginning at 115° C.).

EXAMPLE 136

4-(4-Chloro-3-cyclopentylmethylsulfamoylphenyl)-3-methyl-2-methylimino-1,3-thiazolidine-4-ole 6.7 g of 4-(4-Chloro-3-sulfamoylphenyl)-3-methyl 2-methylimino-1,3-thiazolidine-4-ole (Example 2) were introduced, while stirring, into a mixture of 10 ml of absolute dimethyl sulfoxide and 1.2 g of pulverized potassium hydroxide with the exclusion of nitrogen, the temperature being maintained between 8° C. and 12° C. by outward cooling. While cooling and stirring were maintained, 3.3 g of cyclopentylmethylbromide were added dropwise, the mixture was stirred for 10 hours at room temperature and precipitated with 100 ml of water. The oily residue was decanted, the amorphous product was solidified under 100 ml of fresh water, suction-filtered and washed with water several times. Yellow-brown solid substance, decomposition beginning at 72° C. The IR-spectrum was identical with that of Example 76.

EXAMPLE 137

4-(4-Chloro-3-o-chlorobenzylsulfamoylphenyl)-3-methyl-2-methylimino-1,3-thiazolidine-4-ole 6.7 g of 4-(4-chloro-3-sulfamoylphenyl)-3-methyl-2-methylimino-1,3-thiazolidine-4-ole (Example 2) were suspended in 67 ml of absolute methanol, while stirring to which a freshly prepared solution from 0.5 g of sodium in 15 ml of absolute methanol was added. 4.1 g of o-chloro-benzyl bromide were added at +10° C. while stirring and the reaction mixture was stirred for 24 hours at room temperature and for a further 2 hours at 38° C. The mixture was concentrated to a half under reduced pressure, poured into 100 ml of stirred water, filtered off and washed with water several times. Colorless substance, melting point: 161° C. (decomposition). The IR-spectrum was identical with that of Example 87.

According to the operational method (c) and in an analogous manner to the precription given in Example 106 there were obtained the following compounds of the formula I of the invention as indicated in the following Table 1.

TABLE 1:

| Ex. No. | R¹ | R² | R³ | R⁴ | R⁵ | Y | salt with | melting point (decomposition) |
|---|---|---|---|---|---|---|---|---|
| 138 | —(CH₂)₂— | | H | H | H | Cl | HBr | 98 to 99° C |
| 139 | —(CH₂)₃— | | H | H | H | Cl | HBr | 321 to 329° C |
| 140 | —(CH₂)₃— | | H | CH₃ | CH₃ | Cl | HBr | 198° C |
| 141 | CH₃ | CH₃ | H | H | H | Cl | HCl | 200 to 203° C |
| 142 | CH₃ | CH₃ | H | CH₃ | CH₃ | Cl | HCl | 165 to 167° C |
| 143 | C₂H₅ | C₂H₅ | H | CH₃ | CH₃ | Cl | HCl | 132° C |
| 144 | C₂H₅ | C₂H₅ | H | H | H | Cl | HCl | 167° C |

The mercaptoketones required for the Examples indicated above in Table 1, which are the 4'-chloro-3'-sulfamoyl-acetophenone-2-thio (melting point: 139° C.) or the 2-acetylthio-4'-chloro-3'-sulfamoylacetophenone (melting point: 137° C.), were obtained according to the prescription given in Example 104(a). According to the operational method (f) and in an analogous manner to the prescription given in Example 118, there were obtained in the following Examples:

EXAMPLE 145 from 4-chloro-3-dimethylsulfamoyl-phenyllithium with N,N'-dimethylbromoformamidine
the 4-(4-chloro-3-dimethylsulfamoylphenyl)-3-methyl-2-methylimino-1,3-thiazolidine-4-ol-hydrobromide, melting point: 158°–159° C., (decomposition),

EXAMPLE 146 from 4-chloro-3-dimethylsulfamoyl-phenyllithium with N,N'-diethylbromoformamidine
the 3-ethyl-2-ethylimino-4-(4-chloro-3-dimethylsulfamoylphenyl)-1,3-thiazolidine-4-ole-hydrobromide, melting point: 154° C. (decomposition).

The new thioureas of the formula III used in the preceding Examples as starting substances were prepared according to methods disclosed in literature (cf. Houben-Weyl, "Methoden der organischen Chemie", vol. 9, page 884, 4th edition, (1955)). The melting points of the different compounds of the formula III are listed in the following Table 2.

TABLE 2: (thioureas III)

| R¹ | R² | melting point |
|---|---|---|
| CH₃— | (cyclopropyl) | 108° C |
| (CH₃)₂N— | —N(CH₃)₂ | 168° C |
| CH₃O₂C— | —(CH₂)₂—CH₃ | 55° C |
| CH₃—CH—CH₂—<br>  \|<br>  O—CH₃ | —CH₃ | 32° C |
| (CH₃)₂CH— | —N(CH₃)₂ | 134° C |
| CH₃— | —CH₂-(furan) | 78° C |
| CH₂=CH—CH₂ | (cyclopropyl) | 106° C |
| (cyclopropyl) | (cyclopropyl) | 144° C |
| CH₃— | —CH₂-(pyridyl) | 142° C |
| CH₃— | —CH₂-(pyridyl) | 144° C |
| CH₃— | —CH₂-(cyclopentyl) | 95° C |
| CH₃— | —CH₂-(benzodioxole) | 158° C |
| CH₂=CH—CH₂ | —CH₂-(pyridyl) | 75° C |
| (tetrahydropyranyl)—CH₂— | —CH₂-(tetrahydropyranyl) | 67° C |
| (cyclohexyl)H— | —CH₂-(pyridyl) | 104° C |
| (cyclohexyl)H— | —CH₂-(pyridyl) | 198° C |
| (cyclohexyl)H— | —N(CH₃)₂ | 152° C |
| CH₃— | —N-(azepanyl) | 192° C |

For the preparation of further compounds of the invention of the general formula I the sulfamoyl halogen ketones of the general formula II indicated in the following Table 3 were synthesized:

TABLE 3:

Sulfamoyl halogen ketones (II) from sulfamoyl ketones (XV), prepared in a manner analogous to Example 1a).

| $R^3$ | $R^4$ | $R^5$ | Y | Z | Melting point (°C) |
|---|---|---|---|---|---|
| H | $CH_3-$ | H | Cl | Br | 148 |
| H | $CH_3(CH_2)_3-$ | H | Cl | Br | 104 |
| H | $CH_3(CH_2)_2-$ | $CH_3(CH_2)_2-$ | Cl | Br | 57 |
| H | H | $CH_3-CH-CH_2-CH_3$ | Cl | Br | 108 |
| H | H | cyclohexyl- | Cl | Br | 114 |
| H | H | phenyl-$(CH_2)_2-$ | Cl | Br | 138 |
| H | $-(CH_2)_4-$ | | Cl | Br | 127 |
| H | $-(CH_2)_5-$ | | Cl | Br | 108 |
| H | $CH_3-$ | phenyl-$CH_2-$ | Cl | Br | 103 |
| H | H | cyclopentyl- | Cl | Br | 108 |
| H | H | cyclohexyl-$CH_2-$ | Cl | Br | 99 |
| H | H | $C_2H_5-$ | Cl | Br | 106 |
| H | H | $(H_3C)_2CH-CH_2-$ | Cl | Br | 100 |
| H | H | $H_3C-$(p-phenylene)$-CH_2-$ | Cl | Br | 116 |
| H | H | H | Br | Br | 179 |
| $C_2H_5-$ | H | $C_6H_5-CH_2-$ | Cl | Br | 111 |
| $CH_3-$ | H | cyclohexyl- | Cl | Br | 153 |
| $CH_3-$ | H | $C_6H_5-CH_2-$ | Cl | Br | 116 |
| $CH_3-$ | H | $CH_3-CH-CH_2-CH_3$ | Cl | Br | 166 |
| $CH_3-$ | H | $CH_3-$ | Cl | Br | 91 |

The sulfamoyl ketones (XV) required for the sulfamoyl halogen ketones (II) indicated in Table 3 were prepared by the action of amine (VII) on a sulfochloride (IV) and are indicated in Table 4:

TABLE 4:

| Sulfamoyl ketones (XV) | | | | |
|---|---|---|---|---|
| $R^3$ | $R^4$ | $R^5$ | Y | Melting point (°C) |
| H | $CH_3$ | H | Cl | 153 |

TABLE 4:-continued
Sulfamoyl ketones (XV)

| R³ | R⁴ | R⁵ | Y | Melting point (°C) |
|---|---|---|---|---|
| H | CH₃(CH₂)₃— | H | Cl | 55 |
| H | CH₃(CH₂)₂— | H | Cl | 74 |
| H | H | CH₃—CH(—)—CH₂—CH₃ | Cl | 89 |
| H | H | —C₆H₅—(CH₂)₂— | Cl | 87 |
| H | H | cyclohexyl- | Cl | 109 |
| H | | —(CH₂)₅— | Cl | 112 |
| H | | —(CH₂)₄— | Cl | 98 |
| H | CH₃ | C₆H₅—CH₂— | Cl | 97 |
| H | H | cyclopentyl | Cl | 82 |
| H | H | C₂H₅— | Cl | 116 |
| H | H | cyclohexyl-CH₂— | Cl | 114 |
| H | H | (H₃C)₂CH—CH₂— | Cl | 60 |
| H | H | H₃C—C₆H₄—CH₂— | Cl | 85 |
| H | H | H | Br | 161 |
| C₂H₅— | H | C₆H₅—CH₂— | Cl | 112 |
| CH₃— | H | cyclohexyl | Cl | 63 |
| CH₃— | H | C₆H₅—CH₂— | Cl | 80 |
| CH₃— | H | CH₃—CH(—)—CH₂—CH₃ | Cl | 65 |
| CH₃— | H | CH₃— | Cl | 124 |

We claim:

1. A thiazolidine compound of the formula

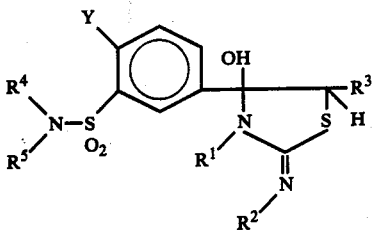

or an acid addition salt thereof with a pharmaceutically acceptable acid, wherein $R^1$ and $R^2$, taken together, are alkylene having 2 to 4 carbon atoms; $R^3$ is hydrogen or alkyl having 1 to 2 carbon atoms; $R^5$ is hydrogen and $R^4$ is hydrogen, alkyl, or alkenyl having up to 6 carbon atoms, or such alkyl or alkenyl which is substituted by alkoxy having 1 to 4 carbon atoms, or $R^5$ is hydrogen and $R^4$ is cycloalkyl having 3, 5, or 6 carbon atoms, cyclohexylmethyl, phenyl, phenylalkyl having 1 to 3 carbon atoms in the alkyl moiety, or such phenylalkyl the phenyl ring of which is substituted by one or two halogen atoms, by one to three methoxy groups, by one alkyl group, or by one methylenedioxy group, or $R^4$ and $R^5$ are each methyl; and Y is hydrogen, halogen, methyl or trifluoromethyl.

2. A compound as claimed in claim 1 wherein $R^1$ and $R^2$ taken together are alkylene having 2 carbon atoms.

3. A compound as claimed in claim 1 wherein $R^1$ and $R^2$ taken together are alkylene having 3 carbon atoms.

4. A compound as in claim 1 wherein $R^1$ and $R^2$ taken together are alkylene having 4 carbon atoms.

5. A pharmaceutical composition for inducing salidiuresis, said composition comprising a salidiuretically effective amount of a compound as in claim 1 in combination with a pharmaceutically acceptable carrier.

6. A pharmaceutical composition as in claim 5 containing from 10 mg to 100 mg of said compound.

7. The method of inducing salidiuresis in a patient which comprises administering to said patient a salidiuretically effective amount of a compound as in claim 1.

8. A compound as claimed in claim 1, which is 3-(4-chloro-3-sulfamoylphenyl)-3-hydroxy-2,3,5,6-tetrahydroimidazo[2,1-b]-thiazole-hydrobromide.

9. A compound as claimed in claim 1, which is 3-(4-chloro-3-sulfamoylphenyl)-3-hydroxy-2,3,6,7-tetrahydro-5H-thiazolo-[3,2-a]-pyrimidine-hydrochloride.

10. A compound as claimed in claim 1, which is 3-(4-chloro-3-sulfamoylphenyl)-6,6-dimethyl-3-hydroxy-2,3,5,6-tetrahydro-imidazo[2,1-b]-thiazole-hydrobromide.

* * * * *

UNITED STATES PATENT AND TRADEMARK OFFICE
CERTIFICATE OF CORRECTION

PATENT NO. : 4,125,614

DATED : November 14, 1978

INVENTOR(S) : Lang et al.

It is certified that error appears in the above—identified patent and that said Letters Patent is hereby corrected as shown below:

Column 45, line 5 from below, the formula "OH$_2$-" in the column headed "R$^2$" should be -- -CH$_2$- --.

Signed and Sealed this

Sixteenth Day of November 1982

[SEAL]

Attest:

GERALD J MOSSINGHOFF

*Attesting Officer*     *Commissioner of Patents and Trademarks*